(12) United States Patent
Round et al.

(10) Patent No.: US 11,103,566 B2
(45) Date of Patent: Aug. 31, 2021

(54) ANTIGEN SPECIFIC TREGS AND RELATED COMPOSITIONS, METHODS AND SYSTEMS

(71) Applicant: CALIFORNIA INSTITUTE OF TECHNOLOGY, Pasadena, CA (US)

(72) Inventors: June L. Round, Salt Lake City, UT (US); Sarkis K. Mazmanian, Porter Ranch, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 473 days.

(21) Appl. No.: 15/499,805

(22) Filed: Apr. 27, 2017

(65) Prior Publication Data
US 2018/0055919 A1    Mar. 1, 2018

Related U.S. Application Data

(63) Continuation of application No. 13/112,725, filed on May 20, 2011, now abandoned.

(60) Provisional application No. 61/346,837, filed on May 20, 2010.

(51) Int. Cl.
    *A61K 39/00*     (2006.01)
    *C12N 5/0783*     (2010.01)
    *A61K 35/12*     (2015.01)

(52) U.S. Cl.
CPC ........ *A61K 39/0008* (2013.01); *C12N 5/0637* (2013.01); *A61K 35/12* (2013.01); *A61K 2039/5158* (2013.01); *A61K 2039/6087* (2013.01); *C12N 2501/90* (2013.01)

(58) Field of Classification Search
None
See application file for complete search history.

(56) References Cited

U.S. PATENT DOCUMENTS

| | | | |
|---|---|---|---|
| 5,571,900 A | 11/1996 | Wiegand et al. | |
| 7,026,283 B2 | 4/2006 | Fleming et al. | |
| 7,384,645 B2 * | 6/2008 | Foster | A61K 31/739 424/250.1 |
| 9,057,070 B2 | 6/2015 | Mazmanian et al. | |
| 9,265,790 B2 | 2/2016 | Tzianabos et al. | |
| 9,452,189 B2 | 9/2016 | Mazmanian et al. | |
| 9,539,281 B2 | 1/2017 | Kasper et al. | |
| 2002/0146396 A1 * | 10/2002 | Albert | A61K 39/0008 424/93.21 |
| 2004/0063685 A1 | 4/2004 | Ilzawa et al. | |
| 2004/0219160 A1 * | 11/2004 | Tzianabos | A61K 31/715 424/184.1 |
| 2005/0119164 A1 * | 6/2005 | Taylor | A61K 31/726 435/41 |
| 2006/0029662 A1 | 2/2006 | Calias et al. | |
| 2006/0127387 A1 | 6/2006 | Zikria et al. | |
| 2006/0276378 A1 | 12/2006 | Wilson et al. | |
| 2007/0041986 A1 * | 2/2007 | Blaszczak | A61K 39/39 424/184.1 |
| 2008/0311140 A1 * | 12/2008 | Lee | A61K 39/001 424/184.1 |
| 2010/0275282 A1 | 10/2010 | Round et al. | |
| 2011/0002965 A1 | 1/2011 | Round et al. | |
| 2013/0195802 A1 | 8/2013 | Moore | |
| 2014/0072534 A1 | 3/2014 | Mazmanian et al. | |
| 2014/0335131 A1 | 11/2014 | Mazmanian et al. | |
| 2016/0022727 A1 | 1/2016 | Round et al. | |
| 2016/0030464 A1 | 2/2016 | Mazmanian et al. | |
| 2016/0143940 A1 | 5/2016 | Shen et al. | |
| 2016/0151408 A1 | 6/2016 | Mazmanian et al. | |
| 2016/0361343 A1 | 12/2016 | Mazmanian et al. | |
| 2017/0003274 A1 | 1/2017 | Round et al. | |
| 2018/0264026 A1 | 9/2018 | Round et al. | |
| 2019/0022128 A1 | 1/2019 | Mazmanian et al. | |
| 2019/0314400 A1 | 10/2019 | Shen et al. | |
| 2019/0336545 A1 | 11/2019 | Mazmanian et al. | |
| 2020/0197436 A1 | 6/2020 | Round et al. | |

FOREIGN PATENT DOCUMENTS

| | | |
|---|---|---|
| CA | 2800174 A1 | 11/2011 |
| DE | 3704389 A1 | 8/1988 |
| EP | 0371414 A2 | 6/1990 |
| EP | 0382576 A1 | 8/1990 |
| EP | 0497524 A2 | 8/1992 |
| EP | 1358885 A1 | 11/2003 |
| EP | 2217250 A2 | 8/2010 |
| EP | 2422200 A2 | 2/2012 |
| EP | 2571982 A1 | 3/2013 |
| EP | 2994161 A1 | 3/2016 |
| EP | 2764090 B1 | 12/2017 |
| EP | 2555753 B1 | 8/2018 |

(Continued)

OTHER PUBLICATIONS

Meltzer et al., 2006, Infect. Immun. Vol. 74: 1890-1895.*

(Continued)

*Primary Examiner* — Amy E Juedes
(74) *Attorney, Agent, or Firm* — Steinfl + Bruno LLP

(57) ABSTRACT

Antigen specific regulatory T cells are described and related compositions, methods and systems. Methods to generate an antigen specific anti-inflammatory regulatory T cell is provided, the method comprising contacting either a T cell or an antigen presenting cell with a zwitterionic polysaccharide conjugated to the antigen for a time and under condition to generate an antigen specific regulatory T cell that is capable of inhibiting a pro-inflammatory response against the antigen.

19 Claims, 35 Drawing Sheets

Specification includes a Sequence Listing.

(56) References Cited

FOREIGN PATENT DOCUMENTS

| | | | |
|---|---|---|---|
| GB | 2286193 A | 8/1995 |
| HK | 1201291 A1 | 8/2015 |
| JP | S56128721 A | 10/1981 |
| JP | H10507746 A | 7/1998 |
| JP | 2012524910 A | 10/2012 |
| JP | 2013530949 A | 8/2013 |
| JP | 2016521284 A | 7/2016 |
| JP | 6027961 B2 | 11/2016 |
| JP | 6296367 B2 | 3/2018 |
| JP | 6471888 B2 | 2/2019 |
| WO | 95/31990 A1 | 11/1995 |
| WO | 96/07427 A1 | 3/1996 |
| WO | 96/32119 A1 | 10/1996 |
| WO | 96/35433 A1 | 11/1996 |
| WO | 98/42718 A1 | 10/1998 |
| WO | 98/45335 A1 | 10/1998 |
| WO | 00/01733 A1 | 1/2000 |
| WO | 02//07741 A1 | 1/2002 |
| WO | 03/075953 A2 | 9/2003 |
| WO | 03/077863 A2 | 9/2003 |
| WO | 2007/040446 A1 | 4/2007 |
| WO | 2009/149149 A1 | 12/2009 |
| WO | 2011/056703 A1 | 5/2011 |
| WO | 2011/127302 A2 | 10/2011 |
| WO | 2011/146910 A1 | 11/2011 |
| WO | 2012/027032 A1 | 3/2012 |
| WO | 2012/103532 A1 | 8/2012 |
| WO | 2013/009945 A1 | 1/2013 |
| WO | 2013/019896 A1 | 2/2013 |
| WO | 2013/052099 A2 | 4/2013 |
| WO | 2014/182966 A1 | 11/2014 |

OTHER PUBLICATIONS

Mazmanian et al., 2006, Nat. Rev. Vol. 6: 849-858.*
Liu et al., Online Nov. 2008, J. Cell. Mol. Med. vol. 13: 1765-1774.*
Telesford et al., 2015: Gut Microbes, vol. 6: 234-242.*
Gallorini et al., 2009, PNAS vol. 106: 17481-17486.*
Round et al., 2011, Science, pp. 974-977.*
Toebaketal., Jan. 2009, Contact Derm. vol. 60: 2-20.*
Quaresma, 2019, Clin. Microbio. Rev. vol. 32: 1-35.*
Advisory Action for U.S. Appl. No. 13/112,725, dated Mar. 4, 2014, 3 pages.
Aharoni R., et al., "Bystander Suppression of Experimental Autoimmune Encephalomyelitis by T Cell Lines and Clones of the Th2 Type Induced by Copolymer 1," Journal of Neuroimmunology, Nov. 1998, vol. 91 (1-2), 12 pages.
Aharoni R., et al., "Copolymer 1 Induces T Cells of the T Helper Type 2 that Crossreact with Myelin Basic Protein and Suppress Experimental Autoimmune Encephalomyelitis," Proceedings of the National Academy of Sciences of the United States of America, Sep. 1997, vol. 94 (20), 6 pages.
Akbari O., et al., "Antigen-Specific Regulatory T Cells Develop via the ICOS-ICOS-ligand Pathway and Inhibit Allergen-Induced Airway Hyperreactivity," Nature Medicine, Sep. 2002, vol. 8 (9), 9 pages.
American Lung Association, "Acute Respiratory Disease Syndrome: What is acute respiratory disease syndrome?," retrieved from the Internet: URL:http://www.lungusa.org/site/apps/nlnet/content3.aspz?c=dvLUK900E&b=2058817&content, retrieved on Sep. 24, 2008, 3 pages.
Arnon R., et al., "New Insights into the Mechanism of Action of Copolymer 1 in Experimental Allergic Encephalomyelitis and Multiple Sclerosis," Journal of Neurology, Apr. 1996, vol. 243 (4 Suppl 1), 8 pages.
Asadullah K., et al., "Interleukin-10 Therapy-Review of a New Approach," Pharmacological Reviews, Jun. 2003, vol. 55 (2), 29 pages.
Azzawi M., et al., "Identification of Activated T Lymphocytes and Eosinophils in Bronchial Biopsies in Stable atopic Asthma," The American Review of Respiratory Disease, Dec. 1990, vol. 142 (6 Pt 1), 7 pages.
Barutca S., et al., "Prevention of Interleukin-2-Induced Severe Bronchospasm with Salbutamol," Journal of Aerosol Medicine, 2003, vol. 16 (2), 2 pages.
Basu S., et al., "Synthesis and Characterization of a Peptide Nucleic Acid Conjugated to a D-Peptide Analog of Insulin-like Growth Factor 1 for Increased Cellular Uptake," Bioconjugate Chemistry, Jul.-Aug. 1997, vol. 8 (4), 9 pages.
Batta G., et al., "Conformational Stabilization of the Altruronic Acid Residue in the O-Specific Polysaccharide of Shigella Sonnei/Plesiomonas Shigelloides," Carbohydrate Research, Dec. 1997, vol. 305 (1), 7 pages.
Bayley D.P., et al., "Analysis of cepA and Other Bacteroides Fragilis Genes Reveals a Unique Promoter Structure," FEMS Microbial Letters, Dec. 2000, vol. 193 (1), 6 pages.
Bazan J.F., et al., "Unraveling the Structure of IL-2," Science, Jul. 1992, vol. 257 (5068), 7 pages.
Berggren S. M., et al., "Decreasing Serum Concentrations of All-trans, 13-cis Retinoic Acids and Retinol During Fasting and Caloric Restriction," Journal of Internal Medicine, Mar. 2003, vol. 253 (3), 6 pages.
Bernatowska-Matuszkiewicz E., et al., "IgG Subclasses and Antibody Response to Pneumococcal Capsular Polysaccharides in Children With Severe Sinopulmonary Infections and Asthma," Immunological Investigations, Apr. 1991, vol. 20 (2), 13 pages.
Bhaduri S., et al., "Simple and Rapid Method for Disruption of Bacteria for Protein Studies," Applied and Environmental Microbiology, Oct. 1983, vol. 46 (4), 3 pages.
Blander J.M., et al., "Toll-dependent Selection of Microbial Antigens for Presentation by Dendritic Cells," Nature, Apr. 2006, vol. 440 (7085), 5 pages.
Blomfield I.C., et al., "Lrp Stimulates Phase Variation of Type 1 Fimbriation in *Escherichia coli* K-12," Journal of Bacteriology, Jan. 1993, vol. 175 (1), 10 pages.
Borsellino G., et al., "Expression of Ectonucleotidase CD39 by Foxp3+ Treg Cells: Hydrolysis of Extracellular ATP and Immune Suppression," Blood, Aug. 2007, vol. 110 (4), 9 pages.
Braat H. et al., "A Phase I Trial With Transgenic Bacteria Expressing Interleukin-10 in Crohn's Disease," Clinical Gastroenterology and Hepatology, Jun. 2006, vol. 4 (6), 6 pages.
Brichford, "Can You Prevent Multiple Sclerosis?," Understanding Factors That Increase Your Risk of Multiple Sclerosis and What—if Anything—You Can Do About Them, EverydayHealth.com., Dec. 2008, 2 pages.
Brubaker J.O., et al., "Mitogenic Activity of Purified Capsular Polysaccharidea From Bacteroides Fragilis: Differential StimulatoryEffect on Mouse and Rat Lymphocytes in Vitro," Journal of Immunology, Feb. 1999, vol. 162 (4), 9 pages.
Budinger L., et al., "Immunologic Mechanisms in Hypersensitivity Reactions to Metal Ions: An Overview," Allergy, Feb. 2000, vol. 55 (2), 8 pages.
Burgers W.A., et al., "The Challenges of HIV Vaccine Development and Testing," Best Practice & Research Clinical Obstetrics & Gynaecology, Apr. 2005, vol. 19 (2), 15 pages.
Byers S.W., et al., "Mechanism of Action of Vitamin D and the Vitamin D Receptor in Colorectal Cancer Prevention and Treatment," Reviews in Endocrine and Metabolic Disorders, Kluwer Academic Publishers, BO, vol. 13(1), Aug. 23, 2011, 13 pages.
Chatila T.A., "Role of Regulatory T Cells in Human Diseases," The Journal of Allergy and Clinical Immunology, Nov. 2005, vol. 116 (5), 11 pages.
Chen D.J., et al., "Delivery of Foreign Antigens by Engineered Outer Membrane Vesicle Vaccines," Proceedings of the National Academy of Sciences of the United States of America, Feb. 2010, vol. 107 (7), 6 pages.
Chen J., et al., "DNA Inversion on Conjugative Plasmid pVT745," Journal of Bacteriology, Nov. 2002, vol. 184 (21), 9 pages.
Cobb B.A., et al., "Zwitterionic Capsular Polysaccharides: the New MHCII-Dependent Antigens," Cellular Microbiology, Oct. 2005, vol. 7 (10), 6 pages.

(56) References Cited

OTHER PUBLICATIONS

Comstock L.E., et al., "Analysis of a Capsular Polysaccharide Biosynthesis Locus of Bacteroides Fragilis," Infection and Immunity, Jul. 1999, vol. 67 (7), 8 pages.
Comstock L.E., et al., "Bacterial Glycans: Key Mediators of Diverse Host Immune Responses," Cell, Sep. 2006, vol. 126 (5), 4 pages.
Comstock L.E., et al., "Interstrain Variation of the Polysaccharide B Biosynthesis Locus of Bacteroides Fragilis: Characterization of the Region from Strain 638R," Journal of Bacteriology, Oct. 1999, vol. 181 (19), 5 pages.
Conesa A., et al., "Interleukin-2 Induces Peroxide Production by Primed Normodense Eosinophils of Patients With Asthma," Allergy and Asthma Proceedings, Jan.-Feb. 2003, vol. 24 (1), 7 pages.
Crabb J.H., et al., "T Cell Regulation of Bacteroides Fragilis-induced Intraabdominal Abscesses.," Reviews of Infectious Diseases, Jan. 1990, vol. 12 Suppl 2, 7 pages.
Craig R.M., et al., "Autologous Hematopoietic Stem Cell Transplantation for Crohn's Disease," Autoimmunity Reviews, Feb. 2009, vol. 1 (4), 6 pages.
Dadley-Moore, "The Sweet Side of Maturation," Nature Reviews Immunology, Sep. 2005, vol. 5, 1 page.
Dahiyat B.L., et al., "De Novo Protein Design: Fully Automated Sequence Selection," Science, Oct. 1997, vol. 278 (5335), 7 pages.
Decision on Rejection for JP2010533311 dated Oct. 29, 2013 in the name of California Institute of Echnology (English Translation+ Japanese Original), 2 pages.
Deib A., et al., "Treating Multiple Sclerosis with Monoclonal Antibodies: A 2013 Update," Expert Review of Neurotherapeutics, Mar. 2013, vol. 13 (3), 23 pages.
Deslongchamps P., et al., "Ozonolysis of Acetals, (1) Ester Synthesis, (2) THP Ether Cleavage, (3) Selective Oxidation of B-Giycoside, (4) Oxidative Removal of Benzylidene and Ethylidene Protecting Groups," Canadian Journal of Chemistry, Apr. 1971, vol. 49, 6 pages.
Deslongchamps P., et al., "The Importance of Conformationin the Ozonolysis of Acetals," Canadian Journal of Chemistry, Jul. 1972, vol. 52, 3 pages.
Deslongchamps P., et al., "The Oxidation of Acetals by Ozone," Canadian Journal of Chemistry, Apr. 1974, vol. 52, 14 pages.
Dias N., et al., "Antisense Oligonucleotides: Basic Concepts and Mechanisms," Molecular Cancer Therapeutics, Mar. 2007, vol. 1 (5), 9 pages.
Difabio J.L., et al., "Structure of the Capsular Polysaccharide Antigen of Type IV Group B *Streptococcus*," Canadian Journal of Chemistry, Oct. 1989, vol. 67, 6 pages.
Doig C., et al., "The Efficacy of the Heat Killing of *Mycobacterium tuberculosis*," Journal of Clinical Pathology, Oct. 2002, vol. 55 (10), 2 pages.
Dooms H., et al., "Revisiting the Role of IL-2 in Autoimmunity," European Journal of Immunology, Jun. 2010, vol. 40 (6), 3 pages.
Drug Absorption, Bioavailability and Routes of Administration, Goodman & Oilman's The Pharmacological Basis of Therapeutics, Tenth Edition, McGraw-Hill Medical Publishing Edition, New York, 2001, 6 pages.
Eisenstein B.I., et al., "Integration Host Factor is Required for the DNA Inversion that Controls Phase Variation in *E.coli*," Proceedings of the National Academy of Sciences of the United States of America, Sep. 1987, vol. 84 (18), 5 pages.
European Search Opinion for European Applicaton No. EP2217250, dated Dec. 8, 2010, 5 pages.
Excerpts from Immunobiology, in ed. 2008, Elsevier, Amsterdam, Netherlands, 24 pages.
Extended European Search Report for European Application No. 12811896.5, dated Jun. 1, 2015, 11 pages.
Extended European Search Report for European Application No. 14795204.8, dated Dec. 8, 2016, 9 pages.
Extended European Search Report for European Application No. 11766746.9, dated Sep. 13, 2013, 5 pages.
Extended European Search Report for the European Application No. 11784368.0, dated Dec. 2, 2013, 13 pages.

Final Office Action for U.S. Appl. No. 10/814,620, dated Oct. 7, 2009, 24 pages.
Final Office Action for U.S. Appl. No. 13/112,725, dated Jan. 7, 2015, 15 pages.
Final Office Action for U.S. Appl. No. 13/112,725, dated Oct. 24, 2013, 8 pages.
Finberg R.W., et al., "Decay-accelerating Factor Expressionon Either Effector or Target Cells Inhibits Cytotoxicity by Human Natural Killer Cells," Journal of Immunology, Sep. 1992, vol. 149 (6), 6 pages.
Fournier J.M., et al., "Isolation of Type 5 Capsular Polysaccharide from *Staphylococcus aureus*," Annales De L'institut Pasteur. Microbiology, Sep. 1987, vol. 138 (5), 7 pages.
Fridkis-Hareli M., et al., "Direct Binding of Myelin Basic Protein and Synthetic Copolymer 1 to Class II Major Histocompatibility Complex Molecules on Living Antigen-presenting Cells—Specificity and Promiscuity," Proceedings of the National Academy of Sciences of the United States of America, May 1994, vol. 91 (11), 5 pages.
Fridkis-Hareli M., et al., "Binding Motifs of Copolymer 1 to Multiple Sclerosis and Rheumatoid Arthritis-associated HLA-DR Molecules," Journal of Immunology, Apr. 1999, vol. 162 (8), 9 pages.
Fridkis-Hareli M., et al., "Binding of Random Copolymers of Three Amino Acids to Class II MHC Molecules," International Immunology, May 1999, vol. 11 (5), 7 pages.
Fridkis-Hareli M., et al., "Synthetic Copolymer 1 and Myelin Basic Protein Do Not Require Processing Prior to Binding to Class II Major Histocompatibility Complex Molecules on Living Antigen-presenting Cells," Cell Immunlogy, Jul. 1995, vol. 163 (2), 10 pages.
Fujino S., et al., "Increased Expression of Interleukin 17 in Inflammatory Bowel Disease," Gut, Jan. 2003, vol. 52 (1), 6 pages.
Gally D.L., et al., "Environmental Regulation of the Fim Switch Controlling Type 1 Fimbrial Phase Variation in *Escherichia coli* K-12: Effects of Temperature and Media," Journal of Bacteriology, Oct. 1993, vol. 175 (19), 8 pages.
Gelu-Simeon M., et al., "Evolution and Predictive Factors of Thyroid Disorder Due to Interferon Alpha in the Treatment of Hepatitis C," World Journal of Gastroenterology, Jan. 2009, vol. 15 (3), 6 pages.
GenBank Accession No. AJ277832; Hutloff, Jan. 19, 2001, 2 pages.
GenBank Accession No. CAC06612; Hutloff, Jan. 19, 2001, 2 pages.
GenBank Accession No. NM012092; Dec. 20, 2003, 4 pages.
GenBank Accession No. NP036224, Dec. 20, 2003, 3 pages.
Gibson et al., "Chapter 5: trans-Galactooligosaccharides as Prebiotics," in: Handbook of Functional Dairy Products, Colette S., ed., CRC Press Publishing, 2004, 18 pages.
Gibson F.C III., et al., "The Capsular Polysaccharide Complex of Bacteroides Fragilis Induces Cytokine Production From Human and Murine Phagocytic Cells," Infection and Immunity, Mar. 1996, vol. 64 (3), 5 pages.
Gilbert J.A., et al., "Toward Effective Probiotics for Autism and Other Neurodevelopmental Disorders," Cell, Dec. 2013, vol. 155 (7), 3 pages.
Glazebrook J., et al., "A Novel Exopolysaccharide can Function in Place of the Calcofluor-binding Exopolysaccharide in Nodulation of Alfalfa by Rhizobium Meliloti," Cell, Feb. 1989, vol. 56 (4), 12 pages.
Golgher D.B., et al., "Galactofuranose-containing Glycoconjugates of Epimastigote and Trypomastigote Forms of Trypanosoma Cruzi," Molecular and Biochemical Parasitology, Aug. 1993, vol. 60 (2), 16 pages.
Gonzalez-Hernandez Y., et al., "Peripheral Blood CD161+ T Cells from Asthmatic Patients are Activated During Asthma Attack and Predominantly Produce IFN-gamma," Scandinavian Journal of Immunology, Apr. 2007, vol. 65 (4), 8 pages.
Grabow W.O.K., "Bacteriophages: Update on Application as Models for Viruses in Water," Water SA, 2001, vol. 27 (2), 18 pages.
Groux H., "Type 1 T-regulatory Cells: Their Role in the Control of Immune Responses," Transplantation, May 2003, vol. 75(9 Suppl), 5 pages.

(56) References Cited

OTHER PUBLICATIONS

Hafler D.A., et al., "Anti-CD4 and Anti-CD2 Monoclonal Antibody Infusions in Subjects with Multiple Sclerosis. Immunosuppressive Effects and Human Anti-mouse Responses," Journal of Immunology, Jul. 1988, vol. 141 (1), 8 pages.

Hamelmann E., et al., "Noninvasive Measurement of Airway Responsiveness in Allergic Mice Using Barometric Plethysmography," American Journal of Respiratory and Critical Care Medicine, Sep. 1997, vol. 156 (3 Pt 1), 10 pages.

Haregewoin A., et al., "Human Gamma Delta+ T Cells Respond to Mycobacterial Heat-shock Protein," Nature, Jul. 1989, vol. 340 (6231), 4 pages.

Harth G., et al., "Treatment of *Mycobacterium tuberculosis* With Antisense Oligonucleotides to Glutamine Synthetase mRNA Inhibits Glutamine Synthetase Activity, Formation of the Poly-l-glutamate/glutamine Cell Wall Structure, and Bacterial Replication," Proceedings of the National Academy of Sciences of the United States of America, Jan. 2000, vol. 97 (1), 6 pages.

Hertl M., et al., "T Cell Control in Autoimmune Bullous Skin Disorders," The Journal of Clinical Investigation, May 2006, vol. 116 (5), 8 pages.

Hirata N., et al., "Cytokine Synthesis of Human Monocytes Stimulated by Triple or Single Helical Conformer of an Antitumour (1->3)-beta-D-glucan Preparation, Sonifilan," Zentralblatt für Bakteriologie, Nov. 1998, vol. 288 (3), 12 pages.

Hodge G., et al., "Allium Sativum (Garlic) Suppresses Leukocyte Inflammatory Cytokine Production in Vitro: Potential Therapeutic Use in the Treatment of Inflammatory Bowel Disease," Cytometry, Aug. 2002, vol. 48 (4), 7 pages.

Hofstetter H., et al., "Th17 Cells in MS and Experimental Autoimmune Encephalomyelitis," International MS Journal, Apr. 2009, vol. 16(1), 7 pages.

Huibregtse I.L. et al., "Immunopathogenesis of IBD: Insufficient Suppressor Function in the Gut?," Gut, Apr. 2007, vol. 56 (4), 9 pages.

Hutloff A., et al., "ICOS is an Inducible T-cell Co-stimulator Structurally and Functionally Related to CD28," Nature, Jan. 1999, vol. 397 (6716), 4 pages.

International Preliminary Report on Patentability for Application No. PCT/US2008/082928, dated May 11, 2010, 6 pages.

International Preliminary Report on Patentability for Application No. PCT/US2010/032300, dated Oct. 25, 2011, 6 pages.

International Preliminary Report on Patentability for Application No. PCT/US2012/023050, dated Jul. 30, 2013, 5 pages.

International Preliminary Report on Patentability for Application No. PCT/US2014/037392, dated Nov. 10, 2015, 8 pages.

International Search Report and Written Opinion for Application No. PCT/US2011/031606, dated Dec. 15, 2011, 11 pages.

Itokazu M., et al., "Abscess Formation as a Complication Caused by Postoperative Osteomyelitis of the Femur," Archives of Orthopaedic and Trauma Surgery, 1998, vol. 118 (1-2), 4 pages.

Jennings H.J., et al., "Immunochemistry of Groups A, B, and C Meningococcal Polysaccharide-tetanus Toxoid Conjugates," Journal of Immunology, Sep. 1981, vol. 127 (3), 8 pages.

Jennings H.J., et al., "Induction of Meningococcal Group B Polysaccharide-specific IgG Antibodies in Mice by Using an N-propionylated B Polysaccharide-tetanus Toxoid Conjugate Vaccine," Journal of Immunology, Sep. 1986, vol. 137 (5), 8 pages.

Jia W. et al., "Gut Microbiota: A Potential New Territory for Drug Targeting," Nature Reviews. Drug Discovery, Feb. 2008, vol. 7 (2), 7 pages.

Johnson J.L., et al., "Bacterial Capsular Polysaccharide Prevents the Onset of Asthma Through T-cell Activation," Glycobiology, Apr. 2015, vol. 25 (4), 8 pages.

Jonuleit H., et al., "Identification and Functional Characterization of Human CD4(+)CD25(+) T Cells With Regulatory Properties Isolated From Peripheral Blood," The Journal of Experimental Medicine, Jun. 2001, vol. 193 (11), 10 pages.

Jonuleit H., et al., "The Regulatory T Cell Family: Distinct Subsets and Their Interrelations," Journal of Immunology, Dec. 2003, vol. 171 (12), 6 pages.

Jotwani R. et al., "Pathogenicity of Bacteroides Fragilis Group in Rat Intra-abdominal Abscesses," Microbiology and Immunology, 1992, vol. 36 (10), 11 pages.

Kalka-Moll W.M., et al., "Bacteriodes Fragilis NCTC 9343 Capsular Polysaccharide PS A and the Effect of Chain Length of T cell Proliferation," American Society for Microbiology, 1998, vol. 98, 3 pages.

Kalka-Moll W.M., et al., "Immunochemical and Biological Characterization of Three Capsular Polysaccharides From a Single Bacteroides Fragilis Strain," Infection and Immunity, Apr. 2001, vol. 69 (4), 6 pages.

Kasper D.L., et al., "Capsular Polysaccharides and Lipopolysaccharides From Two Bacteroides Fragilis Reference Strains: Chemical and Immunochemical Characterization," Journal of Bacteriology, Feb. 1983, vol. 153 (2), 7 pages.

Kasper D.L., et al., "Protective Efficacy of Immunization With Capsular Antigen Against Experimental Infection With Bacteroides Fragilis," The Journal of Infectious Diseases, Nov. 1979, vol. 140 (5), 8 pages.

Kasper D.L., et al., "Surface Antigens as Virulence Factors in Infection With Bacteroides Fragilis," Reviews of Infectious Diseases, Mar.-Apr. 1979, vol. 1 (2), 13 pages.

Kasper D.L., "The Polysaccharide Capsule of Bacteroides Fragilis Subspecies Fragilis: Immunochemical and Morphologic Definition," The Journal of Infectious Diseases, Jan. 1976, vol. 133 (1), 7 pages.

Kato T., et al., "Interleukin 10 Reduces Mortality From Severe Peritonitis in Mice," Antimicrobial Agents and Chemotherapy, Jun. 1995, vol. 39 (6), 5 pages.

Kennedy R., et al., "Prevention of Experimental Postoperative Peritoneal Adhesions by N,O-carboxymethyl Chitosan," Surgery, Nov. 1996, vol. 120 (5), 7 pages.

Kernodle D.S., et al., "Expression of an Antisense Hla Fragment in *Staphylococcus aureus* Reduces Alpha-toxin Production in Vitro and Attenuates Lethal Activity in a Murine Model," Infection and Immunity, Jan. 1997, vol. 65 (1), 6 pages.

Kinoshita K. et al., "Retinoic Acid Reduces Autoimmune Renal Injury and Increases Survival in NZB/WF1 Mice," Journal of Immunology, Jun. 2003, vol. 170 (11), 7 pages.

Knetsch M.L.W., et al., "Polymers With Tunable Toxicity: a Reference Scale for Cytotoxicity Testing of Biomaterial Surfaces," Journal of Biomedical Materials Research. Part A, Sep. 2007, vol. 82 (4), 9 pages.

Knirel Y., et al., "Somatic Antigens of Pseudomonas Aeruginosa. The Structure of O-specific Polysaccharide Chains of the Lipopolysaccharides From P. Aeruginosa O5 (Lanyi) and Immunotype 6 (Fisher)," European Journal of Biochemistry, Sep. 1987, vol. 167 (3), 13 pages.

Knirel Y., et al., "The Structure of O-specific Polysaccharides and Serological Classification of Pseudomonas Aeruginosa (A Review)," Acta Microbiologica Hungarica, 1988, vol. 35 (1), 12 pages.

Krause T.J., et al., "An Inhibitor of Cell Proliferation Associated With Adhesion Formation is Suppressed by N,O-carboxymethyl Chitosan," Journal of Investigative Surgery, Mar.-Apr. 1998, vol. 11 (2), 9 pages.

Kulicke W.M., et al., "Correlation Between Immunological Activity, Molar Mass, and Molecular Structure of Different (1-->3)-beta-D-glucans," Carbohydrate Research, Jan. 1997, vol. 297 (2), 9 pages.

Kurup V.P., et al., "Antibody Response to Low-molecular-weight Antigens of Aspergillus Fumigatus in Allergic Bronchopulmonary Aspergillosis," Journal of Clinical Microbiology, Jun. 1989, vol. 27 (6), 5 pages.

Lee J.C., et al., "Effects of in Vitro and in Vivo Growth Conditions on Expression of Type 8 Capsular Polysaccharide by *Staphylococcus aureus*," Infection and Immunity, May 1993, vol. 61 (5), 6 pages.

Lee S.A., et al., "Plasma Interleukin-1beta, -6, -8 and Tumor Necrosis Factor-alpha as Highly Informative Markers of Pelvic Inflammatory Disease," Clinical Chemistry and Laboratory Medicine, Jul. 2008, vol. 46 (7), 3 pages.

(56) References Cited

OTHER PUBLICATIONS

Lindberg A.A., et al., "Virulence Factors in Infections With Bacteroides Fragilis: Isolation and Characterization of Capsular Polysaccharide and Lipopolysaccharide," Scandinavian Journal of Infectious Diseases. Supplementum, 1982, vol. 35, 8 pages.
Lupus study, Meet a Lupus Researcher, www.lupusstudy.org/updates.php, Nov. 2005, 2 pages.
Lysnyansky I., et al., "Juxtaposition of an Active Promoter to Vsp Genes via Site-specific DNA Inversions Generates Antigenic Variation in Mycoplasma Bovis," Journal of Bacteriology, Oct. 2001, vol. 183 (19), 11 pages.
MacPherson A., et al., "Mucosal Antibodies in Inflammatory Bowel Disease Are Directed Against Intestinal Bacteria," Gut, Mar. 1996, vol. 38 (3), 11 pages.
MacPherson A.J., et al., "IgA Responses in the Intestinal Mucosa Against Pathogenic and Non-Pathogenic Microorganisms," Microbes and Infection, Oct. 2001, vol. 3 (12), 15 pages.
Makela M.J., et al., "IL-10 Is Necessary for the Expression of Airway Hyperresponsiveness but Not Pulmonary Inflammation After Allergic Sensitization," Proceedings of the National Academy of Sciences of the United States of America, May 2000, vol. 97 (11), 6 pages.
Mamessier E., et al., "Cytokines in Atopic Diseases: Revisiting the Th2 Dogma," European Journal of Dermatology, Mar.-Apr. 2006, vol. 16 (2), 11 pages.
Mazmanian et al., "The Evolution of Symbiosis: From Bacteria to Commensal to Beneficial Microbe," Nature, Macmillan Publishers Limited, Basingstoke, United Kingdom, May 29, 2008, vol. 453, 6 pages.
Mazmanian S.K., et al., "Capsular Polysaccharides of Symbiotic Bacteria Modulate Immune Responses During Experimental Colitis," Journal of pediatric gastroenterology and nutrition, Apr. 2008, vol. 46 (Suppl 1), 20 pages.
McClain M.S., et al., "Inversion-independent Phase Variation of Type 1 Fimbriae in *Escherichia coli*," Journal of Bacteriology, Jul. 1993, vol. 175 (14), 10 pages.
Meisel-Mikolajczyk F., et al., "Human T Cell Adhesion to Endothelium Stimulated by Membrane Components Extracted From Strains of Bacteroides Vulgatus (Member of B. Fragilis Group)," Archivum Immunologiae et Therapiae Experimentalis, 1993, vol. 41 (2), 4 pages.
Miller C.W., et al., "Severe Asthma and the Omalizumab Option," Clinical and Molecular Allergy, May 2008, vol. 6, 14 pages.
Mojtabavi N., et al., "Long-Lived Th2 Memory in Experimental Allergic Asthma," Journal of Immunology, Nov. 2002, vol. 169 (9), 10 pages.
Montz F.J., et al., "Interleukin 10: Ability to Minimize Postoperative Intraperitoneal Adhesion Formation in a Murine Model," Fertility and Sterility, Jun. 1994, vol. 61 (6), 7 pages.
Moore, The List Goes on, New Additions to the Autoimmune Disease Roster. http://autoimmunedisease.suiteiOI.com/blog.cfm/the list goes on, Aug. 7, 2007, 3 pages.
Moorman J.E., et al., "National Surveillance of Asthma: United States, 2001-2010," Vital and Health Statistics Series 3, Nov. 2012, vol. 3 (35), 67 pages.
Mor F., et al., "Identification of Aldolase as a Target Antigen in Alzheimer's Disease," Journal of Immunology, Sep. 2005, vol. 175 (5), 8 pages.
Mora J.R., et al., "Selective Imprinting of Gut-homing T Cells by Peyer's Patch Dendritic Cells," Nature, Jul. 2003, vol. 424 (6944), 6 pages.
Mora J.R., et al., "Generation of Gut-homing IgA-Secreting B Cells by Intestinal Dendritic Cells," Science, Nov. 2006, vol. 314 (5802), 4 pages.
MS the Disease, National Multiple Sclerosis Society, Downloaded from the internet at http://www.nationalmssociety.org/About-the-Society/Press-Room/MS-the-Disease on Dec. 19, 2016, 4 pages (website copyright 2014).
Mulholland K., "Strategies for the Control of Pneumococcal Diseases," Vaccine, Jul. 1999, vol. 17 (Suppl 1), 5 pages.
Natori T., et al., "Agelasphins, Novel Antitumor and Immunostimulatory Cerebrosides From the Marine Sponge Agelas Mauritianus," Tetrahedron, Feb. 1994, vol. 50 (9), 14 pages.
NCBI Sequence View, "Toxin," *Salmonella typhimurium* LT2, Retrieved from the Internet: URL: http://www.ncbi.nim.nih.gov/entrez/viewer.fcgi?db=protein&id= 17233414, retrieved on Aug. 16, 2007, 2 pages.
Nielsen P.E., "Applications of Peptide Nucleic Acids," Current Opinion in Biotechnology, Feb. 1999, vol. 10 (1), 5 pages.
Non-Final Office Action for U.S. Appl. No. 13/112,725, dated Mar. 18, 2016, 11 pages.
Non-Final Office Action for U.S. Appl. No. 13/112,725, dated May 8, 2014, 12 pages.
Non-Final Office Action for U.S. Appl. No. 13/112,725, dated May 30, 2013, 7 pages.
Norman, "Thyroiditis-Inflammation of the Thyroid Gland," Endocrineweb, www.endocrineweb.com/throiditis.html, 2009, retrieved on Jul. 28, 2009, 4 pages.
O'Connor R.A., et al., "Translational Mini-Review Series on Th17 Cells: CD4+ T Helper Cells: Functional Plasticity and Differential Sensitivity to Regulatory T Cell-mediated Regulation," Clinical and Experimental Immunology, Feb. 2010, vol. 159 (2), 11 pages.
Oda K., et al., "A Comprehensive Map of the Toll-like Receptor Signaling Network," Molecular Systems Biology, Feb. 2006, vol. 2 (1), 20 pages.
Oh J.W., et al., "CD4 T-Helper Cells Engineered to Produce IL-10 Prevent Allergen-induced Airway Hyperreactivity and Inflammation," Journal of Allergy and Clinical Immunology, Sep. 2002, vol. 110 (3), 9 pages.
Ohno N., et al., "Comparison of the Immunopharmacological Activities of Triple and Single-helical Schizophyllan in Mice," Biological and Pharmaceutical Bulletin, Sep. 1995, vol. 18 (9), 7 pages.
Ohno N., et al., "Enhancement of LPS Triggered TNF-alpha (Tumor Necrosis Factor-alpha) Production by (1-->3)-beta-D-glucans in Mice," Biological and Pharmaceutical Bulletin, Jan. 1995, vol. 18 (1), 9 pages.
Onderdonk A.B., et al., "Evidence for T Cell-dependent Immunity to Bacteroides fragilis in an Intraabdominal Abscess Model," The Journal of Clinical Investigation, Jan. 1982, vol. 69 (1), 8 pages.
Onderdonk A.B., et al., "The Capsular Polysaccharide of Bacteroides Fragilis as a Virulence Factor: Comparison of the Pathogenic Potential of Encapsulated and Unencapsulated Strains," The Journal of Infectious Diseases, Jul. 1977, vol. 136 (1), 4 pages.
Ozenci V., et al., "Multiple Sclerosis: Levels of Interleukin-10-Secreting Blood Mononuclear Cells Are Low in Untreated Patients but Augmented During Interferon-beta-1 b Treatment," Scandinavian Journal of Immunology, May 1999, vol. 49 (5), 8 pages.
Pantosti A., et al "Bacteroides Fragilis Strains Express Multiple Capsular Polysaccharides," Journal of Clinical Microbiology, Jul. 1993, vol. 31 (7), 6 pages.
Paoletti L.C., et al., "Effects of Chain Length on the Immunogenicity in Rabbits of Group B *Streptococcus* Type III Oligosaccharide-tetanus Toxoid Conjugates," The Journal of Clinical Investigation, Jan. 1992, vol. 89 (1), 7 pages.
Paoletti L.C., et al., "Neonatal Mouse Protection Against Infection With Multiple Group B Streptococcal (GBS) Serotypes by Maternal Immunization With a Tetravalent GBS Polysaccharide-Tetanus Toxoid Conjugate Vaccine," Infection and Immunity, Aug. 1994, vol. 62 (8), 8 pages.
Park C.S., et al., "Interleukin-2 and Soluble Interleukin-2 Receptor in Bronchoalveolar Lavage Fluid From Patients With Bronchial Asthma," Chest, Aug. 1994, vol. 106 (2), 7 pages.
Pavliak V., et al., "Structural Elucidation of the Capsular Polysaccharide of Bacteroides Fragilis Strain 23745M1," Carbohydrate Research, Oct. 1995, vol. 275 (2), 9 pages.
Perumal et al., "Protective Effect of Interleukin-2 on Experimental Intra-abdominal Abscess Development Due to Bacteriodes Fragilis," Clinical Research, 1990, vol. 38 (2), 1 pages.
Polyethylene Glycols (PEGs), accessed Mar. 7, 2005, http://www.mindfully.org/Piastic/Polymers/Polyethylene-Glyeols-PEGs.htm, 1 page.

(56) References Cited

OTHER PUBLICATIONS

Popovic N., et al., "Inhibition of Autoimmune Encephalomyelitis by a Tetracycline," Annals of Neurology, Feb. 2002, vol. 51 (2), 9 pages.
Prieto P.A., et al., "A New Ganglioside in Human Meconium Detected by Antiserum Against the Human Milk Sialyloligosaccharide, LS-Tetrasaccharide B," Archives of Biochemistry and Biophysics, Aug. 1985, vol. 241 (1), 9 pages.
Progress in Autoimmune Diseases Research, National Institutes of Health, The Autoimmune Diseases Coordinating Committee, Report to Congress. U.S. Department of Health and Human Service, Mar. 2005, 146 pages.
Rabe K.F., et al., "Pharmacological Treatment of Asthma Today," The European Respiratory Journal, Supplement, Dec. 2001, vol. 34, 7 pages.
Raetz C.R., et al., "Lipopolysaccharide Endotoxins," Annual Review of Biochemistry, 2002, vol. 71, 57 pages.
Ranua J., et al., "Serum Iga, Igg, and Igm Concentrations in Patients With Epilepsy and Matched Controls: a Cohort-based Cross-sectional Study," Epilepsy Behavior, Mar. 2005, vol. 6 (2), 5 pages.
Restriction Requirement for U.S. Appl. No. 13/112,725, dated Mar. 18, 2013, 7 pages.
Riesenfeld J., et al., "Biosynthesis of Heparin. ASSAY and Properties of the Microsomal N-acetyl-D-glucosaminyl N-Deacetylase," The Journal of Biological Chemistry, Feb. 10, 1980, vol. 255(3), 8 pages.
Roncarolo M.G., et al., "Type 1 T Regulatory Cells," Immunological Reviews, Aug. 2001, vol. 182, 12 pages.
Rypens F., et al., "Percutaneous Drainage of Abdominal Abscesses in Pediatric Crohn's Disease," American Journal of Roentgenology, Feb. 2007, vol. 188(2), 7 pages.
Salyers A.A., et al., "Conjugative Transposons: An Unusual and Diverse Set of Integrated Gene Transfer Elements," Microbiological Reviews, Dec. 1995, vol. 59(4), 12 pages.
Schembri M.A., et al., "Orientation-Dependent Enhancement by H-NS of the Activity of the Type 1 Fimbrial Phase Switch Promoter in *Escherichia coli*," Molecular Genetics and Genomics, Aug. 1998, vol. 259(3), 9 pages.
Schlegel P.G., et al., "A Synthetic Random Basic Copolymer with Promiscuous Binding to Class II Major Histocompatibility Complex Molecules Inhibits T-cell Proliferative Responses to Major and Minor Histocompatibility Antigens in Vitro and Confers the Capacity to Prevent Murine Graft-Versus-Host Disease in Vivo," Proceedings of the National Academy of Sciences of the United States of America, May 14, 1996, vol. 93(10), 6 pages.
Schneider G., et al., "De novo design of molecular architectures by evolutionary assembly of drug-derived buildingblock," Journal of Computer-Aided Molecular Design, Jul. 2000, vol. 14(5), 9 pages.
Segal T., et al., "Severe Insulin Resistance Secondary to Insulin Antibodies: Successful Treatment with the Immunosuppressant MMF," Pediatric Diabetes, Jun. 2008, vol. 9(3 Pt 1), 7 pages.
Sellin L.C., et al., "Conformational Analysis of a Toxic Peptide From Trimeresurus Wagleri Which Blocks the Nicotinic Acetylcholine Receptor," Biophysical Journal, Jan. 1996, vol. 70 (1), 11 pages.
Shaklee P.N., et al., "Hydrazinolysis of Heparin and Other Glycosaminoglycans," The Biochemical Journal, Jan. 1984, vol. 217 (1), 11 pages.
Shapiro M.E., et al., "Cellular Control of Abscess Formation: Role of T Cells in the Regulation of Abscesses Formed in Response to Bacteroides Fragilis," Journal of Immunology, Jul. 1986, vol. 137 (1), 6 pages.
Shapiro M.E., et al., "Cellular Immunity to Bacteroides Fragilis Capsular Polysaccharide," The Journal of Experimental Medicine, Apr. 1982, vol. 155 (4), 10 pages.
Sharpe A.H., et al., "The B7-CD28 Superfamily," Nature Review Immunology, Feb. 2002, vol. 2 (2), 11 pages.
Shevach E.M., "CD4+CD25+Suppressor T Cells: More Questions Than Answers," Nature Reviews Immunology, Jun. 2002, vol. 2 (6), 12 pages.
Simmons C.G., et al., "Synthesis and Membrane Permeability of PNA-peptide Conjugates," Bioorganic & Medicinal Chemistry Letters, Dec. 1997, vol. 7 (23), 8 pages.
Smith S.G., et al., "Functional Analysis of the Fime Integrase of *Escherichia coli* K-12: Isolation of Mutant Derivatives with Altered DNA Inversion Preferences," Molecular Microbiology, Dec. 1999, vol. 34 (5), 15 pages.
Stein K.E., "Thymus-Independent and Thymus-dependent Responses to Polysaccharide Antigens," The Journal of Infectious Diseases, Jun. 1992, vol. 165 (Suppl 1), 6 pages.
Stromnes I.M., et al., "Passive Induction of Experimental Allergic Encephalomyelitis," Nature Protocols, 2006, vol. 1 (4), 10 pages.
Stumhofer, J. S. et al. "Interleukins 27 and 6 induce STAT3-mediated T cell production of interleukin 10" Nature immunology, 2007, 10 pages.
Supplementary European Search Report for EP Application No. EP2217250, dated Dec. 8, 2010, 2 pagese.
Suri-Payer E., et al., "CD4+CD25+ T Cells Inhibit Both the Induction and Effector Function of Autoreactive T Cells and Represent a Unique Lineage of Immunoregulatory Cells," Journal of Immunology, Feb. 1998, vol. 160 (3), 7 pages.
Szu S.C., et al., "Relation Between Structure and Immunologic Properties of the Vi Capsular Polysaccharide," Infection and Immunity, Dec. 1991, vol. 59 (12), 7 pages.
Tang C., et al., "Th Type 1-stimulating Activity of Lung Macrophages Inhibits Th2-mediated Allergic Airway Inflammation by an IFN-gamma-dependent Mechanism," Journal of Immunology, Feb. 2001, vol. 166 (3), 11 pages.
Taylor R.L., et al., "Stoichiometric Depolymerization of Polyuronides and Glycosaminoglycuronans to Monosaccharides Following Reduction of Their Carbodiimide-activated Carboxyl Groups," Biochemistry, Apr. 1972, vol. 11 (8), 6 pages.
Teitelbaum D., et al., "Immunomodulation of Experimental Autoimmune Encephalomyelitis by Oral Administration of Copolymer 1," Proceedings of the National Academy of Sciences of the United States of America, Mar. 1999, vol. 96 (7), 6 pages.
Teitelbaum D., et al., "Specific Inhibition of the T-cell Response to Myelin Basic Protein by the Synthetic Copolymer Cop 1," Proceedings of the National Academy of Sciences of the United States of America, Dec. 1988, vol. 85 (24), 5 pages.
Teitelbaum D., et al., "Unprimed Spleen Cell Populations Recognize Macrophage-bound Antigen with Opposite Net Electric Charge," Proceedings of the National Academy of Sciences of the United States of America, Apr. 1977, vol. 74 (4), 4 pages.
Teitelbaum D., et al., "Synthetic Copolymer 1 Inhibits Human T-cell Lines Specific for Myelin Basic Protein," Proceedings of the National Academy of Sciences of the United States of America, Jan. 1992, vol. 89 (1), 5 pages.
The Merck Index. Eleventh Edition 1989, 2 pages.
Thomas k.S., et al., "Randomised Controlled Trial of Short Bursts of a Potent Topical Corticosteroid Versus Prolonged Use of a Mild Preparation for Children with Mild or Moderate Atopic Eczema," BMJ, Mar. 2002, vol. 324 (7640), 7 pages.
Torisu M., et al., "Significant Prolongat ion of Disease-Free Period Gained by Oral Polysaccharide K (PSK) Administration after Curative Surgical Operation of Colorectal Cancer," Cancer Immunology, Immunotherapy, vol. 31(5), Sep. 1, 1990, 8 pages, XP055323922.
Tournoy K.G., et al., "Endogenous Interleukin-10 Suppresses Allergen-induced Airway Inflammation and Nonspecific Airway Responsiveness," Clinical and Experimental Allergy, Jun. 2000, vol. 30 (6), 9 pages.
Tzianabos A.O., et al., "Bacterial Structure and Functional Relation to Abscess Formation," Infectious Agents and Disease, Oct. 1994, vol. 3 (5), 10 pages.
Tzianabos A.O., et al., "Effect of Surgical Adhesion Reduction Devices on the Propagation of Experimental Intra-abdominal Infection," Archives of Surgery, Nov. 1999, vol. 134 (11), 6 pages.
Tzianabos A.O., et al., "IL-2 Mediates Protection Against Abscess Formation in an Experimental Model of Sepsis," Journal of Immunology, Jul. 1999, vol. 163 (2), 6 pages.
Tzianabos A.O., et al., "Polysaccharide Immunomodulators as Therapeutic Agents: Structural Aspects and Biologic Function," Clinical Microbiology Reviews, Oct. 2000, vol. 13 (4), 11 pages.

(56) References Cited

OTHER PUBLICATIONS

Tzianabos A.O., et al., "Polysaccharide-mediated Protection Against Abscess Formation in Experimental Intra-abdominal Sepsis," The Journal of Clinical Investigation, Dec. 1995, vol. 96 (6), 5 pages.
Tzianabos A.O., et al., "Protection Against Experimental Intraabdominal Sepsis by Two Polysaccharide Immunomodulators," The Journal of Infectious Diseases, Jul. 1998, vol. 178 (1), 7 pages.
Tzianabos A.O., et al., "Structural Rationale for the Modulation of Abscess Formation by *Staphylococcus aureus* Capsular Polysaccharides," Proceedings of the National Academy of Sciences of the United States of America, Jul. 2001, vol. 98 (16), 6 pages.
Tzianabos A.O., et al., "Structure-function Relationships for Polysaccharide-induced Intra-abdominal Abscesses," Infection and Immunity, Aug. 1994, vol. 62 (8), 4 pages.
Tzianabos et al., "Characteristics of bacterial polysaccharides that activate T cells," The International Carbohydrate Symposium XVII, Jul. 21, 1994, 1 page.
Tzianabos et al., "T Cell Activation by Zwitterionic Polysaccharides and Peptide Mimetics Prevents Intrabdominal Abscess Formation," Abstracts of the 99th General Meeting of the American Society for Microbiology, Chicago, US, May 30-Jun. 3, 1999, Jun. 28, 1999, 1 page.
Ulcerative Colitis From the National Institutes of Health [online], Retrieved from the internet: http://digestive.niddk.nih.gov/ddiseases/pubs/colitis/UlcerativeColitis_508.pdf, on Nov. 9, 2012, 8 pages.
Van Scott M.R., et al., "IL-10 Reduces Th2 Cytokine Production and Eosinophilia But Augments Airway Reactivity in Allergic Mice," American Journal of Physiology—Lung Cellular and Molecular Physiology, Apr. 2000, vol. 278 (4), 8 pages.
Vann W.F., et al., "The Structure of the Capsular Polysaccharide (K5 Antigen) of Urinary-Tract-Infective *Escherichia coli* 010:K5:H4. A Polymer Similar to Desulfo-Heparin," European Journal of Biochemistry, May 1981, vol. 116 (2), 6 pages.
VAXA, Systemic Lupus Erythematosus (SLE), Damaging and Unpredictable. http://www.vaxa.com/arthritis-systemic-lupus-erythematosus.cfm, accessed on Apr. 3, 2008, 2 pages.
Velez., et al., "Type I Streptococcuspneumoniae carbohydrateUtilizes a Nitric Oxide and MGC 11-Dependent Pathway for Antigen Presentation," Immunology, 2008, vol. 127, 10 pages.
Verdu E.F., et al., "Oral Administration of Antigens from Intestinal Flora Anaerobic Bacteria Reduces the Severity of Experimental Acute Colitis in BALB/c Mice," Clinical & Experimental Immunology, Apr. 2000, vol. 120 (1), 5 pages.
Vinderola G., et al., "Effects of the Oral Administration of the Exopolysaccharide Produced by Lactobacillus Kefiranofaciens on the Gut Mucosal Immunity," Cytokine, Dec. 2006, vol. 36 (5-6), 7 pages.
Viret J.F., et al., "Molecular Cloning and Characterization of the Genetic Determinants That Express the Complete Shigella Serotype D (*Shigella sonnei*) Lipopolysaccharide in Heterologous Live Attenuated Vaccine Strains," Molecular Microbiology, Jan. 1993, vol. 7 (2), 14 pages.
Wagner M.A., et al., "Use of Reporter Cells to Study Endogenous Retinoid Sources in Embryonic Tissues," Methods in Enzymology, 1997, vol. 282, 10 pages.
Wang et al., "Structure Characterization of an Abscessogenic Capsular Polysaccharide from Bacteriodes Fragilis by NMR Spectroscopy," XIX International Conference of NMR in Biological Systems, Florence, Italy, Aug. 20-25, 2000, 1 page, Abstract only.
Wang X., et al., "Lipopolysaccharide: Biosynthetic Pathway and Structure Modification," Progress in Lipid Research, Apr. 2010, vol. 49 (2), 11 pages.
Wang Y., et al., "Ozonolysis for Selectively Depolymerizing Polysaccharides Containing β-d-Aldosidic Linkages," Proceedings of the National Academy of Sciences, Jun. 1998, vol. 95 (12), 11 pages.
Wang Y., et al., "Structural Basis of the Abscess-Modulating Polysaccharide A2 from Bacteroides Fragilis," Proceedings of the National Academy of Sciences, Dec. 2000, vol. 97 (25), 6 pages.
Ward E., et al., "The Nucleotide Sequence of the tnpA Gene of Tn21," Nucleic Acids Research, Feb. 1987, vol. 15 (4), 8 pages.

Wehr H., et al., "Anti-Low-Density Lipoprotein Antibodies in Alcoholics Without and With Liver Disease and in Social Drinkers," Alcohol and Alcoholism, Jan.-Feb. 1997, vol. 32 (1), 8 pages.
Weinacht et al., "Phase Variation of the Capsular Polysaccharides of Bacteroides Fragilis is Dictated by Site-specific Recombinases," General Meeting of the American Society for Microbiology, May 19-23, 2002, 1 page (abstract only).
Wessels M.R., et al., "Structural Determination and Immunochemical Characterization of the Type V Group B *Streptococcus* Capsular Polysaccharide," Biological Chemistry, Apr. 1991, vol. 266 (11), 6 pages.
Wessels M.R., et al., "Structure and Immunochemistry of an Oligosaccharide Repeating Unit of the Capsular Polysaccharide of Type III Group B *Streptococcus*. A Revised Structure for the Type III Group B Streptococcal Polysaccharide Antigen," Biological Chemistry, Jun. 1987, vol. 262 (17), 6 pages.
Wexler H.M, "Bacteroides: The Good, the Bad, and the Nitty-Gritty," Clinical Microbiology Reviews, Oct. 2007, vol. 20 (4), 29 pages.
Whitfield C, "Biosynthesis and Assembly of Capsular Polysaccharides in *Escherichia coli*," Annual Review of Biochemistry, 2006, vol. 75, 33 pages.
Wegandt H., et al., "Carbohydrate Components of Extraneuronal Gangliosides from Bovine and Human Spleen, and Bovine Kidney," European Journal of Biochemistry, Aug. 1970, vol. 15 (2), 7 pages.
Wrtz S., et al., "Mouse Models of Inflammatory Bowel Disease," Advanced Drug Delivery Reviews, Sep. 2007, vol. 59 (11), 11 pages.
Woessner R., et al., "Long-Term Antibiotic Treatment with Roxithromycin in Patients with Multiple Sclerosis," Infection, Dec. 2006, vol. 34 (6), 3 pages.
Wujek J.R., et al., "A Carbohydrate Polymer That Effectively Prevents Epidural Fibrosis at Laminectomy Sites in the Rat," Experimental Neurology, Nov. 1991, vol. 114 (2), 11 pages.
Xu J., et al., "A Genomic View of the Human-Bacteroides Thetaiotaomicron Symbiosis," Science, Mar. 2003, vol. 299 (5615), 3 pages.
Yokoyama M., et al., "Adhesion Behavior of Rat Lymphocytes to Poly(ether)-Poly(amino acid) Block and Graft Copolymers," Biomedical Materials Research, Sep. 1986, vol. 20 (7), 14 pages.
Yoshii E., et al., "Cytotoxic Effects of Acrylates and Methacrylates: Relationships of Monomer Structures and Cytotoxicity," Journal of Biomedical Materials Research, Dec. 1997, vol. 37 (4), 8 pages.
Zabad R.K., et al., "The Clinical Response to Minocycline in Multiple Sclerosis Is Accompanied by Beneficial Immune Changes: a Pilot Study," Multiple Sclerosis, May 2007, vol. 13 (4), 10 pages.
Zaleznik D.F., et al., "A Soluble Suppressor T Cell Factor Protects Against Experimental Intraabdominal Abscesses," Clinical Investigation, Mar. 1985, vol. 75 (3), 5 pages.
Zhang., et al., "Degradation of Wood Polysaccharide Model CompoundsDuring Ozone Treatment," Pulp and Paper Science, Jan. 1997, vol. 23 (1), 5 pages.
Zhang X., et al., "Calcium, Vitamin D and Colorectal Cancer Chemoprevention," Bailliere's Best Practice and Research, Clinical Gastroenterology, vol. 25(4), Jan. 1, 2011, 10 pages.
Zhang X., et al., "IL-10 is Involved in the Suppression of Experimental Autoimmune Encephalomyelitis by CD25+CD4+ Regulatory T Cells," International Immunology, Feb. 2004, vol. 16 (2), 8 pages.
Zhao H., et al., "In Vivo Phase Variation of MR/P Fimbrial Gene Expression in Proteus Mirabilis Infecting the Urinary Tract," Molecular Microbiology, Mar. 1997, vol. 23 (5), 11 pages.
Zhu P., et al., "Oral Administration of Type-ii Collagen Peptide 250-270 Suppresses Specific Cellular and Humoral Immune Response in Collagen-induced Arthritis," Clinical Immunology, Jan. 2007, vol. 122 (1), 10 pages.
Final Office Action for U.S. Appl. No. 15/179,810, filed Jun. 10, 2016 on behalf of California Institute of Technology dated Jun. 28, 2019 13 pages.
International Search Report for International Application No. PCT/US2016/037044 filed Jun. 10, 2016 on behalf of California Institute of Technology, dated Sep. 22, 2016. 4 pages.

(56) References Cited

OTHER PUBLICATIONS

Kalka-Moll, W.M. et al., "Immunochemical and Biological Characterization of Three Capsular Polysaccharides from a Single Bacteroides Fragilis Strain", Infection and Immunity, vol. 69, No. 4, pp. 2339-2344, (2001).
Mazmanian, S.K. et al., "An Immunomodulatory Molecule of Symbiotic Bacteria Directs Maturation of the Host Immune System", Cell, vol. 122(1), pp. 107-118, (2005).
Non-Final Office Action for U.S. Appl. No. 15/179,810, filed Jun. 10, 2016 on behalf of California Institute of Technology, dated Sep. 28, 2018. 11 pages.
Notification of Reason for Refusal for Japanese Patent Application No. 2013511406, dated Apr. 12, 2016, 7 pages (Japanese original + English translation).
Notification of Reasons for Refusal for Japanese Patent Application No. 2013511406, dated May 12, 2015, 6 pages (Japanese original+ English translation).
Office Action for Japanese Patent Application No. JP2015116494, dated Jul. 12, 2016, 8 pages (Japanese original+ English translation).
Reid, R.R., et al., "Endotoxin shock in antibody-deficient mice: unraveling the role of natural antibody and complement in the clearance of lipopolysaccharide," Journal of immunology,1997. 159(2): p. 970-5. Abstract Only.
Restriction Requirement for U.S. Appl. No. 15/179,810, filed Jun. 10, 2016 on behalf of California Institute of Technology, dated May 4, 2018. 10 pages.
"Abscess" from Wikipedia, dated May 9, 2015 (6 pages) https://en.wikipedia.org/Wiki/Abscess.
International Preliminary Report on Patentability for International Application No. PCT/US2016/037044 filed Jun. 10, 2016 on behalf of California Institute of Technology, dated Dec. 12, 2017. 9 pages (English Only).
"Sepsis" from National Institute of General Medical Sciences, dated Jan. 2018 (3 pages).
Taconic Farms, "Swiss Webster" mouse, available at https://www.taconic.com/mouse-model/swiss-webster; 9 total pages; obtained Jun. 26, 2019 (Year: 2019).
Tzianabos, A. O., "Polysaccharide Immunomodulators as Therapeutic Agents: Structural Aspects and Biologic Function", Clinical Microbiology Reviews, Oct. 2000, p. 523-533.
Tzianabos, A.O. et al., "Protection Against Experimental Intraabdominal Sepsis by Two Polysaccharide Immunomodulators", The Journal of Infectious Diseases, vol. 178, pp. 200-206, (1998).
Vazquez, M. et al., International Journal of Clinical Pharmacology and Therapeutics, "Therapeutic drug monitoring of vancomycin in severe sepsis and septic shock", 2008, vol. 46, pp. 140-145. doi: 10.5414/CPP46140. (Year: 2008) Abstract Only.
Wang, Y. et al., "Structural Basis of the Abscess-Modulating Polysaccharide A2 From Bacteroides Fragillis", Proc. Natl. Acad. Sci. U.S.A., vol. 97, No. 25, pp. 13478-13483, (2000).
Written Opinion for International Application No. PCT/US2016/037044 filed Jun. 10, 2016 on behalf of California Institute of Technology, dated Sep. 22, 2016. 8 pages.
Zouali, M. et al., "Marginal Zone B-Cells, A Gatekeeper of Innate Immunity", Frontiers in Immunology, vol. 2, Article 63, 10 pages, (2011).
Dohi T. et al., "Type 1 and 2 T helper cell-mediated colitis" Current Opinion in Gastroenterology, 2006, pp. 651-657.
Final Office Action for U.S. Appl. No. 14/274,607, filed May 9, 2014 on behalf of California Institute of Technology, dated Jun. 15, 2018 14 pages.
Final Office Action for U.S. Appl. No. 14/660,827, filed Mar. 17, 2015 on behalf of California Institute of Technology, dated Dec. 28, 2017 25 pages.
Final Office Action for U.S. Appl. No. 14/803,598, filed Jul. 20, 2015 on behalf of California Institute of Technology, dated Oct. 22, 2018 12 pages.
Harrington L. et al., "Interleukin 17-producing CD4+ effector T cells develop via a lineage distinct from the T helper type 1 and 2 lineages" Nature Immunology,Nov. 2005, vol. 6, No. 11, pp. 1123-1132, 10 pages.
Kayama H. et al., "Regulation of intestinal homeostasis by innate and adaptive immunity" International Immunology, vol. 24, No. 11, pp. 673-680,Sep. 2012, 8 pages.
Nagaraj S. et al., "Reciprocal Relationship between Myeloid-Derived Suppressor Cells and T Cells" Journal of Immunology, Dec. 2013, pp. 17-23 8 pages.
Non-Final Office Action for U.S. Appl. No. 14/274,607, filed May 9, 2014 on behalf of California Institute of Technology, dated Aug. 9, 2017 19 pages.
Non-Final Office Action for U.S. Appl. No. 14/274,607, filed May 9, 2014 on behalf of California Institute of Technology, dated Jan. 18, 2019 19 pages.
Non-Final Office Action for U.S. Appl. No. 14/631,760, filed Feb. 25, 2015 on behalf of California Institute of Technology, dated Mar. 16, 2017 14 pages.
Non-Final Office Action for U.S. Appl. No. 14/660,827, filed Mar. 17, 2015 on behalf of California Institute of Technology, dated Dec. 27, 2018 18 pages.
Non-Final Office Action for U.S. Appl. No. 14/660,827, filed Mar. 17, 2015 on behalf of California Institute of Technology, dated Mar. 22, 2017 13 pages.
Non-Final Office Action for U.S. Appl. No. 14/803,598, filed Jul. 20, 2015 on behalf of California Institute of Technology, dated May 11, 2018. 9 pages.
Non-Final Office Action for U.S. Appl. No. 15/011,151, filed Jan. 29, 2016 on behalf of California Institute of Technology, dated Aug. 30, 2017 20 pages.
Non-Final Office Action for U.S. Appl. No. 15/706,604, filed Sep. 15, 2017 on behalf of California Institute of Technology, dated Mar. 5, 2019 18 pages.
Pillay J. et al., "Immune suppression by neutrophils and granulocytic myeloid-derived suppressor cells: similarities and differences" Cellular and Molecular Life Sciences, Feb. 2013, pp. 3813-3827 15 pages.
Restriction Requirement for U.S. Appl. No. 14/803,598, filed Jul. 20, 2015 on behalf of California Institute of Technology, dated Feb. 14, 2018. 7 pages.
Rodgers et al., "Prescribing an antibiotic? Pair it with probiotics", The Journal of Family Practice, Mar. 2013, pp. 148-150, vol. 62, No. 3, Frontline Medical Communications, Parsippany, NJ.
Stenvinkel P. et al., "IL-10, IL-6, and TNF-a: Central factors in the altered cytokine network of uremia—The good, the bad, and the ugly" Kidney International, vol. 67, pp. 1216-1233.
Wingate K. et al., "25-Hydroxyvitamin D Concentrations in Children with Crohn's Disease Supplemented with Either 2000 or 400 IU Daily for 6 Months: A Randomized Controlled Study" The Journal of Pediatrics, vol. 164, No. 4,Apr. 2014, pp. 860-865 6 pages.
Yang J. et al., "Targeting Th17 cells in autoimmune diseases" Cell Press, vol. 35, No. 10,Oct. 2014, pp. 493-500 8 pages.
Communication from EPO Examining Division for EP 08847489.5, 11 pages, dated May 3, 2017.
Communication from EPO Examining Division for EP 11766746.9, 5 pages, dated Sep. 23, 2014.
Communication from EPO Examining Division for EP 11766746.9, 4 pages, dated Nov. 10, 2015.
Communication from EPO Examining Division for EP 11766746.9, 7 pages, dated Feb. 1, 2018.
Communication from EPO Examining Division for EP 14795204.8, 4 pages, dated Jan. 24, 2018.
Communication from EPO Examining Division for EP 14795204.8, 3 pages, dated Jan. 18, 2019.
Non-Final Office Action for U.S. Appl. No. 16/514,796, filed Jul. 17, 2019 on behalf of California Institute of Technology, dated Nov. 7, 2019 10 pages.
Pragani R. et al. "Total Synthesis of the Bacteroides fragilis Zwitterionic Polysaccharide A1 Repeating Unit." J Am Chem Soc, 2011, 133, 1, 102-107; publication date: Dec 10, 2010. Abstract only.

(56) References Cited

OTHER PUBLICATIONS

Amidon et al., "Proposed New USP General Information Chapter, Excipient Performance <1059>", Pharmacopeia forum, Nov.-Dec. 2007, pp. 1311-1323, vol. 33(6), The United States Pharmacopeia Convention, Rockville, MD.
Decision of Refusal dated Feb. 26, 2016 in Japanese Patent Application No. 2013-503958.
Decision of Refusal dated Nov. 27, 2018 in Japanese Patent Application No. 2016-513092.
Examination Report dated Jan. 24, 2018 in European Patent Application No. 147952048.
Examination Report dated Jan. 18, 2019 in European Patent Application No. 147952048.
Final Office Action dated Sep. 16, 2020 in U.S. Appl. No. 16/386,522.
Non-Final Office Action dated Jun. 8, 2020 in U.S. Appl. No. 16/386,522.
Non-Final Office Action dated Aug. 7, 2020 in U.S. Appl. No. 16/151,793.
Non-Final Office Action dated Sep. 1, 2020 in U.S. Appl. No. 16/562,358.
Notice of Allowance dated May 1, 2020 in U.S. Appl. No. 16/514,796.
Notice of Allowance dated Jul. 5, 2018 in European Patent Application No. 11766746.9.
Notice of Allowance dated Sep. 16, 2016 in Japanese Patent Application No. 2013-503958.
Notice of Allowance dated Jan. 9, 2018 in Japanese Patent Application No. 2016-126806.
Notice of Allowance dated Feb. 10, 2020 in Japanese Patent Application No. 2018-020819.
Notice of Reasons for Refusal dated Apr. 25, 2017 in Japanese Patent Application No. 2016-126806.
Notice of Reasons for Refusal dated Dec. 14, 2018 in Japanese Patent Application No. 2018-020819.
Notice of Reasons for Refusal dated Oct. 10, 2019 in Japanese Patent Application No. 2018-020819.
Notice of Reasons for Refusal dated Mar. 23, 2015 in Japanese Patent Application No. 2013-503958.
Notice of Reasons for Refusal dated Dec. 28, 2017 in Japanese Patent Application No. 2016-513092.
Notice of Reasons for Refusal dated Mar. 18, 2020 in Japanese Patent Application No. 2019-061261.

\* cited by examiner

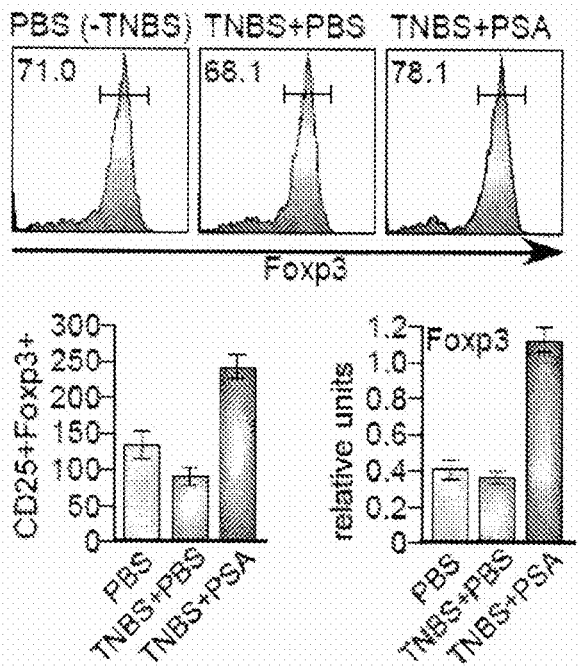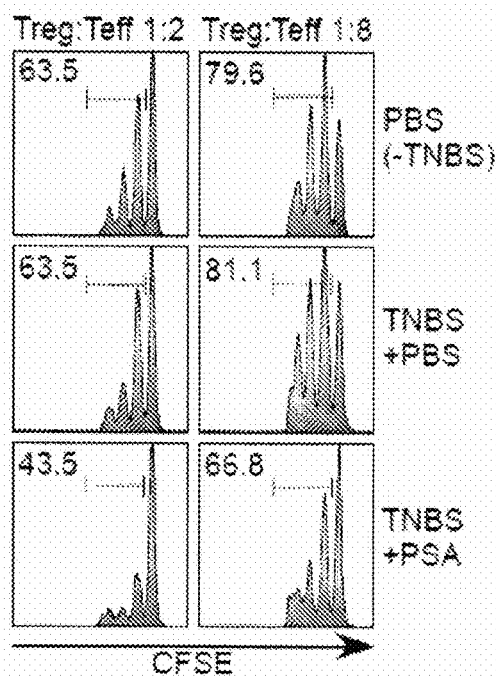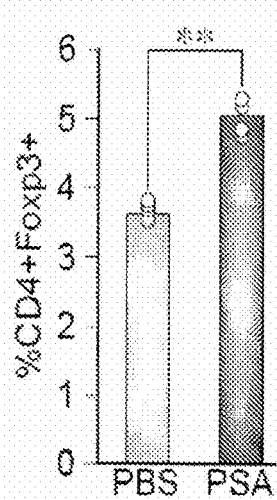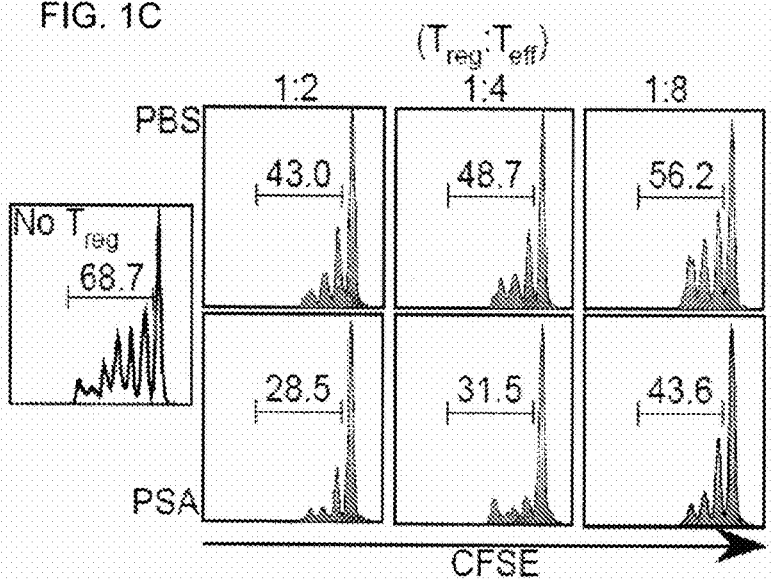

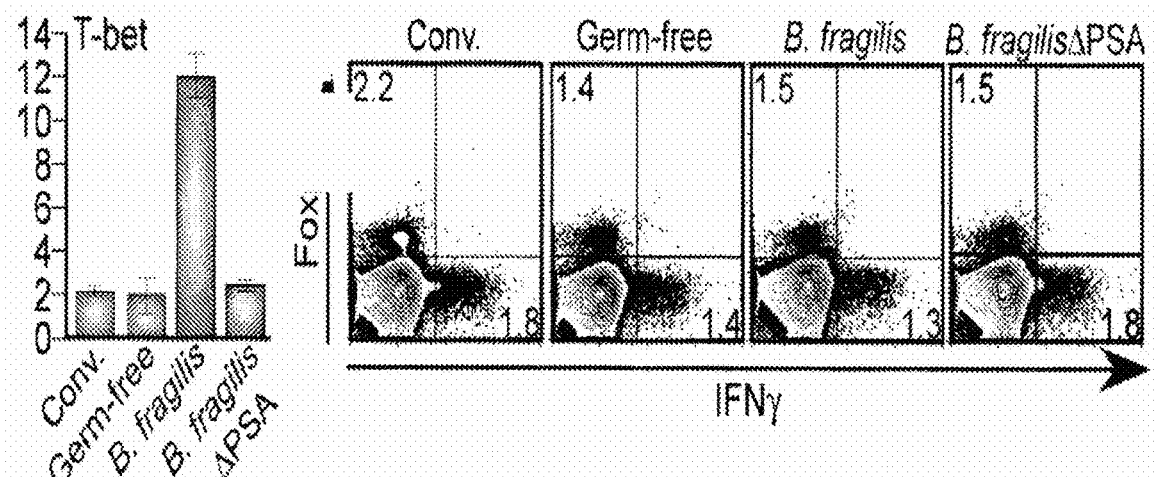
FIG. 8C
FIG. 8D
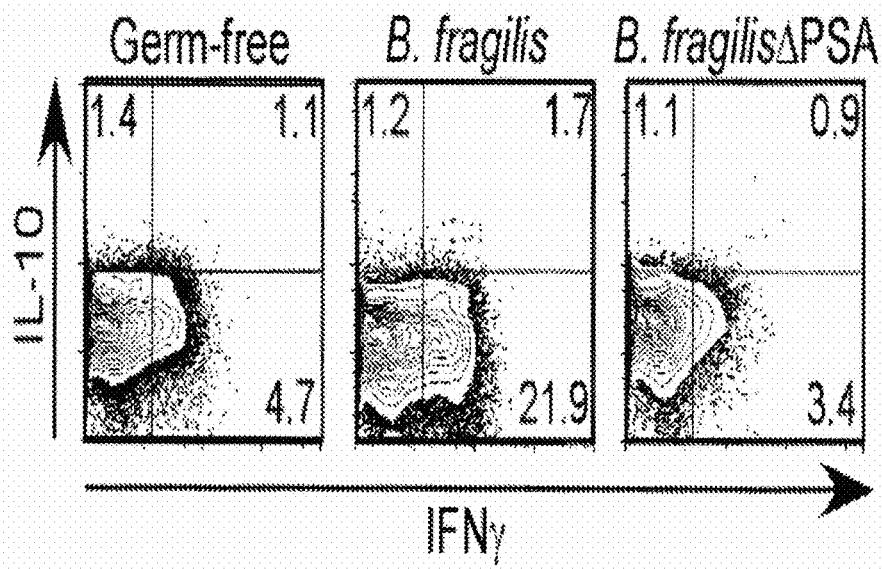
Fig. 8E

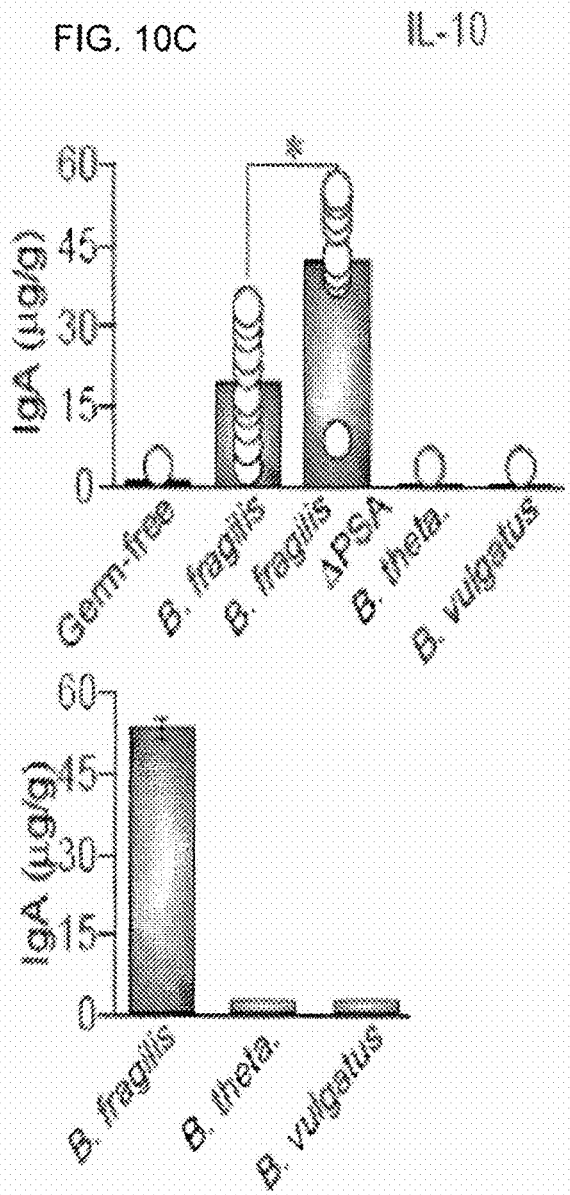
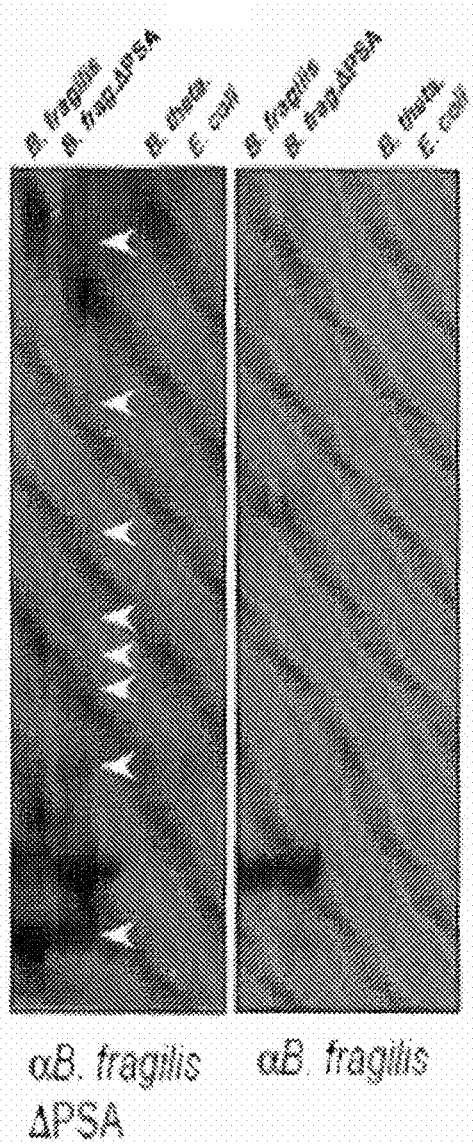
FIG. 10C
FIG. 10D
FIG. 10E

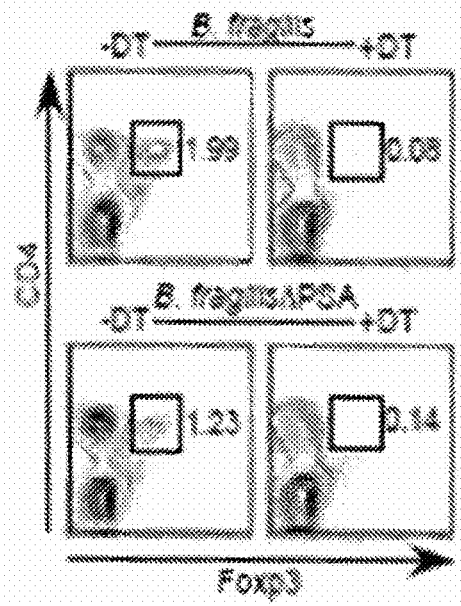
FIG. 14A
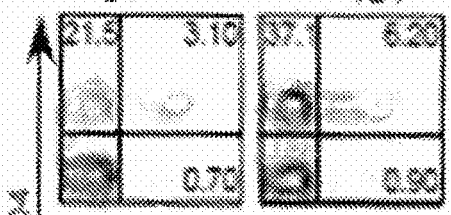
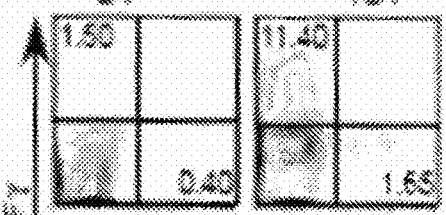
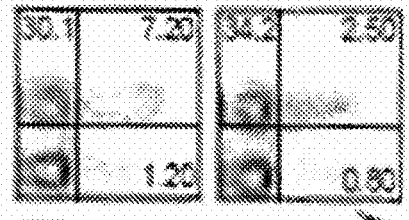
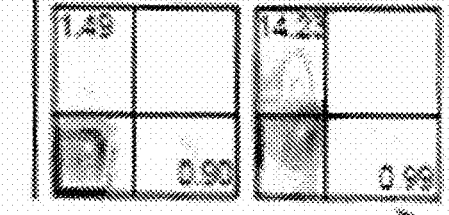
FIG. 14B　　　　　　FIG. 14C

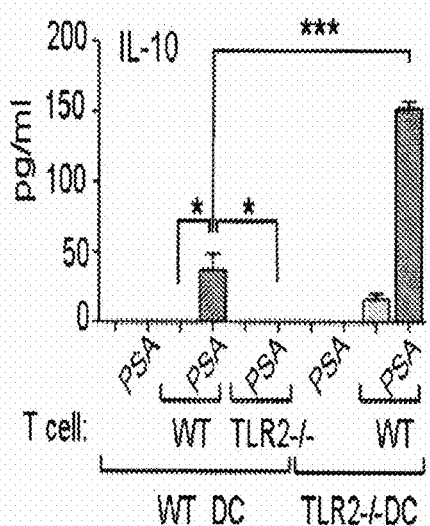
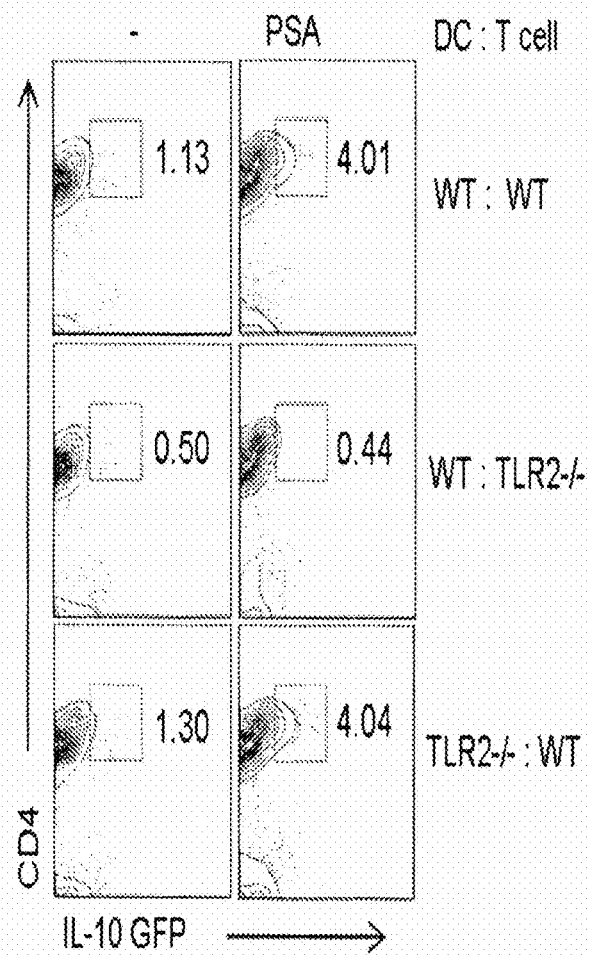
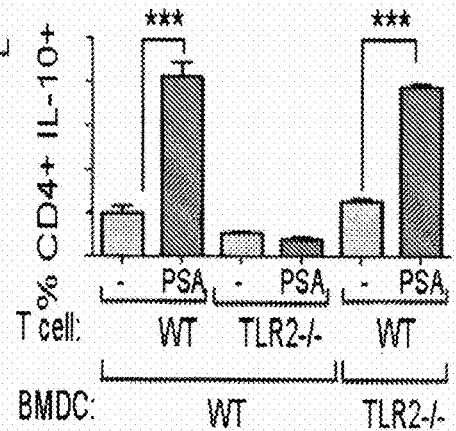
FIG. 17A
FIG. 17B
FIG. 17C
FIG. 17D

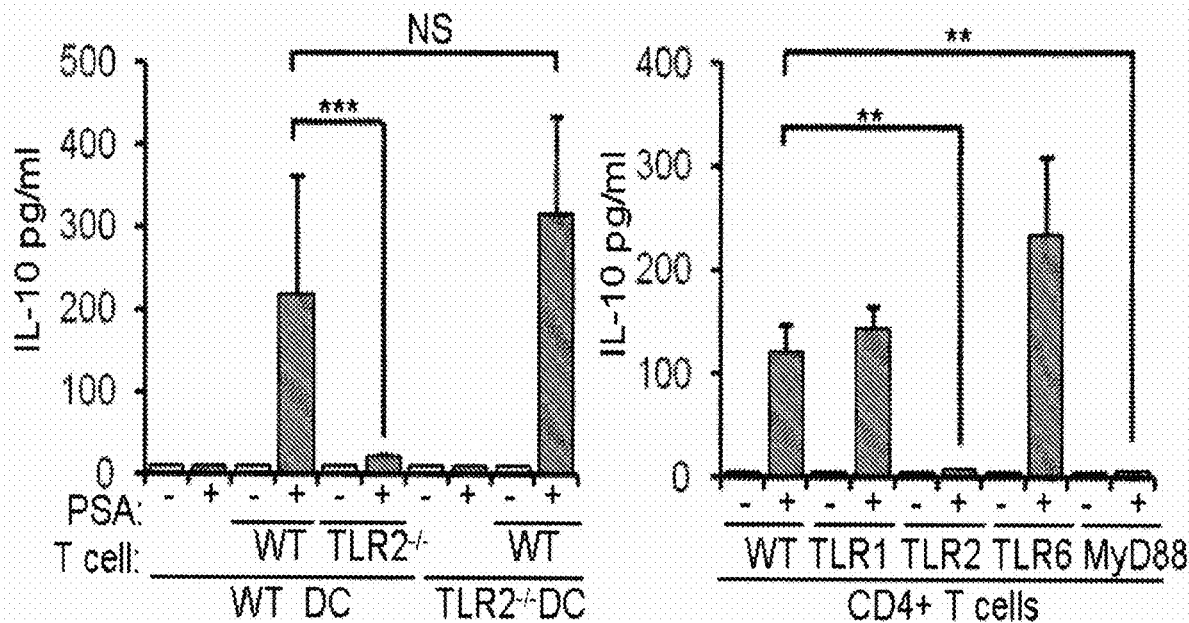
FIG. 18A
FIG. 18B
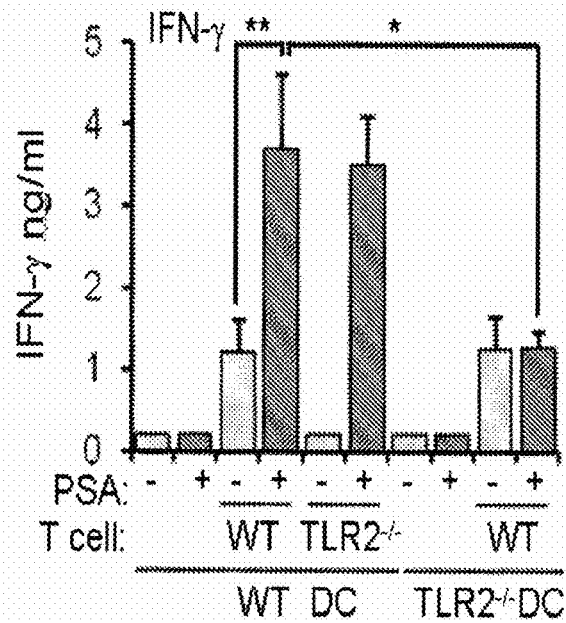
FIG. 18C

ANTIGEN SPECIFIC TREGS AND RELATED COMPOSITIONS, METHODS AND SYSTEMS

CROSS REFERENCE TO RELATED APPLICATIONS

This application is a Continuation of U.S. application Ser. No. 13/112,725 filed on May 20, 2011, which in turn, claims the benefit of U.S. Provisional application No. 61/346,837, filed on May 20, 2010, each of which is incorporated by reference herein in its entirety.

STATEMENT OF GOVERNMENT GRANT

This invention was made with government support under Grant No. DK078938 awarded by the National Institutes of Health. The government has certain rights in the invention.

The ASCII text file submitted via EFS-WEB entitled "P552-USC-sequence-listing_ST25", created on Apr. 27, 2017, is hereby incorporated by reference in its entirety.

FIELD OF THE INVENTION

The present disclosure relates to the immune system, and, in particular, to antigen specific regulatory T cells and related compositions, methods and systems.

BACKGROUND OF THE INVENTION

Regulatory T cells (Tregs) belong to a group of white blood cells known as lymphocytes, and play a central role in cell-mediated immunity. In particular, regulatory T helper cells (also known as suppressor T cells or Th cells) are a sub-group of lymphocytes (a type of white blood cell or leukocyte) that plays an important role in establishing and maximizing the capabilities of the immune system and in particular in activating and directing other immune cells.

In particular, Tregs are a component of the immune system that suppresses biological activities of other cells associated to an immune response. More particularly, Tregs can secrete immunosuppressive cytokines TGF-beta and Interleukin 10, and are known to be able to limit or suppress inflammation.

T cells and in particular Tregs are involved in antigen specific immune response. In particular, antigen specific Tregs are functional to regulate and resolve an inflammatory response triggered by antigen specific inflammatory T cells for clearance of antigens. Antigen specificity of the inflammatory and regulatory response is paramount to avoid immune-compromising the host.

SUMMARY

Provided herein are antigen specific regulatory T cells and related compositions, methods and systems that in several embodiments are able to inhibit an antigen specific pro-inflammatory cell mediated and/or humoral immune response in vitro and/or in vivo.

According to a first aspect, a method to generate an antigen specific anti-inflammatory regulatory T cell is described. The method comprises contacting a T cell with a zwitterionic polysaccharide conjugated to the antigen for a time and under condition to generate an antigen specific regulatory T cell capable of inhibiting a pro-inflammatory response against the antigen.

According to a second aspect, a method to generate an antigen specific antiinflammatory regulatory T cell is described. The method comprises contacting a T cell with an engineered *Bacteroides fragilis* herein described for a time and under condition to generate an antigen specific regulatory T cell capable of inhibiting an inflammatory response against the antigen.

According to a third aspect a method to generate an antigen specific anti-inflammatory regulatory T cell is described. The method comprises contacting an antigen presenting cell with a zwitterionic polysaccharide conjugated to the antigen for a time and under condition to generate an antigen presenting cell presenting the antigen. The method further comprises contacting the antigen presenting cell presenting the antigen with a T cell for a time and under condition to generate an antigen specific regulatory T cell capable of inhibiting an inflammatory response against the antigen.

According to fourth aspect, a method to generate an antigen specific anti-inflammatory regulatory T cell is described. The method comprises contacting an antigen presenting cell with an engineered *Bacteroides fragilis* herein described for a time and under condition to generate an antigen presenting cell presenting the antigen. The method further comprises contacting the antigen presenting cell presenting the antigen with a regulatory T cell to generate an antigen specific regulatory T cell capable of inhibiting an inflammatory response against the antigen.

According to a fifth aspect, an engineered *Bacteroides fragilis* is described, wherein the engineered *Bacteroides fragilis* expresses a heterologous antigen conjugated with polysaccharide A.

According to a sixth aspect, an antigen specific anti-inflammatory regulatory T cell is described that is obtainable by a method to generate an antigen specific anti-inflammatory regulatory T cell herein described.

According to a seventh aspect, a system to generate antigen specific, anti-inflammatory regulatory T cells is described. The system comprises at least two selected from the group consisting of an engineered *Bacteroides fragilis* expressing an antigen, a zwitterionic polysaccharide, a T cell, and an antigen.

According to an eight aspect, a method of inhibiting antigen specific inflammation in an individual is described. The method comprises treating the individual with a zwitterionic polysaccharide conjugated to an antigen for a time and under conditions to induce an antigen specific regulatory T cell in the individual specific for the antigen.

According to a ninth aspect, a method of inhibiting antigen specific inflammation in an individual is described, the method comprises treating the individual with an engineered *Bacteroides fragilis* expressing an antigen conjugated to polysaccharide A for a time and under condition to generate an antigen specific regulatory T cell capable of inhibiting a pro-inflammatory response against the antigen.

According to a tenth aspect, a method of treating a condition of an individual associated with an antigen specific pro-inflammatory T-cell response in the individual is described. The method comprises treating the individual with an antigen specific anti-inflammatory T cell, wherein the antigen specific anti-inflammatory T cell is specific for the specific antigen of the antigen specific pro-inflammatory T cell response.

The Tregs herein described and related compositions methods and systems can be used in connection with medical, pharmaceutical, veterinary applications as well as fundamental biological studies and various applications, identifiable by a skilled person upon reading of the present disclosure, wherein generating antigen specific Tregs is desirable.

In one embodiment, a method to generate an antigen specific anti-inflammatory regulatory T cell is provided, the method comprising contacting either: a) a T cell with a zwitterionic polysaccharide conjugated to the antigen for a time and under condition to generate an antigen specific regulatory T cell that is capable of inhibiting a pro-inflammatory response against the antigen; or b) an antigen presenting cell with a zwitterionic polysaccharide conjugated to the antigen for a time and under condition to generate an antigen specific regulatory T cell that is capable of inhibiting a pro-inflammatory response against the antigen.

In another embodiment, a method to generate an antigen specific anti-inflammatory regulatory T cell is provided, the method comprising contacting either: a) a T cell with a zwitterionic polysaccharide for a time and under condition to generate an antigen specific regulatory T cell that is capable of inhibiting a pro-inflammatory response against the antigen; or b) an antigen presenting cell with a zwitterionic polysaccharide for a time and under condition to generate an antigen specific regulatory T cell The details of one or more embodiments of the disclosure are set forth in the accompanying drawings and the description below. Other features, objects, an advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and example sections, serve to explain the principles and implementations of the disclosure.

FIGS. 1A-G show that PSA functionally expands suppressive regulatory T cells. FIG. 1A shows flow cytometry (FC) analysis results of the percentage of Foxp3+ cells within the CD4+CD25+ population in the MLNs of Balb/c mice treated with PSA or PBS every other day for 6 days prior to the rectal instillation of TNBS. These data are representative of three independent experiments. FIG. 1B shows FC analysis results of mice that were treated as in FIG. 1A, MLN cells were counted and absolute numbers of CD4+CD25+Foxp3+ cells determined ($\times 10^3$). Numbers represent the average of four mice in a single experiment. FIG. 1C shows Foxp3 expression in MLNs. RNA was extracted from the MLNs of mice treated as in FIG. 1A and Foxp3 expression normalized to $\beta$-actin expression in the total lymph node. FIG. 1D shows analysis of CD4+CD25+ cells purified from the MLNs of colitic PBS or PSA treated mice and incubated with CFSE pulsed CD4+CD25− in an in vitro suppression assay. Numbers indicate the percentage of cells undergoing at least one cellular division at 2 different ratios of effector T cells (Teff) and regulatory T cells (Treg). These data are representative of two independent experiments. FIG. 1E shows FC analysis of Foxp3+ T cells from C57Bl/6 mice that were orally fed PSA every other day for 2 weeks. MLNs were extracted and the percentage of Foxp3+ T cells within the CD4+CD25+ compartment was analyzed by FC. Each symbol represents an individual mouse. The p value was determined by a two-tailed students t test. FIG. 1F shows the results of an in vitro suppression assay of CD4+CD25+ cells that were purified from the MLN of PBS or PSA treated mice and incubated with CFSE pulsed CD4+CD25− cells, mitomycin C treated CD4− cells and purified $\alpha$-CD3. Numbers indicate the percentage of proliferating cells at 3 ratios of Teff to Treg cells. FIG. 1G shows that PSA induces expansion of Tregs, but not B cells, during experimental colitis. The MLN of TNBS mice were analyzed for the presence of B cells by FACS.

In FIG. 2A, C57Bl/6 Foxp3-GFP mice were orally treated with purified PSA every other day for 6 days. The MLNs were extracted and the CD4+Foxp3+ or the CD4+Foxp3− T cells were purified by cell sorting based on ±GFP expression. RNA was extracted from these cell types and used for qRT-PCR. These data are representative of three independent experiments. FIG. 2B shows that purified PSA treatment upregulates Foxp3 expression during TNBS colitis.

FIG. 3A shows RT-PCR results showing that mono-association of germ-free animals with B. fragilis increases the total amount of IL-10 within the colon. RNA was extracted from the colon of indicated mice and IL-10 was assayed by qRT-PCR. Each symbol represents an individual mouse. Statistical significant was determined by a two-tailed student's t test. FIG. 3B shows results of C57Bl/6 germ-free mice irradiated and reconstituted with bone marrow from Foxp3-GFP mice. Mice were subsequently colonized with B. fragilis strains (as indicated) for 8-10 weeks. Lamina propria lymphocytes were purified from the colon and re-stimulated with PMA/ionomycin in the presence of brefeldin A. Each symbol indicates an individual mouse. These data are representative of two independent experiments. FIG. 3C shows FC analysis of cells extracted and treated as in FIG. 3B. The percentage from individual mice of CD4+Foxp3+IL10+ cells in the colonic lamina propria was determined by FC. FIG. 3D shows analysis of genes known to be associated with regulatory T cells. CD4+Foxp3-GFP+ T cells were purified from the MLNs by cell sorting. RNA was extracted and used for qRT-PCR to analyze genes. FIG. 3E shows DNA extracted from fecal samples of mice that were irradiated and reconstituted with bone marrow to ensure sterility. Universal 16s primers demonstrate that germfree mice remained sterile throughout the experiment.

FIG. 4A shows FC analysis of lamina propria lymphocytes (LPL) extracted from the colons of indicated animals (n=4/group) and re-stimulated with PMA and ionomycin in the presence of brefeldin A for 5 hours. Cells were stained with $\alpha$-CD4 and $\alpha$-IL-17A and analyzed by FC. These data are representative of four independent experiments. FIG. 4B shows ELISA of IL-17A in colonic LPLs re-stimulated with PMA and ionomycin for 24 hours. The relative expression of IL-17A (FIG. 4C) and ROR$\gamma$T(FIG. 4D) from qRT-PCR is shown. CD4+Foxp3-GFP− cells were cell sorted and RNA was extracted and qRT-PCR performed. FIG. 4E shows ELISA of CD4+ T cells purified from the MLNs of indicated mice and incubated with plate bound a-CD3 alone (white boxes) or in addition to TGF-$\beta$ (light grey boxes) or with TGF-$\beta$ and IL-6 (dark grey boxes). Cells were incubated for 72 hours and IL-17A was determined by ELISA. These data are representative of three independent experiments. FIG. 4F shows ELISA analysis of intestinal cells from B. fragilis$\Delta$PSA colonized animals producing increased levels of IL-17 specifically to molecules from B. fragilis. T cell-depleted splenocytes were incubated for 24 hours with the indicated strains of heat-killed bacteria. Before use, APCs were washed to remove un-internalized bacteria. Colonic lamina propria lymphocytes from mice mono-associated with either *B. fragilis* (white boxes) or *B. fragilis*ΔPSA (grey boxes) were incubated with bacterial-pulsed APCs for 72 hours. The amount of secreted IL-17A from these cultures was analyzed by ELISA. These data are representative of three independent experiments.

FIGS. 5A and 5B show FACS analysis of CD4+Foxp3-(GFP–) cells. CD4+Foxp3-(GFP–) cells were FACS sorted from conventionally-colonized animals and equal numbers of cells were transferred into GF Rag-/-recipients that were either left germ-free, or colonized by *B. fragilis* or *B. fragilis*ΔPSA. MLNs were analyzed for CD4+GFP+ (Foxp3) T cells. Cells in FIG. 5B were re-stimulated in vitro and stained for a-CD4 and a-IL-10. Cells are gated on CD4+ T cells. ** p value of <0.01. FIG. 5C demonstrates that Tregs isolated from the MLNs of *B. fragilis* colonized animals induce TGF-β in a PSA dependent manner.

FIG. 6A and FIG. 6B shows FC analysis of CD4+Foxp3+ T cells. Mice were colonized as indicated and the percentage of CD4+Foxp3+ T cells was determined by flow cytometry. Each symbol represents an individual mouse. There are no significant differences between any groups as determined by a student's t test. Each symbol represents an individual animal in FIG. 6B. FIG. 6C shows the percentage of CD4+IL-17A+ cells within the lamina propria. The percentage of CD4+IL-17A+ cells within the lamina propria is represented from individual mice from the same experiment. These data are representative of four independent experiments.

FIG. 7A-7B shows percentage of CD4+Foxp3+ cells from TLR2-/- mice. TLR2-/- mice were fed PSA. MLNs were extracted and analyzed for the percentage of CD4+Foxp3+ cells. Each symbol represents the percentage of CD4+Foxp3+ from an individual mouse. NS, not significant. FIG. 7B shows qRT-PCR analysis of CD4+CD25hi+ and CD4+CD25– T cell populations that were FACS sorted from MLNs of PSA-fed TLR2–/mice. IL-10 levels were analyzed by qRT-PCR. Light and dark bars indicate IL-10 levels in PBS or PSA treated animals, respectively. Results are representative of two independent trials. FIG. 7C shows that RORγT expression is elevated in the colons of mice mono-associated with *B. fragilis*ΔPSA. Colons were homogenized and RNA extracted from the tissue. Expression levels of RORγT were assayed by q-PCR.

FIG. 8A shows results of an in vitro suppression assay of CD4+ CD25+ Tregs. Mice were fed PBS or PSA and CD4+CD25+ Tregs were purified from indicated animals and titrated into the assay. Each bar represents one round of division. *indicates statistical significance p<0.05. FIG. 8B shows quantitative RT-PCR results of MLNs. Foxp3-GFP animals were gavaged with purified PSA. MLNs were extracted and CD4+Foxp3–(GFP–) and CD4+Foxp3+(GFP+) cell populations were sorted and RNA collected. Dark bars represent transcript levels from mice treated with PSA. Lighter bars represent data acquired from animals treated with PBS. Quantitative real time PCR was performed to determine the levels of ICOS, perforin and Tbet in each sample. FIG. 8C shows level of expression of T-bet by q-PCR. CD4+Foxp3+ cells were purified from the indicated mice and the level of expression of T-bet analyzed. Cells from the MLNs (FIG. 8D) or splenocytes (FIG. 8E) from indicated animals were re-stimulated for 5 hours with PMA and Ionomycin in the presence of Brefeldin A. Cells were subsequently stained for indicated cytokines. Plots are gated on live CD4+ cells. FIG. 8F shows dysregulation of luminal ATP is not the mechanism by which elevated levels of colonic IL-17 are induced in *B. fragilis*ΔPSA animals.

FIG. 9A shows IL-17A by ELISA in CD4+ T cells. CD4+ T cells were purified from the MLNs of indicated mice (colonized with different bacteria as illustrated in the figure) and incubated with plate bound a-CD3 alone (white boxes) or in addition to TGF-β (light grey boxes) or with TGF-b and IL-6 (dark grey boxes). Error bars represent SD of triplicate samples, and are representative of three independent experiments.

FIGS. 10A-E show that adaptive immune responses to *B. fragilis* are antigen-specific. FIG. 10A shows secretion of IL-17A by ELISA in colonic LPLS. Colonic LPLs were isolated from either *B. fragilis* or *B. fragilis*ΔPSA colonized animals and incubated with APCs pulsed with the bacterial species indicated. Error bars represent SD of triplicate samples. These data are representative of three independent trials. FIG. 10B shows IL-17A and IL-10 production. Germ-free animals were irradiated and reconstituted with bone marrow from Foxp3-GFP animals. Animals were subsequently left germ-free or colonized with *B. fragilis* or *B. fragilis*ΔPSA. CD4+Foxp3-(GFP–) cells were purified by FACS from these animal groups and transferred into Rag-/- recipients mono-associated with *B. fragilis*ΔPSA. 10 days post-transfer, cells were assayed for IL-17A and IL-10 production. These data are representative of two independent experiments. FIG. 10C shows ELISA analysis of *B. fragilis*-specific IgA. Each symbol represents an individual mouse. Samples were normalized to the weight of the colonic content collected. * p value of <0.05. FIG. 10D shows ELISA analysis of IgA reactivity toward either *B. fragilis, B. thetaiotaomicron*, or *B. vulgatus* antigens. Error bars represent SD of triplicate samples. FIG. 10E shows total cell extracts from indicated bacteria separated on a polyacrylamide gel and transferred to PVDF membrane. Blots were probed with antibody preparations from either *B. fragilis* or *B. fragilis*ΔPSA colonized animals, and immune-reactive species were detected by anti-mouse IgA secondary linked to HRP. White arrows indicate antigenic bands that are reactive with IgA isolated from *B. fragilis*ΔPSA colonized animals but not from wild-type *B. fragilis*. These data are representative of two independent experiments.

FIG. 11 graphically depicts the results of an ELISA of the total amount of IgA in the colonic contents. Values were normalized to the weight of the colonic contents isolated. Each symbol represents IgA within the colon of a single mouse.

FIG. 12A shows ELISA analysis of the levels of *B. fragilis* and *B. vulgatus* reactive IgA. Germ-free mice were co-colonized with equal numbers of *B. vulgatus* and either wt *B. fragilis* or *B. fragilis*ΔPSA and levels of *B. fragilis* and *B. vulgatus* reactive IgA were analyzed by ELISA. Data are represented as bacterial specific IgA binding normalized to weight of colonic content. Error bars are SD from individual mice (n=4). Data are representative of two independent experiments. FIG. 12B show FC analysis of IgA reactivity to *B. fragilis* or *B. vulgates*. FIG. 12C shows *B. fragilis*-specific IgA (left panel) or total IgA (right panel). Germ-free mice were co-colonized with wild-type *B. fragilis*, *B. fragilis*ΔPSA, or both *B. fragilis* and *B. fragilis*ΔPSA. ** p value of <0.01. NS, not significant. Data are representative of three independent experiments. FIG. 12D and FIG. 13F show FC analysis of IgA reactivity to *B. fragilis* following co-colonization between wild-type *B. fragilis* and *B. fragilis*ΔPSA. FIG. 12E shows a titration curve (IgA dilutions of 1:6, 1:4, and 1:2 from left to right). Error bars in FIG. 12E represent the SD within groups (n=4). Data are representative of three independent trials.

FIG. 13A shows the colonization of mice. Feces were collected from animals that were co-associated with wt *B. fragilis* and *B. fragilis*ΔPSA. Wild-type *B. fragilis* carried a plasmid that conferred chloramphenicol resistance. Both strains colonized mice equally. FIG. 13B shows colony forming units of each bacterial strain tested. Feces were collected from animals that were co-colonized with wild-type *B. fragilis* and *B. vulgatus* and colony forming units of each bacterial strain was determined by plating. FIG. 13C shows reactivity to *B. vulgatus* antigens using ELISA. Soluble colonic contents were taken from either germ-free, *B. fragilis* or *B. vulgatus* mono-associated mice and tested for reactivity to *B. vulgatus* antigens.

FIGS. 14A-E show that Foxp3+ Tregs are required for suppression of adaptive inflammatory responses during mutualism. FIG. 14A shows FC plots of MLNs from animals showing ablation of CD4+Foxp3+ Tregs by DT treatment. FIG. 14B and FIG. 14C show IL-17A and IFNγ production by CD4+ T cells. Rag-deficient or irradiated germ-free mice were reconstituted with bone marrow from Foxp3-DTR animals, and colonized with either *B. fragilis* or *B. fragilis*ΔPSA. Mice were treated with diphtheria toxin (DT) and LP or MLNs were assayed for IL-17A and IFNγ production by CD4+ T cells. Numbers indicate percentage of cells within each quadrant. These data are representative of three independent experiments. FIG. 14D shows qRT-PCR analysis of expression of IL17A. Colonic LPLs from indicated mice were isolated and re-stimulated for 24 hours with plate-bound α-CD3 and α-CD28. FIG. 14E shows *B. fragilis*-specific reactivity by ELISA. IgA was collected from the ileum and colon of indicated animals, and *B. fragilis*-specific reactivity was determined using a standard ELISA protocol. These data are representative of three independent experiments.

FIG. 15A depicts the percentage of CD4+IFNγ+ T cells in DT treated animals mono-associated with either *B. fragilis* or *B. fragilis*ΔPSA. As showing in FIG. 15B, IgA is not significantly different in the absence of Tregs. Intestinal contents were extracted as described in materials and methods and total IgA measured by ELISA. In FIG. 15C PSA specific IgA was measured by ELISA and relative units normalized to weight of colonic contents.

FIG. 16A shows OMVs produced by wild-type *B. fragilis* and *B. fragilis*ΔPSA that were detected by transmission electron microscopy of EDL (electron dense layer)-enriched *B. fragilis*. FIG. 16B shows an immunoblot analysis of whole cell (WC) and outer membrane vesicles (OMV) extracts from wild-type and PSA-mutant bacteria. FIG. 16C shows immunogold labeling of purified OMVs, stained with anti-PSA and anti-IgG-colloidal gold conjugate (5 nm), analyzed by electron microscopy.

FIGS. 17A-D PSA elicit IL-10 production through TLR2 signaling directly on a T cell. FIG. 17A shows results of experiments where splenic cdllc+ cells were enriched from the spleens of WT or TLR2−/− animals and co-cultured with CD4+ T cells purified from the spleens of either WT or TLR2−/− animals along with anti-CD3 and TGF-β in the presence or absence of PSA for a total of 5 days. Supernatants were collected from cultures and IL-10 was assayed by ELISA. Cultures were performed in triplicate. * indicates p values less than 0.05 and * indicates p values less than 0.005. These results are representative of three independent experiments. FIGS. 17B-17C show results of experiments where Bone marrow derived dendritic cells (BMDCs) from either IL-10− GFP (as WT control) or TLR2−/− animals were cocultured with CD4+ T cells purified from the spleens of IL-10-GFP (as WT control) or TLR2−/− animals cultured with anti-CD3 and TGF-β in the absence (−) or presence of purified PSA. The percentage of CD4 cells expressing GFP (IL-10) is shown. * indicates a p valued less than 0.01. FIG. 17C shows results of experiments where cells were cultured as in FIG. 17A and the amount of secreted IFNγ was assayed by ELISA. * indicates p values less than 0.05. NS indicates not significant.

FIGS. 18A-C PSA can directly signal through TLR2 on a T cell in the absence of APC and this does not require TLR 1 or TLR6. FIGS. 18A-18B show results of experiments where CD4+ T cells were isolated from wild-type (WT) TLR1−/−, TLR2−/−, TLR6−/−, or CD14−/− animals. Cells were stimulated with anti-CD3 in the presence of TGF-β with (+) or without (−) PSA. in vitro cultures were allowed to incubate for 4 days and IL-10 secreted into the supernatant was measured by ELISA. * indicates statistical significance p=<0.05. Cell cultures were 94% pure. FIG. 18C shows results of experiments where BMDCs were made from WT, TLR2−/−, animals and incubated with purified CD4+ T cells from WT mice. Cultures were stimulated with anti-CD3 and TGF-0 and incubated for 4 days. Secreted IFN-γ were assayed from these cultures by ELISA. * indicates statistical significance p=<0.05:

FIG. 19A shows results of experiments performed with PSA. PAM3CysK and FSL1 on CD4+Foxp3− T cells. PAM3CysK is a known TLR1/TLR2 ligand while FSL1 is a known TLR2/6 ligand. PSA's ability to induce IL-10 from a highly purified population (greater than 99% pure CD4+Foxp3-T cells) of non-Treg cells was assayed. Non-Treg cells (CD4+Foxp3−) were FACs sorted from Foxp3-GFP animals and stimulated with anti-CD3 in the presence of TGF-β and indicated TLR ligands PSA or PAM3CysK. Secretion of IL-10 was assayed by ELISA.

FIG. 20 shows results of experiments where CD4+Foxp3+ T cells were FACS sorted from Foxp3-GFP mice and the ability of PSA to enhance the suppressive capacity of a Treg was measured. Purified CD4+CD25− cells were CFSE pulsed and incubated with Tregs cells in the presence of BMDCs and anti-CD3 Cell proliferation was assayed by dilution of CFSE.

FIG. 21 shows results of experiments where Faes sorted CD4+Foxp3+ T cells from WT or TLR2−/− animals were stimulated with anti-CD3 in the presence of TGF-β and incubated with and without PSA. After 5 days of culture, RNA was extracted from cells and IL10 was assayed by qRT-PCR.

DETAILED DESCRIPTION

Figure 1G:
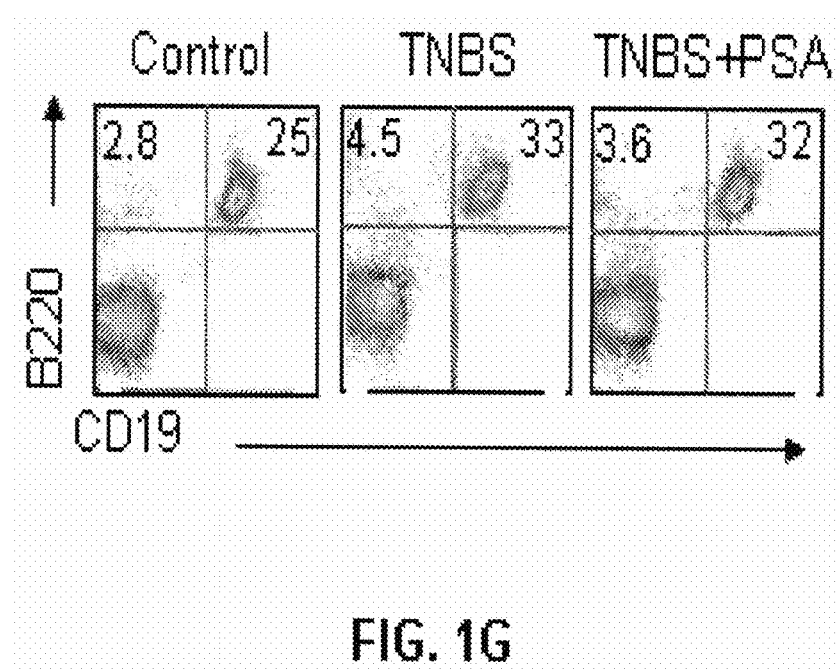

Provided herein are methods and systems for generating antigen specific regulatory T cells.

The term "T cell" as used herein indicates a type of white blood cell or leukocyte including different cell types identifiable by a skilled person and that include various subtypes of T helper cells or Th cells. The term "regulatory T cells" or "T reg(s)" indicates suppressor Th cells, i.e. Th cells that suppress activation of the immune system and thereby maintain immune system homeostasis and tolerance to self-antigens. In particular a T regulatory cell can be functionally defined as a CD4+ T cell type that is capable of suppressing immune responses such as T helper cell proliferation. Biomarkers that can be used for detection and/or identification of a Treg comprise Foxp3, IL-10, IL-35, CTLA-4, GITR, CD25, TGF, perforin, granzyme B in any combination. In general, Tregs are crucial for the maintenance of immunological tolerance. Their major role in individuals, such as humans, is to inhibit T cell-mediated immunity toward the end of an immune reaction and to suppress auto-reactive T cells that escaped the process of negative selection in the thymus. Two major classes of CD4+ regulatory T cells have been described, including the naturally occurring Treg cells and the adaptive Treg cells. Naturally occurring Tregs are Tregs that develop based on 'signals' from the host or organism that produces the cells (i.e., individuals such as mice and humans). Adaptive or inducible Tregs are derived from naive T cells that receive signals from the environment (such as gut bacteria for Tregs).

The term "antigen specific regulatory T cell" as used herein indicates a Treg that is capable of suppressing activation of an immune response for a specific antigen, thus inducing tolerance for the specific antigen. In particular, an antigen specific Treg is typically a Treg that is capable of suppressing the T helper cell proliferation and inflammation that is specific for the antigen.

The term "antigen" as used herein indicates a molecule recognized by the immune system. Exemplary antigens comprise molecules that bind specifically to an antibody, and any molecule or molecular fragment that can be bound by a major histocompatibility complex (MHC) and presented to a T-cell receptor. "Self" antigens are usually tolerated by the immune system; whereas "Non-self" antigens are identified as intruders and attacked by the immune system. Biomarkers that can be used to identify and/or detect antigen specific Treg typically comprise surface expression of CD25, GITR, CTLA-4, or nuclear expression of Foxp3. Such 'antigens' can be those associated with various conditions as found in paragraphs [0096] to [0108] below.

The terms "inhibiting", "inhibit" or "suppressing", as used herein indicate the activity of decreasing the biological reaction or process. Accordingly, a substance "inhibits" a certain biological reaction or process if it is capable of decreasing that biological reaction or process by interfering with said reaction or process. For example, a substance can inhibit a certain biological reaction or process by reducing or suppressing the activity of another substance (e.g. an enzyme) associated to the biological reaction or process, e.g. by binding, (in some cases specifically), said other substance. Inhibition of the biological reaction or process can be detected by detection of an analyte associated with the biological reaction or process. The term "detect" or "detection" as used herein indicates the determination of the existence, presence or fact of an analyte or related signal in a limited portion of space, including but not limited to a sample, a reaction mixture, a molecular complex and a substrate. A detection is "quantitative" when it refers, relates to, or involves the measurement of quantity or amount of the analyte or related signal (also referred as quantitation), which includes but is not limited to any analysis designed to determine the amounts or proportions of the analyte or related signal. A detection is "qualitative" when it refers, relates to, or involves identification of a quality or kind of the analyte or related signal in terms of relative abundance to another analyte or related signal, which is not quantified.

In one embodiment, "inhibiting", "inhibit" or "suppressing" can mean any value or amount of the reaction, activity or substance being measured that is lower than values found in controls, as determined by those of skill in the art. For example, a control sample where the reaction is devoid of PSA or the OMV vesicle and/or the antigen; or a control with only control media (i.e. PBS control). Similarly, an "increase" or "increasing" activity or amount is any value or amount of the reaction, activity or substance being measured that is greater than values found in controls, as determined by those of skill in the art.

The terms "Inflammatory response", "pro-inflammatory response" and "inflammation" as used herein indicate the complex biological response of vascular tissues of an individual to harmful stimuli, such as pathogens, damaged cells, or irritants, and includes secretion of cytokines and more particularly of pro-inflammatory cytokine, i.e. cytokines which are produced predominantly by activated immune cells such as microglia and are involved in the amplification of inflammatory reactions. Exemplary pro-inflammatory cytokines include but are not limited to IL-1, IL-6, TNF-a, IL-17, IL21, IL23, and TGF-β. Exemplary inflammations include acute inflammation and chronic inflammation. The wording "acute inflammation" as used herein indicates a short-term process characterized by the classic signs of inflammation (swelling, redness, pain, heat, and loss of function) due to the infiltration of the tissues by plasma and leukocytes. An acute inflammation typically occurs as long as the injurious stimulus is present and ceases once the stimulus has been removed, broken down, or walled off by scarring (fibrosis). The wording "chronic inflammation" as used herein indicates a condition characterized by concurrent active inflammation, tissue destruction, and attempts at repair. Chronic inflammation is not characterized by the classic signs of acute inflammation listed above. Instead, chronically inflamed tissue is characterized by the infiltration of mononuclear immune cells (monocytes, macrophages, lymphocytes, and plasma cells), tissue destruction, and attempts at healing, which include angiogenesis and fibrosis. An inflammation can be inhibited in the sense of the present disclosure by affecting and in particular inhibiting anyone of the events that form the complex biological response associated with an inflammation in an individual.

An "antigen specific inflammatory response" indicates an inflammatory response specific to a particular antigen, which typically involves activation of antigen specific inflammatory T cell or effector Th cells that secrete cytokines, proteins or peptides that stimulate or interact with other leukocytes, including Th cells. Exemplary inflammatory T cells comprise Th1, Th2 and Th17.

As will be expanded in other parts of this application, any antigen of interest can be located or expressed within or on the same vesicle as the polysaccharide (or PSA), and the vesicle then used to contact with either a T cell and/or antigen presenting cell, thereby resulting in the generation of antigen specific Tregs capable of inhibiting an antigen specific inflammatory response.

In another embodiment, any antigen of interest can be conjugated to polysaccharides (or PSA) while the polysaccharides are actually located on the vesicle (i.e. cell surface conjugation), and then the vesicle used to contact with either a T cell and/or antigen presenting cell; thereby resulting in the generation of antigen specific Tregs capable of inhibiting an antigen specific inflammatory response.

In yet another embodiment, any antigen of interest can be conjugated to purified natural or synthesized polysaccharides (or PSA) (i.e. not within or part of the vesicle), and then the conjugated polysaccharide-antigen complex used to contact with either a T cell and/or antigen presenting cell; thereby resulting in the generation of antigen specific Tregs capable of inhibiting an antigen specific inflammatory response.

In one embodiment, T cells, T reg or antigen presenting cells can be purified from an individual or patient, and then these patient specific cells used to contact with a zwitterionic polysaccharide conjugated to the antigen for a time in vitro and under condition to generate an antigen specific regulatory T cell that is capable of inhibiting a pro-inflammatory response against the antigen.

In another embodiment, the above mentioned generated patient specific antigen specific regulatory T cell of paragraph [0055] can be injected back into the same individual/patient, who is suffering from a condition i.e. an inflammatory condition or who has received a graft.

In an embodiment, an antigen specific anti-inflammatory regulatory T cell is generated by contacting an antigen presenting cell (APC) with a zwitterionic polysaccharide conjugated with the antigen for a time and under condition to generate an APC presenting the antigen and contacting the APC presenting the antigen with a regulatory T cell for a time and under condition to generate an antigen specific regulatory T cell capable of inhibiting anti inflammatory response against the antigen.

The term "contacting" or "incubating" as used herein indicates actions directed to creation of a spatial relationship between two items provided for a time and under condition such that at least one of the reciprocal or non reciprocal action or influence between the two items can be exerted. In particular, incubation can be performed between a conjugated antigen and a cell and can result in a direct contact and/or interaction between the antigen and the cell or can result in a modification of the cell following an indirect action of the conjugated antigen (e.g. following activation or modification of another compound which directly interacts with the cell).

Incubation can also be performed between a first cell and a second cell following contacting of the first cell with an antigen and can result in a direct contact and/or interaction between the first cell and the second cell or can result in a modification of the second cell following an indirect action of the first cell (e.g. following secretion of cytokines or other molecules which directly interact with the second cell).

The term "antigen presenting cell" or "APC" as used herein indicates a cell that displays an antigen complex with major histocompatibility complex (MHC) on its surface. In particular, antigen presenting cell comprise as dendritic cell, macrophage, B cells, epithelial cells, fibroblasts, glial cells and additional cells identifiable by a skilled person.

The term "zwitterionic polysaccharide" or "ZP" as used herein indicates synthetic or natural polymers comprising one or more monosaccharides joined together by glicosidic bonds, and including at least one positively charged moiety and at least one negatively charged moiety. Zwitterionic polysaccharides include but are not limited to polymers of any length, from a mono- or di-saccharide polymer to polymers including hundreds or thousands of monosaccharides. In some embodiments, a zwitterionic polysaccharide can include repeating units wherein each repeating unit includes from two to ten monosaccharides, a positively charged moiety (e.g. an free positively charged amino moiety) and a negatively charged moiety (such as sulfonate, sulfate, phosphate and phosphonate). In some embodiment ZPs can have a molecular weight comprised between 500 Da and 2,000,000 Da. In some embodiments, the ZPs can have a molecular weight comprised between 200 and 2500. Exemplary ZPs include but are not limited to PSA and PSB from *Bacteroides fragilis*, CP5/CD8 from *Staphylococcus aureus*, and Sp1/CP1 from *Streptococcus pneumonia*. Zwitterionic polysaccharides can be isolated from natural sources, and in particular from bacterial sources, e.g. by purification. Zwitterionic polysaccharides can also be produced by chemical or biochemical methods, as well as by recombinant microorganism technologies all identifiable by a skilled person. Thus, those methods and technologies will not be further described herein in detail.

The wording "polysaccharide A" as used herein indicates a molecule produced by the PSA locus of *Bacteroides fragilis* and derivatives thereof which include but are not limited to polymers of the repeating unit {→3) α-d-AAT Galp(1→4)-[(β-d-Galf(1→3)] α-d-GalpNAc(1→3)-[4,6-pyruvate]-β-d-Galp(1→}, where AATGal is acetamido-amino-2,4,6-trideoxygalactose, and the galactopyranosyl residue is modified by a pyruvate substituent spanning 0-4 and 0-6. The term "derivative" as used herein with reference to a first polysaccharide (e.g., PSA), indicates a second polysaccharide that is structurally related to the first polysaccharide and is derivable from the first polysaccharide by a modification that introduces a feature that is not present in the first polysaccharide while retaining functional properties of the first polysaccharide. Accordingly, a derivative polysaccharide of PSA, usually differs from the original polysaccharide by modification of the repeating units or of the saccharidic component of one or more of the repeating units that might or might not be associated with an additional function not present in the original polysaccharide. A derivative polysaccharide of PSA retains however one or more functional activities that are herein described in connection with PSA in association with the anti-inflammatory activity of PSA.

The terms "conjugated" and "conjugate" as used herein indicates a connection between two or more compounds and/or substances that allow internalization of the compounds and/or substances within a same endosome of an antigen presenting cell, when the conjugated compounds/substances are contacted with the antigen presenting cell. Results illustrated in details in the Examples section support the Applicants' conclusion that the co-inclusion of PSA with *B. fragilis* specific molecules in outer Membrane Vesicles (OMV) and in particular the proximity of said molecules with PSA are determinant for the antigen specific activation of Tregs (see in particular Examples 7-9 and more particularly Example 9 wherein PSA produced by *B. fragilis* fails to suppress antigen specific response to other antigens present in the gut). As a consequence, the Applicants conclude that the co-inclusion in a same closed environment or direct link between the antigen and a ZP (or PSA) can trigger antigen specific activation of Treg in the sense of the present disclosure. Additionally knowledge concerning APCs support the conclusion that the connection and proximity is such that an inclusion within a same endosome is allowed when the conjugated antigen and ZP are contacted with an APC.

Accordingly, conjugation in the sense of the present disclosure comprises physical connection, including direct or indirect linkage and in particular covalent linkage and/or linkage by other chemical bonds between the conjugated compounds/substances. Conjugation in the sense of the present disclosure also comprises a connection established by inclusion of conjugated compounds/substances within a same/common/shared vesicle or other enclosed space, and other interactions or relationship such as a spatial relationship consequent to an elevated concentration of the two or more compounds/substances that allow proximity of the conjugated items in a limited portion of space.

In an embodiment, the zwitterionic polysaccharide can be PSA and/or PSB, as exemplified in the examples section. In an embodiment, PSA or other ZP can be conjugated to the antigen by a physical connection with the antigen such as inclusion of the antigen within a same cellular compartment where PSA is expressed (see e.g. *B. fragilis* expressing PSA in mono-associated animals of Examples 7-9). Additional connections that ensure a similar proximity of the ZP with the antigen are expected to provide similar results are intended to be included within the present disclosure and include direct or indirect covalent linkage to the antigen where, for example, ZP is linked to the antigen through a third compound.

In an embodiment, ZP conjugation with the antigen can be performed by inclusion of ZP and the antigen in vesicles formed by a lipid membrane enclosing an aqueous environment. In particular the vesicle can comprise ZP and the antigen within the aqueous environment or associated to the membrane. In particular, in an embodiment the vesicle can be formed by *B. fragilis* outer membrane vesicle (OMV) described in Example 12.

In an embodiment, PSA or other ZP can be conjugated to non-self antigens, such as those that do not activate a naturally occurring Treg response, and can comprise antigens derived from pathogens (e.g. pathogenic bacteria or viruses) or known antigens involved in autoimmune disease (i.e. MOG peptide). In an embodiment, PSA or other ZP can be conjugated with self antigens that are involved in autoimmune disease. Such autoimmune diseases include, but are not limited to, rheumatoid arthritis; myocarditis; Scleroderma. Type I diabetes, multiple sclerosis. Crohn's disease, ulcerative colitis. Sjorgens syndrome, Hashimoto's thyroiditis, Graves Disease, autoimmune hepatitis, and myasthenia gravis.

In some embodiments, the effective amount of ZP conjugated to the antigen and in particular PSA and/or PSB is from 25 µg to 100 µg for a 25 gram mouse. The results illustrated in the Examples section refer to a dosage of 5 µg/25 gram mouse. Ranges of lower than 10 µg/mouse to above 200 µgs/mouse are also expected to provide a Treg activation in the sense of the present disclosure.

In another embodiment, the effective amount of ZPs, antigens, ZP-antigen complexes, T cells, T regs, antigen presenting cells, and/or vesicles, and any combination thereof, can be determined by those of skill in the art so that a pro-inflammatory immune response is either prevented, inhibited or reduced compared to controls; for instance compared to reactions in the absence of the ZP. Such controls can be designed by those of skill in the art.

In an embodiment, contacting a conjugated PSA-antigen with the APC can be performed in absence of Treg and the resulting APC presenting the antigen is subsequently contacted with the Treg. In an embodiment, contacting conjugated PSA-antigen with the APC can be performed in presence of a Treg and delivered by an antigen presenting cell to the Treg. In those embodiments, conjugation can in particular be performed by inclusion of the antigen and the ZP in vesicles or similarly enclosed space. In an embodiment, an antigen specific antiinflammatory regulatory T cell is generated by contacting a T cell with a zwitterionic polysaccharide conjugated to the antigen for a time and under condition to generate an antigen specific regulatory T cell capable of inhibiting a pro-inflammatory response against the antigen.

In embodiments, the contacting can be performed by directly incubating a ZP conjugated with the antigen with a T cell, and in particular a Treg to activate a tolerogenic immune response. In some of those embodiment, the conjugation can be performed by physical connection and in particular covalent direct or indirect linkage of the ZP with the antigen. Reference is made to the Treg activation performed by direct contacting of PSA illustrated in the Examples section and in particular in Examples 13 to 19.

Exemplary contacting a ZP conjugated antigen with an antigen presenting cell and/or T cell comprise bathing in vitro a whole sample comprising one or more types of cells, in a solution containing the antigen under suitable conditions which depend on the specific cells and the specific antigen and are identifiable by a skilled person upon reading of the present disclosure. Additionally exemplary contacting between a ZP conjugated antigen and an antigen presenting cell and/or T cell can be performed in vitro by introducing the ZP conjugated antigen to a cell culture of purified cells under suitable conditions, and in vivo by treating an individual with the ZP conjugated antigen.

Additional examples of contacting ZP conjugated antigen with an APC in vitro are illustrated in Examples 8 and 9 and FIGS. 17A-D where antigen presenting cells are purified and incubated with the antigen conjugated polysaccharide and subsequently incubated with T lymphocytes to generate a Treg response. In other approaches, an individual can administer the ZP conjugated antigen to generate the Tregs in vivo. In particular, the individual can be treated with a zwitterionic polysaccharide conjugated to an antigen for a time and under conditions to induce an antigen specific anti-inflammatory regulatory T cell in the individual specific for the antigen.

In an embodiment, Treg cells can subsequently be purified out of the individual. An exemplary antigen specific Treg is show in Example 3 and FIG. 5A. An additional example is provided by FIG. 2A that shows the phenotype of Tregs that are induced in response to PSA treatment and include the expression of IL-10, Foxp3, perforin, TGF-β, and granzyme B.

In an embodiment, a T cell with a zwitterionic polysaccharide conjugated to the antigen for a time and under condition to generate an antigen specific regulatory T cell capable of inhibiting a pro-inflammatory response against the antigen Detection of generated Tregs can be performed by using suitable labels and related suitable techniques identifiable by a skilled person upon reading of the present disclosure The terms "label" and "labeled molecule" or as used herein as a component of a complex or molecule referring to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "signal" or "labeling signal" as used herein indicates the signal emitted from the label that allows detection of the label, including but not limited to radioactivity, fluorescence, chemiluminescence, production of a compound in outcome of an enzymatic reaction and the like.

Exemplary methods for detection of a biomarker expression can be performed by methods known to a skilled person including but not limited to ELISA, Q-PCR and intracellular cytokine staining detected by FACs. In some embodiments, expression of a biomarker can be detected via fluorescent based readouts on a cell culture performed using an antibody specific for the biomarker or molecule associated thereto, labeled with fluorophore, which includes, but not exhaustively, small molecular dyes, protein chromophores, quantum dots, and gold nanoparticles. In an embodiment expression of a biomarker can be detected by detecting expression of a label under the transcriptional control of a biomarker promoter in vivo (e.g., in an animal tissue) or in vitro (e.g. in a cell culture). In some of those embodiments the biomarker can be in particular IL-10 or Foxp3. An additional method can comprise the use of a fluorophore called GFP. GFP or green fluorescent protein is able to be detected by a flow cytometer. GFP is placed under the control of the promoter that drives expression of either IL-10 or Foxp3. Induction of either of these genes by GFP can be used to detect generated Tregs (see e.g. Examples 2 and 3).

In an embodiment, the conjugation can be performed engineering *B. fragilis* to express the given antigen. Purified conjugated polysaccharide will then be incubated with and antigen presenting cells (APC) such as a dendritic cell and then incubated with T regulatory cells to elicit an antigen specific tolerant response.

Inflammatory responses to a particular antigen entity including bacteria that can be inhibited with the methods and systems herein described comprise induction of inflammatory TH17 cells or humoral responses such as IgA production as shown in Examples 7 to 9 and FIGS. 4A-F, 9A, and 10A-E.

In particular, an exemplary antigen specific pro-inflammatory response herein described comprises induction of TH17 cells such as those shown in FIGS. 4A-F. Other inflammatory mediators that can be suppressed by PSA or other ZP include TNF-alpha and IL-1. T effector cell proliferation can also be suppressed by antigen specific Tregs.

In an embodiment, the contacting can be performed with an engineered *Bacteroides fragilis* expressing an antigen for a time and under condition to generate an antigen specific regulatory T cell capable of inhibiting a pro-inflammatory response against the antigen.

In particular, in embodiments where an engineered *B. fragilis* is used, the bacteria will be engineered to express an antigen conjugated to PSA. This bacteria can then be orally delivered to the subject. The bacteria will then be able to colonize the intestine and deliver both PSA and the antigen to the intestinal immune system whereby Tregs will be generated to that specific antigen.

In embodiments, wherein an engineered *B. fragilis* is issued conjugation can be achieved by expressing the antigen in the same cell compartment as PSA. Thus, conjugated the antigen to purified PSA ensures that they are delivered together. Also expression of the antigen on the surface of the engineered strain of *B. fragilis* puts the antigen in the same location as PSA (on the surface of the bacteria and in particular on the outer membrane).

In an embodiment, an engineered *Bacteroides fragilis*, is engineered *Bacteroides fragilis* expresses a heterologous antigen. As mentioned above, the antigen will be engineered to be expressed on the surface of the bacteria so that it is being expressed in the same location as PSA. *B. fragilis* can be engineered to express an exogenous antigen by placing the antigenic sequence under the control of a promoter driving expression of *B. fragilis* genes. In particular genes that are known or identified to be expressed on the outer membrane of *B. fragilis* (e.g. protein A or other compound identifiable by a skilled person). For example, a well characterized cloning vector for *B. fragilis*, called pFD340 can be utilized for such heterologous antigen expression.

In an embodiment, a zwitterionic polysaccharide conjugated with an antigen, an engineered *B. fragilis* expressing the antigen and/or an antigen specific Treg herein described can be administered in a method of treating or preventing a condition associated with an inflammation in an individual. The method comprises administering to the individual a therapeutically effective amount of the PSA.

The term "therapeutically effective amount" is an amount that results in a reduction, inhibition or prevention of a pro-inflammatory response in the individual. The amount of ZP or PSA to achieve this can be determined by a person of skill in the art.

The term "individual" as used herein includes a single biological organism wherein inflammation can occur including but not limited to animals and in particular higher animals and in particular vertebrates such as mammals and in particular human beings.

The term "condition" as used herein indicates the physical status of the body of an individual, as a whole or of one or more of its parts. Conditions herein described include but are not limited disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms. Exemplary conditions include but are not limited to injuries, disabilities, disorders (including mental and physical disorders), syndromes, infections, deviant behaviors of the individual and atypical variations of structure and functions of the body of an individual or parts thereof. Conditions can also include situations where individuals have or about to receive transplanted tissues/organs or grafts. Such diseases or disorders can include, but are not limited to, rheumatoid arthritis; myocarditis; Scleroderma; Type I diabetes; multiple sclerosis; Crohn's disease; ulcerative colitis; Sjorgens syndrome; Hashimoto's thyroiditis; Graves Disease; autoimmune hepatitis; and myasthenia gravis.

The wording "associated to" as used herein with reference to two items indicates a relation between the two items such that the occurrence of a first item is accompanied by the occurrence of the second item, which includes but is not limited to a cause-effect relation and sign/symptoms-disease relation.

Conditions associated with an inflammation include but are not limited to inflammatory bowel disease, including but not limited to Crohn's disease and ulcerative colitis, asthma, dermatitis, arthritis, myasthenia gravis, Grave's disease, sclerosis, psoriasis.

The term "treatment" as used herein indicates any activity that is part of a medical care for or deals with a condition medically or surgically.

The term "prevention" as used herein indicates any activity, which reduces the burden of mortality or morbidity from a condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

In particular, in an embodiment PSA or other ZP can be conjugated with a given antigen and then administered (e.g. orally or systemically) to the individual to generate an antigen specific immune response. This approach requires only purified polysaccharide and purified antigen and does not necessarily require the generation of the Tregs in vitro but would instead induce these Tregs in the individual.

In another embodiment, *B. fragilis* can be engineered as described to express the antigen conjugated with PSA and then administered to the subject. *B. fragilis* would then be able to colonize the subject and provide a constant source of PSA and antigen. If *B. fragilis* is unable to colonize the subject *B. fragilis* expressing the given antigen could be orally administered over a period of time that is expected to be comparable to the time of administration of purified PSA or other ZP. In another embodiment, therapeutic effective amounts of ZP-conjugated antigen comprise dosages that enables a concentration of ZP-conjugated antigen in the target tissue comprised within the ranges indicated above.

In an embodiment, the condition can be graft rejection and the method wherein engineering Tregs that specifically suppress cellular responses to donor antigens is expected to increase the success rate of graft acceptance.

In an embodiment, the condition can be rheumatoid arthritis. Depletion of Tregs in mouse models of rheumatoid arthritis increase severity of disease, while transfer of Tregs ameliorates disease, indicating that Tregs can play a therapeutic role in the prevention or treatment of rheumatoid arthritis. Since this disease targets antigens found in the joints, Tregs can be designed toward joint proteins. Such antigens associated with rheumatoid arthritis include, but are not limited to, collagen, human chondrocyte glycoprotein 39, proteoglycans, heat shock proteins, citrullinated filaggrin, glucose-6-phosphate isomerase, p205, and BiP.

In an embodiment, the condition can be myocarditis. This disease is marked by inflammation of the heart muscle. This can result from infection, exposure to toxic substances or immunologic etiologies that can lead to chest pain, heart failure and ultimately death. It has been demonstrated that mice receiving cells depleted of Tregs develop severe myocarditis, which resembles giant cell myocarditis in humans, indicating that Tregs can be an important factor in preventing this type of inflammation. Tregs designed to suppress inflammatory responses toward heart and or heart muscle antigens is expected to be a suitable therapy for treating this disease.

In an embodiment, the condition can be Scleroderma. This autoimmune disease is a chronic inflammatory disease characterized by hardening of the skin or other organs. Current treatment includes the use of general immunosuppressants such as methotrexate. The design of Tregs specific for the skin antigens is expected to be an appropriate treatment. Such antigens associated with Scleroderma include, but are not limited to, centrosome or centromere autoantigens such as CENP-C, Ufd2, SSSCA1, PM-Sc1, and B23.

In an embodiment, the condition can be Type I diabetes. There is a large body of evidence to support a role for Tregs in controlling inflammation within the pancreatic beta cell and thus is expected to be an suitable for Treg therapy. Such antigens associated with Type I diabetes include, but are not limited to, insulin, proinsulin, chromogranin, and GAD65.

In an embodiment, the condition can be multiple sclerosis. The target antigens in this disease are well characterized and antigen specific Tregs according to the present disclosure. Such antigens associated with multiple sclerosis include, but are not limited to, Myelin basic protein, proteosome, B-crystallin, myelin oligodendrocyte glycoprotein, proteolipid protein, Transketolase, enolase, and arrestin.

In an embodiment, the condition can be Crohn's disease or ulcerative colitis. Our previous data has already demonstrated that PSA can suppress inflammation within the colon, or current data suggest that PSA induces Tregs during protection from colitis, thereby making PSA a likely candidate for treatment of intestinal inflammation.

In an embodiment, the condition can be autoimmune diseases such as, Sjorgens syndrome, and the corresponding target antigens can be, but not limited to, Myelin basic protein, proteosome, B-crystallin, myelin oligodendrocyte glycoprotein, proteolipid protein, Transketolase, enolase, and arrestin.

In an embodiment, the condition can be autoimmune diseases such as SLE (lupus), and the corresponding target antigens can be, but not limited to, double-stranded DNA, U-1 small nuclear ribonucleoprotein complex.

In an embodiment, the condition can be autoimmune diseases such as Hashimoto's thyroiditis and the corresponding target antigens can be, but not limited to, hyroperoxidase (TPO), thyroglobulin (Tg), and the thyroid stimulating hormone (TSH) receptor.

In an embodiment, the condition can be autoimmune diseases such as Graves Disease and the corresponding target antigens can be, but not limited to, the thyrotropin receptor.

In an embodiment, the condition can be autoimmune diseases such as autoimmune hepatitis and the corresponding target antigens can be, but not limited to, the 210-kD glycoprotein of the nuclear membrane (GP 210), Nucleoporin p62, cyclin A, lamin B receptor, promyelocytic leukemia-associated protein PML, SP100, and CYP 2D6.

In an embodiment, the condition can be autoimmune diseases such as myasthenia gravis and the corresponding target antigens can be, but not limited to, the nicotinic acetylcholine receptor.

The ZP, *Bacteroides fragilis* and/or antigen specific Tregs can be administered purified conjugated polysaccharide can be delivered either systemically (either intraperitoneally or intravenously) or administered orally. *B. fragilis* can be delivered orally. In particular, administration is performed with methods and formulation that ensure that the ZP and antigen are delivered to the target tissues conjugated one with the other. Accordingly, in some embodiments oral administration requires formulations that allow neutralization of the acid in the stomach (e.g. with suitable capsule formulations).

In an embodiments, the engineered *Bacteroides fragilis* expressing an antigen, the zwitterionic polysaccharide, and the antigen herein described can be provided in a system possibly together with other reagents suitable to be used in the methods herein described The systems can be provided in the form of kits of parts. In a kit of parts, the *Bacteroides fragilis*, zwitterionic polysaccharide, antigen and other the reagents can be included in one or more compositions, and each *Bacteroides fragilis*, zwitterionic polysaccharide, antigen and reagent can be in a composition together with a suitable vehicle.

Additional components can include labels, labeled molecules and in particular, labeled capture agents specific for an anti-inflammatory or an inflammatory biomarker or a molecule associated to the expression thereof, a microfluidic chip, reference standards, and additional components identifiable by a skilled person upon reading of the present disclosure.

The term "capture agent" as used herein indicates a compound that can specifically bind to a target. The wording "specific" "specifically" or "specificity" as used herein with reference to the binding of a first molecule to second molecule refers to the recognition, contact and formation of a stable complex between the first molecule and the second molecule, together with substantially less to no recognition, contact and formation of a stable complex between each of the first molecule and the second molecule with other molecules that may be present. Exemplary specific bindings are antibody-antigen interaction, cellular receptor-ligand interactions, polynucleotide hybridization, enzyme substrate interactions etc. By "stable complex" is meant a complex that is detectable and does not require any arbitrary level of stability, although greater stability is generally preferred. In some embodiments, the kit can comprise labeled polynucleotides or labeled antibodies.

The components of the kit can be provided, with suitable instructions and other necessary reagents, in order to perform the methods here described. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

The term "compound" as used herein indicates any chemical substance comprised of one or more chemical elements and comprises various substances, molecules or component that include but are not limited to biomolecules and in particular drugs. The term "biomolecule" as used herein indicates a substance compound or component associated to a biological activity including but not limited to sugars, aminoacids, peptides proteins, oligonucleotides, polynucleotides, polypeptides, organic molecules, haptens, epitopes, biological cells, parts of biological cells, vitamins, hormones and the like. The term "drug" as used herein indicates substance that, when absorbed into the body of a living organism, alters normal bodily function. In particular, drugs in the sense of the present disclosure include a chemical substance used in the treatment, cure, prevention, or diagnosis of disease or used to otherwise enhance physical or mental well-being.

The term "mucous membrane" in the sense of the present disclosure indicates a lining of mostly endodermal origin, covered in epithelium, which are involved in absorption and secretion. In an individual, mucous membranes line various body cavities that are exposed to the external environment and internal organs. Mucous membranes are at several places continuous with skin: at the nostrils, the mouth, the lips, the eyelids, the ears, the genital area, and the anus.

A "vesicle" in the sense of the present disclosure is a supramolecular complex formed by a membrane forming lipid and additional molecules assembled in an aqueous environment. In particular, in vesicles herein described the membrane forming lipids are arranged in a lipid layer enclosing an internal aqueous environment herein also indicated as cytosol.

The term "membrane forming lipid" or "amphipatic lipid" as used herein indicates a lipid possessing both hydrophilic and hydrophobic properties that in an aqueous environment assemble in a lipid layer structure that consists of either one or two opposing layers of amphipatic molecules known as polar lipid. Each polar lipid has a hydrophilic moiety, i.e., a polar group such as, a derivatized phosphate or a saccharide group, and a hydrophobic moiety, i.e., a long hydrocarbon chain. Exemplary polar lipids include phospholipids, sphingolipids, glycolipids, ether lipids, sterols and alkylphosphocholins. Amphipatic lipids include but are not limited to membrane lipids, i.e. amphipatic lipids that are constituents of a biological membrane, such as phospholipids like dimyrisoylphosphatidylcholine (DMPC) or Dioleoylphosphoethanolamine (DOPE) or dioleoylphosphatidylcholine (DOPC). In an embodiment, the membrane of the vesicle is formed by a lipid bilayer mimicking a plasma membrane (a biological membrane separating the interior of a cell from the outside environment, and enclose an aqueous environment) and in particular the outer membrane of *B. fragilis*.

Vesicles herein described also comprise a lipopolysaccharide (LPS) either associated with the membrane of the vesicle or comprised in the aqueous environment of the vesicle. The term "lipopolysaccharide" as used herein indicates large molecules consisting of a lipid and a polysaccharide joined by a covalent bond; they are found in the outer membrane of Gram-negative bacteria, act as endotoxins and elicit strong immune responses in animals. In particular, vesicles herein described comprise one or more LPS of *B. fragilis* which are identifiable by a skilled person.

Vesicles herein described can also comprise a peptidoglycan either associated with the membrane of the vesicle or comprised in the aqueous environment of the vesicle. The term "peptidoglycan" as used herein indicates a polymer consisting of sugars and amino acids that forms a mesh-like layer outside the plasma membrane of bacteria (Eubacteria, not Archaebacteria), forming the cell wall. In particular, vesicles herein described comprise one or more peptidoglycans of *B. fragilis* which are identifiable by a skilled person.

In one embodiment the vesicle comprising the zwitterionic polysaccharide (i.e. PSA) or PSA itself can be termed a "compound" or part of a "composition" to be administered to an individual or patient in need of treatment. For instance, in patients who have inflammation or inflammatory disorders.

Additional compounds that can be comprised in the vesicles, comprise membrane proteins, membrane lipids carbohydrates and nucleic acids, and in particular, membrane proteins, membrane lipids carbohydrates and nucleic acids of *B. fragilis*.

Exemplary vesicles in the sense of the present disclosure comprise small membrane-enclosed sacs that can store or transport substances. Vesicles can form naturally because of the properties of the membrane forming lipid, or they may be prepared from bacterial membranes. Most vesicles have specialized functions depending on what materials they contain on the membrane and/or the aqueous environment.

In an embodiment, the vesicles herein described are formed by portions of membranes of bacteria. In an embodiment, vesicles are formed by Outer Membrane Vesicles (OMVs) of the bacteria.

In some embodiments, where the composition is to be administered to an individual the composition can be a pharmaceutical composition, and comprise one or more vesicles each comprising PSA. In a more particular embodiment, the pharmaceutical composition can comprise of one or more vesicles each comprising PSA and one or more of another compound, and/or a pharmaceutically acceptable or appropriate carrier/vehicle.

In another embodiment, the above pharmaceutical composition, comprising one or more vesicles each comprising PSA and one or more of another compound, and/or a pharmaceutically acceptable or appropriate carrier/vehicle, wherein an individual/subject with an inflammatory condition or inflammation given this composition shows an improvement.

In some embodiments, the vesicles herein described can be included in pharmaceutical compositions together with an excipient or diluent. In particular, in some embodiments, pharmaceutical compositions contain vesicles herein described, in combination with one or more compatible and pharmaceutically acceptable vehicle, and in particular with pharmaceutically acceptable diluents or excipients.

The term "excipient" as used herein indicates an inactive substance used as a pharmaceutically acceptable or appropriate carrier for the active ingredients of a medication. Suitable excipients for the pharmaceutical compositions herein disclosed include any substance that enhances the ability of the body of an individual to absorb vesicles herein described. Suitable excipients also include any substance that can be used to bulk up formulations with vesicles herein described to allow for convenient and accurate dosage. In addition to their use in the single-dosage quantity, excipients can be used in the manufacturing process to aid in the handling of vesicles herein described. Depending on the route of administration, and form of medication, different excipients may be used. Exemplary excipients include but are not limited to antiadherents, binders, coatings disintegrants, fillers, flavors (such as sweeteners) and colors, glidants, lubricants, preservatives, sorbents.

Pharmaceutically acceptable or appropriate carriers can be, but not limited to, organic or inorganic, solid or liquid excipient which is suitable for the selected mode of application such as oral application or injection, and administered in the form of a conventional pharmaceutical preparation. Such preparation includes solid such as tablets, granules, powders, capsules, and liquid such as solution, emulsion, suspension and the like. Said carrier includes starch, lactose, glucose, sucrose, dextrine, cellulose, paraffin, fatty acid glyceride, water, alcohol, gum arabic and the like. If necessary, auxiliary, stabilizer, emulsifier, lubricant, binder, pH adjustor controller, isotonic agent and other conventional additives may be added.

The pharmaceutically acceptable or appropriate carrier may well include other compounds known to be beneficial to an impaired situation of the gut, (e.g., antioxidants, such as Vitamin C, Vitamin E, Selenium or Zinc); or a food composition. The food composition can be, but is not limited to, milk, yoghurt, curd, cheese, fermented milks, milk based fermented products, ice-creams, fermented cereal based products, milk based powders, infant formulae, tablets, liquid bacterial suspensions, dried oral supplement, or wet oral supplement.

The term "diluent" as used herein indicates a diluting agent which is issued to dilute or carry an active ingredient of a composition. Suitable diluent include any substance that can decrease the viscosity of a medicinal preparation.

In certain embodiments, compositions, compounds, and, in particular, pharmaceutical compositions can be formulated for enteral administration including, but not limited to, i) by mouth (orally) as tablets, capsules, or drops; ii) by gastric feeding tube, duodenal feeding tube, or gastrostomy; and enteral nutrition; and iii) rectally as a suppository.

In some embodiments, vesicles herein described comprising PSA can be used in a method of treating or preventing a condition in an individual.

The method comprises administering to the individual an effective amount of the composition or pharmaceutical composition. The term "Individual" as used herein includes a single biological organism wherein inflammation can occur including but not limited to animals and in particular higher animals and in particular vertebrates such as mammals and in particular human beings.

Further details concerning the identification of the suitable carrier agent or auxiliary agent of the compositions, and generally manufacturing and packaging of the kit, can be identified by the person skilled in the art upon reading of the present disclosure.

EXAMPLES

The methods and systems herein described and the related compositions are further illustrated in the following examples, which are provided by way of illustration and are not intended to be limiting.

In particular the following examples relate to generation of antigen specific T regulatory cells specific for *B. fragilis*. In particular, illustrated herein are Tregs generated by PSA and/or *B. fragilis* that are able to specifically inhibit immune responses elicited by the host to *B. fragilis* itself. A skilled person will appreciate the applicability of the methods and systems herein exemplified for PSA conjugated to *B. fragilis* or to *B. fragilis* expressing PSA to any zwitterionic polysaccharide conjugated to another antigen, including other bacteria or pathogens or molecules associated thereto in view of the teaching of the present disclosure. Additionally, a skilled person will appreciate the applicability of the methods and systems herein exemplified to administration of the antigen for treatment or prevention of immune mediated diseases where a given antigen/s are driving the disease, antigen specific Tregs can be engineered to suppress these immune responses.

The following material and methods were used for all the methods and systems exemplified herein.

Mice and Bacteria.

8-10 week old SPF (Specific Pathogen Free) C57BL/6 mice were purchased from Taconic Farms. 8-10 week old SPF Balb/c mice purchased from Taconic were used for the TNBS model of colitis. Foxp3-GFP on C57Bl/6 background were a kind gift from Talal Chatila (University of California, Los Angeles). Foxp3-GFP mice were devoid of *Helicobacter* species. TLR 2−/− mice were purchased from Jackson. Germ-free C57Bl/6 and Rag−/− mice were bred in plastic Trexler isolators at Caltech, fed autoclaved food and water, and screened weekly by PCR and microbiological plating to ensure sterility. To obtain germ-free C57Bl/6 Foxp3-GFP or Foxp3-DTR bone marrow chimeras, C57BL/6 or Rag−/− germ-free mice were lethally irradiated and reconstituted with bone marrow from Foxp3-GFP donors by retroorbital injection or intraorbital injection. Mice were immediately placed in newly autoclaved cages and water supplemented with antibiotics (100 mg/ml gentamicin and 10 mg/ml erythromycin) throughout the 2 month reconstitution period. Mice were colonized by oral gavage with strains of *B. fragilis* NCTC9343 that are resistant to erythromycin and gentamicin. For transfer experiments, germfree Rag−/− mice were sublethally irradiated 24 hours prior to cell transfer. For diphtheria toxin experiments, mice were given 50 µg/kg of diphtheria toxin intraperitoneally (i.p) for two consecutive days and every third day thereafter. Mice were sacrificed between day 10-14 post treatment. All mice were fed LabDiet 500010 chow, and were cared for under IACUC guidelines from the California Institute of Technology.

In Vitro Suppression Assay.

Either CD4+CD25+ or CD4+Foxp3+ cells were used as a source of Tregs. CD4+CD25− cells were pulsed with 1 ml of a 5 mM CFSE stock for 10 minutes at 37° C. CFSE labeled cells were washed in PBS twice and immediately used. $1 \times 10^5$ mitomycin C (Sigma) treated CD4 depleted splenocytes were mixed with CFSE-pulsed CD4+CD25− (or Foxp3−) responder cells. Indicated dilutions of CD4+CD25+ Treg cells were titrated in and 1 µg/ml of anti-CD3 was added in a round bottom 96 well plate. Cultures were incubated for 3-4 days and then analyzed by flow cytometry.

Quantitative Real-Time Polymerase Chain Reaction.

RNA was collected from indicated cells using Trizol (Invitrogen). cDNA was made using an iSCRIPT cDNA syn in vitro thesis kit per manufacturer's instructions (Bio-Rad). qRT-PCR reactions were performed using IQ SYBR Green Supermix per manufacturer's instructions (Bio-Rad). Reactions were run on the Bio-Rad IQ5 q-PCR machine. Primers are as follows ICOS: F 5'-TAC TTC TGC AGC CTG TCC AT3' (SEQ ID NO:1) & R 5'-CAG CAG AGC TGG GAT TCA TA-3' (SEQ ID NO:2); FOXP3: F 5'-GCA ATA GTT CCT TCC CAG AGT TCT-3' (SEQ ID NO:3) & R 5'-GGA TGG CCC ATC GGA TAA G-3' (SEQ ID NO:4); IL-10: F-5' CTG GAC AAC ATA CTG CTA ACC G-3' (SEQ ID NO:5) & R 5'-GGG CAT CAC TTC TAC CAG GTA A-3' (SEQ ID NO:6); EBI3: F 5'-AGC AGC AGC CTC CTA GCC T-3' (SEQ ID NO:7) & R 5'-ACG CCT TCC GGA GGG TC-3' (SEQ ID NO:8); GITR: F-5' TGC CCA GCT ATA CCC TTG GT-3' (SEQ ID NO:9) & R5' CCG CTC TCA TAC ACC CAC TTC-3' (SEQ ID NO:10); CD25: F 5'-AAC CATAGT ACC CAG TTG TCG G-3' (SEQ ID NO:11) & R 5'-TCC TAA GCA ACG CAT ATA GAC CA3' (SEQ ID NO:12); L32: F 5'-AAG CGA AAC TGG CGG AAA C-3' (SEQ ID NO:13) & R 5'TAA CCG ATG TTG GGC ATC AG-3' (SEQ ID NO:14).

Experimental Colitis.

8 week old Balb/c mice were purchased from Taconic. Animals were pretreated with 50 µg of PSA every other day for 6 days prior to administration of TNBS. 0.75-1.5% TNBS (Sigma) in 50% ethanol was rectally instilled using a 3.5 Fr silicone catheter (Instech solomon). Mice were weighed daily until necropsy 5 days post-TNBS administration.

Lamina Propria Lymphocyte Extraction.

The colon was carefully cleaned of the mesentery and residual fat and cut open longitudinally and then cut into large fragments (1-1.5 cm). Fragments were placed in 50 ml conical and rinsed well with ice cold PBS (Invitrogen). Cleaned intestinal fragments were placed in 15 ml of epithelial cell dissociation solution (Ca+ and Mg+ free HBSS with 5 mM EDTA and 10 mM Hepes) at 37° C. for 15 minutes with gentle agitation (100 rpm). This step was repeated once more. The fragments were then minced with a razor blade and then placed in a digestion solution (HBSS with 5% PBS, 3 units/ml of Dispase, 0.5 mg/ml of Collagenase D and 0.5 mg/ml of DNAase I (all from Worthington Biochemical), digested for 20 minutes with slow rotation at 37° C. and then vortexed well. Supernatants were collected by filtering through a 40 µm cell strainer. Digestions were repeated two more times, LPLs re-suspended in 8 ml 40% Percoll and layered this on top of 5 ml of 80% Percoll (GE Healthcare). LPLs were recovered from the interface of the 40 and 80% gradient after centrifugation, washed and used as described.

Intracellular Cell Staining.

For Foxp3 intracellular staining, $0.5-1 \times 10^6$ cells were first surface stained then permeabilized and fixed in 100 ml of Fixation and Permeabilization buffer (eBiosciences). For IL-10 and IFNγ intracellular cytokine staining, lamina propria lymphocytes were extracted and re-stimulated with 750 ng/ml of ionomycin and 50 ng/ml of PMA (Calbiochem) in the presence of 0.51 µl of GolgiPlug (BD biosciences) for 4-5 hrs at 37° C. Cells were subsequently surface stained and fixed with 2% paraformaldehyde. $1 \times 10^6$ cells were permeabilized overnight with 100 µl of Fixation and Permeabilization buffer (eBiosciences). Cells were stained with 0.3 µg of either anti-IL-17A or IL-10 for 20 minutes at 4° C. All antibodies were purchased from eBiosciences.

Bacterial Antigen Preparation.

Bacterial cultures were harvested and washed extensively with PBS and sonicated. Disrupted cultures were spun at 10,000×g for 20 minutes and the supernatant was collected. Bradford was used to determine protein concentration. Supernatants were stored at −20° C. until use.

Bacterial FACS. The protocol of Slack et al. was used to directly measure IgA binding to bacteria (Slack et al., 2009). Briefly, 1 ml of bacterial culture was washed with buffer (PBS 1% BSA, 0.05% sodium azide). Soluble colonic contents were diluted 1:10 in buffer and further diluted (1:2, 1:4, 1:6). 25 µl of antibody solution and 25 µl of bacterial suspension were mixed and incubated at 4° C. for 1 hour. Bacteria were washed before staining with a monoclonal PE-amouse IgA (1:250; Ebiosciences) for 30 minutes at 4° C. Bacteria were washed, fixed in PFA and analyzed by flow cytometry using FSC and SSC parameters in logarithmic mode.

IgA Immunoblot.

1 ml of bacterial culture was pelleted and washed extensively and resuspended in 1 ml of PBS and sonicated. Bacterial lysates were spun at 10,000×g for 20 minutes and the supernatant subjected to Bradford. Equal amounts of lysates were run on an SDS polyacrylamide gel and transferred to PVDF membrane. Membranes were blocked in 5% milk overnight at room temperature. Equal amounts of soluble colonic contents (as measured by Bradford) were used to probe these membranes at 4° C. overnight. Membranes were washed extensively and subsequently probed with a biotin conjugated anti-mouse IgA and streptavidin-HRP.

Colonic IgA Collection and ELISA.

The small intestine or colon was open longitudinally and the intestinal contents (including feces and mucus) were collected in 500 µL of PBS with proteinase inhibitor cocktail (Roche). Samples were weighed and spun at 8000×g for 10 minutes at 4° C. Supernatants were collected and stored at −20° C. until use. For bacterial specific IgA ELISAs, a 96 well plate was coated with 2 µg/ml of lysates collected from *B. fragilis, B. thetaiotaomicron*, or *B. vulgatus* in PBS (100 µL/well) overnight at 4° C. Plates were blocked with Assay Diluent (eBiosciences) for 1 hour at room temperature. 10 µL of colonic contents were diluted in 100 µL of assay diluent and serially diluted $1/10^4$ additional times. Samples were left on overnight at 4° C. Anti-mouse IgA conjugated to biotin was used at 1/1000 dilution for 1 hour at room temperature and streptavidin-HRP (Southern Biotech) was used at 1/1000 dilution for 1 hour at room temperature.

Statistics.

Differences between data sets were analyzed by Mann-Whitney U-test or student's t test using Microsoft excel or Prism 5.0.

Example 1

PSA induces development and expansion of T regs in presence or absence of inflammation and the induced Tregs are functionally suppressive in vitro and in viva The prominent human symbiont *Bacteroides fragilis* prevents intestinal inflammation and experimental colitis through production of the capsular polysaccharide, PSA (27). To determine the impact of PSA on Foxp3+ Tregs during protection from experimental colitis, immune cells were analyzed from animals that were induced for intestinal inflammation and orally treated with purified PSA. TNBS treatment results in a T cell-mediated colonic immune response, as treated animals lost a significant amount of weight, displayed marked thickening of the colon, lymphocyte infiltration and epithelial hyperplasia (data not shown and Ref (27)). As previously reported, disease was not evident in TNBS-treated animals that were fed PSA.

Vehicle treated (PBS) and PBS treated TNBS animals (TNBS+PBS) had a similar percentage of Treg cells within the mesenteric lymph nodes (MLNs) (FIG. 1A). Consistent with PSA's anti-inflammatory properties, mice fed PSA reproducibly had a 10% increase in the percentage of Foxp3+ cells within the CD4+CD25+ compartment of the MLNs (FIG. 1A).

Additionally, the absolute number of CD4+CD25+ Foxp3+ cells in the MLNs was significantly higher in PSA-treated animals when compared to PBS or vehicle treated animals (FIG. 1B). PSA expansion of the Foxp3+ Treg population is specific, as the percentage of B cells in the MLNs did not differ between PBS and PSA fed mice (FIG. 1G). Consistent with an increase in the percentage of Foxp3+ cells in PSA treated mice, there was an increase in the expression of Foxp3 transcripts in total MLNs (FIG. 1C). It was also found that Foxp3 expression was increased on a per cell basis in CD4+CD25+ cells during PSA mediated protection from colitis (FIG. 2B), demonstrating that PSA up-regulates proportional and cell-intrinsic Foxp3 expression. It was previously reported that PSA treatment of animals expands an unknown CD4+ T cell subset (7); the current results suggest that this population may be a CD4+CD25+Foxp3+ Treg cell.

One of the primary functions of Treg cells is to suppress the activation and proliferation of inflammatory T effector cells. The functional capacity of a Treg cell can be assessed by measuring in vitro suppression of proliferation by naive CD4+CD25− T cells pulsed with the fluorophore, CFSE (dilution of this dye is proportional to rounds of cell division). The suppressive capacity of Tregs during PSA mediated protection from experimental colitis was determined by the addition of varying amounts of CD4+CD25+ Treg cells purified from the MLNs of vehicle (PBS only-no TNBS), and PBS- or PSA-treated colitic mice. As expected over 90% of the effector cells underwent proliferation in the absence of Tregs (data not shown), that was partially suppressed when Tregs from vehicle or PBS treated colitic mice were added to the culture (FIG. 1D). Notably however, Tregs isolated from the MLNs of PSA fed mice (TNBS+PSA) suppressed T cell proliferation to a significantly higher degree than cells from untreated animals (43.5% proliferating cells vs. 63.5% at a 1:2 Teff:Treg ratio), demonstrating Tregs from animals protected from colitis by PSA have increased functional suppressive activity.

Dramatic changes occur during an intestinal inflammatory response; including the expansion of antigen specific T and B lymphocytes, activation of innate immune cells, and secretion of copious amounts of inflammatory cytokines. These events result in a complex cytokine milieu with the capacity to influence a countless array of immune pathways. During the steady state however, many of these cytokines are not expressed and the cellular and molecular intestinal environment is very different than that seen during immunity.

To determine whether PSA expands Tregs during homeostasis (such as during commensal colonization), mice were fed PSA and the CD4+CD25+Foxp3+ population of Tregs within the MLNs during the steady state monitored. Mice treated with PSA consistently had an increased percentage of Foxp3+ cells within the CD4+CD25+ T cell subset in the MLN (FIG. 1E). And further during homeostasis, Tregs isolated from PSA-treated animals displayed a greater ability to suppress effector T cell responses compared to control animals (28.5% proliferating cells vs. 43.0% at a 1:2 Teff:Treg ratio) (FIG. 1F).

The findings illustrated in the present example demonstrate that PSA induces functional Tregs in presence or absence of intestinal inflammation.

Example 2. PSA can Induce Development of Functionally Suppressive Tregs Through MHCTCR Recognition The microbiota has profound influences on the development and function of the immune system (Macpherson and Harris, 2004). Colonization of germ-free animals with *Bacteroides fragilis* represents a model system for the study of immune-bacterial symbiosis (Mazmanian et al., 2005). Since recent studies have shown a critical role for Treg-produced IL10 during maintenance of intestinal homeostasis (Rubtsov et al., 2008), it was necessary to understand how *B. fragilis* colonization affects Foxp3+ Treg development and cytokine production.

Germ-free C57Bl/6 mice were mono-associated with wild-type *B. fragilis* or a strain deleted of PSA (*B. fragilis*ΔPSA) (FIGS. 4A-F, 6A-C). Consistent with recent studies (Atarashi et al., 2008; Ivanov et al., 2008), the percentage of CD4+Foxp3+ Tregs within the colon did not differ significantly between groups (FIG. 6), suggesting that the microbiota does not affect naturally occurring Tregs cells within the intestine.

Figure 2A:
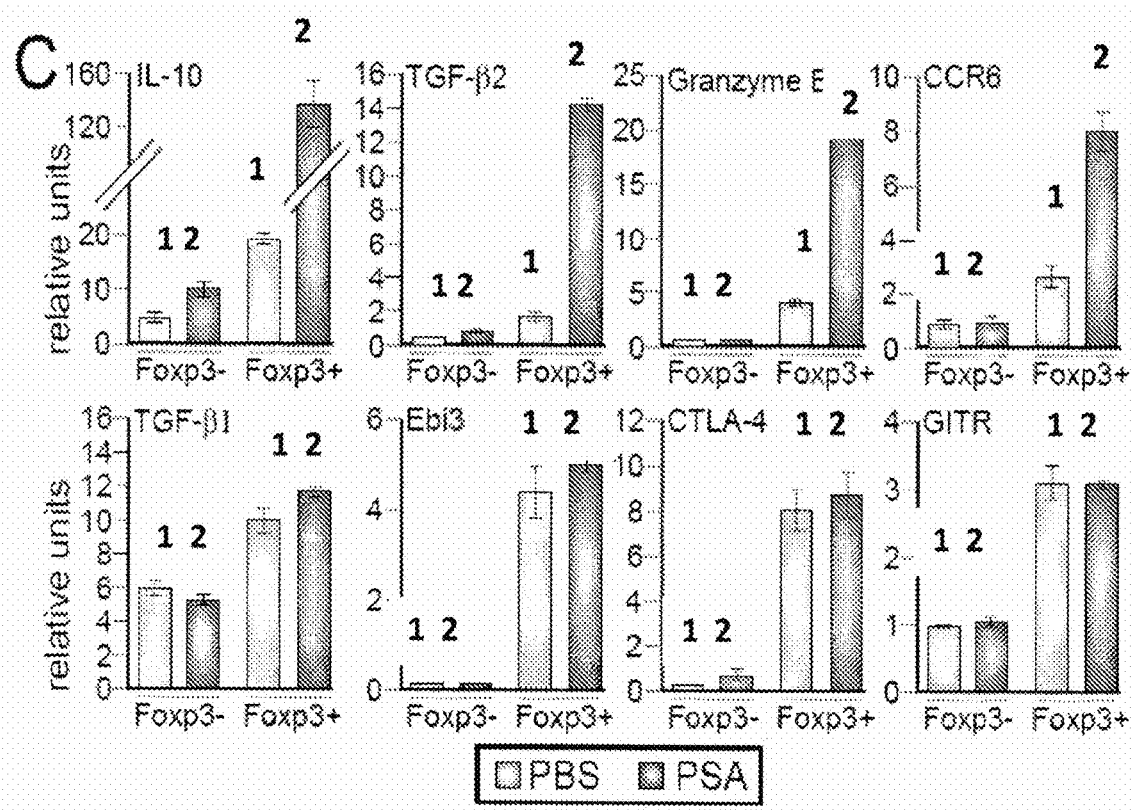
FIGS. 2A-B show that purified PSA activates 'inducible' Foxp3+ Tregs.
Figure 2B:
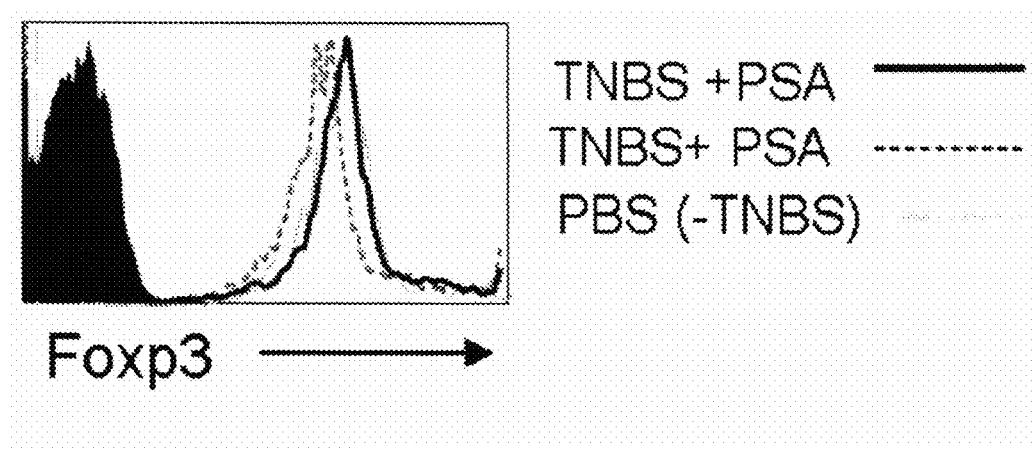
Figure 3A:
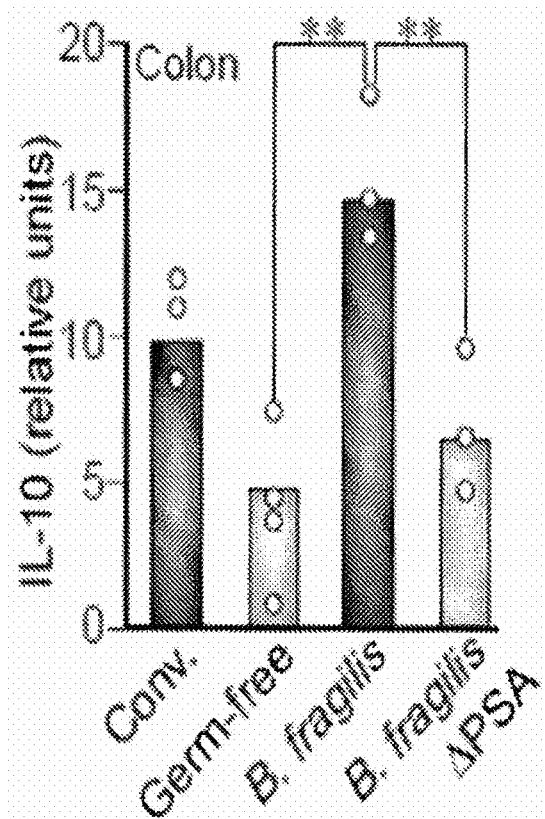
FIGS. 3A-E show that B. fragilis mono-colonization elicits tolerant T cell responses in the intestinal environment.
Figure 3B:
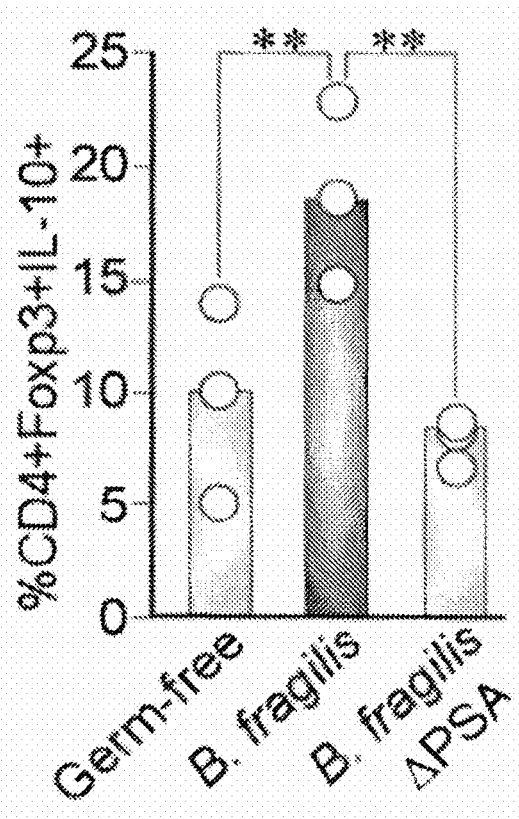
Figure 3C:
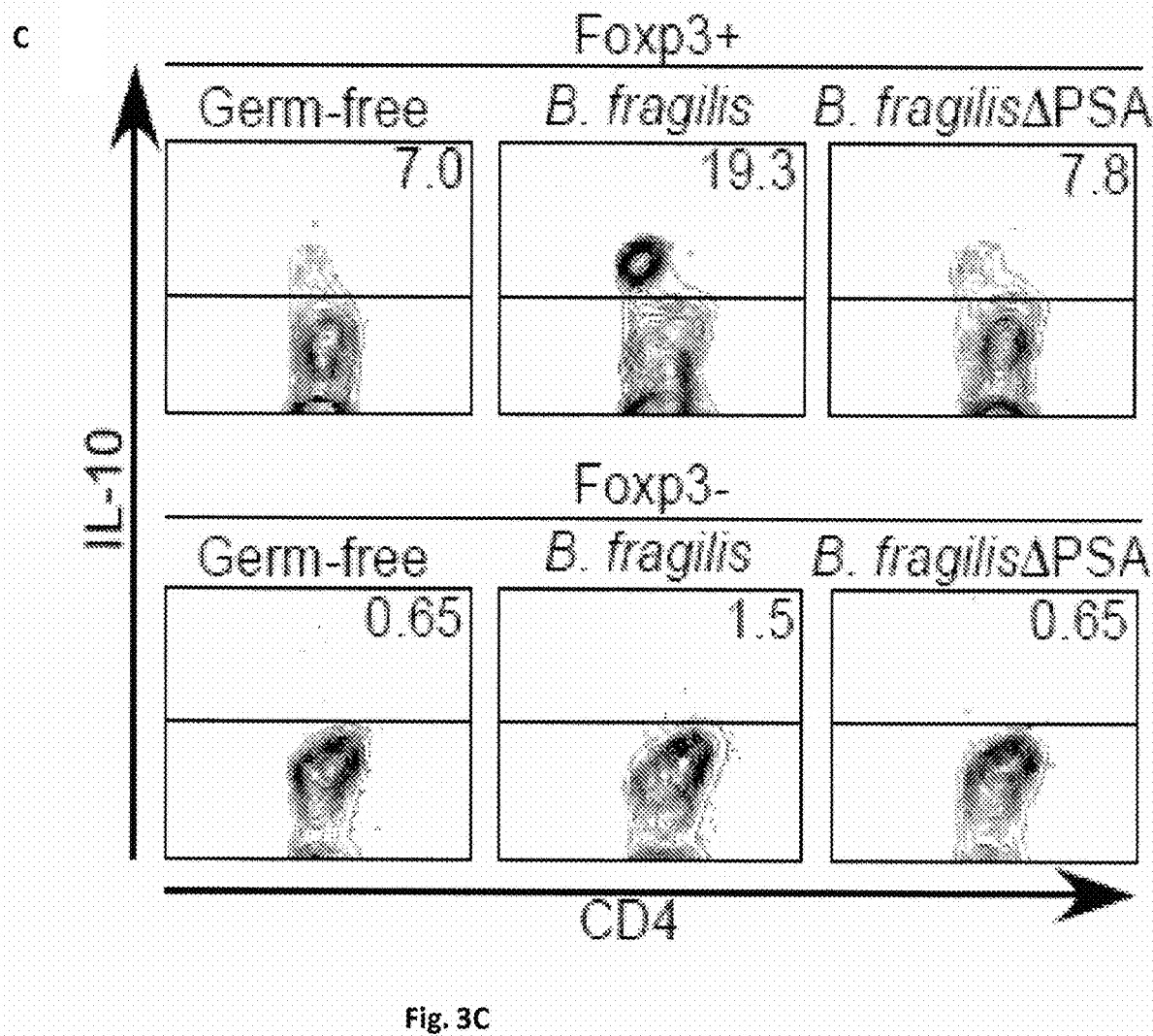
Figure 3D:
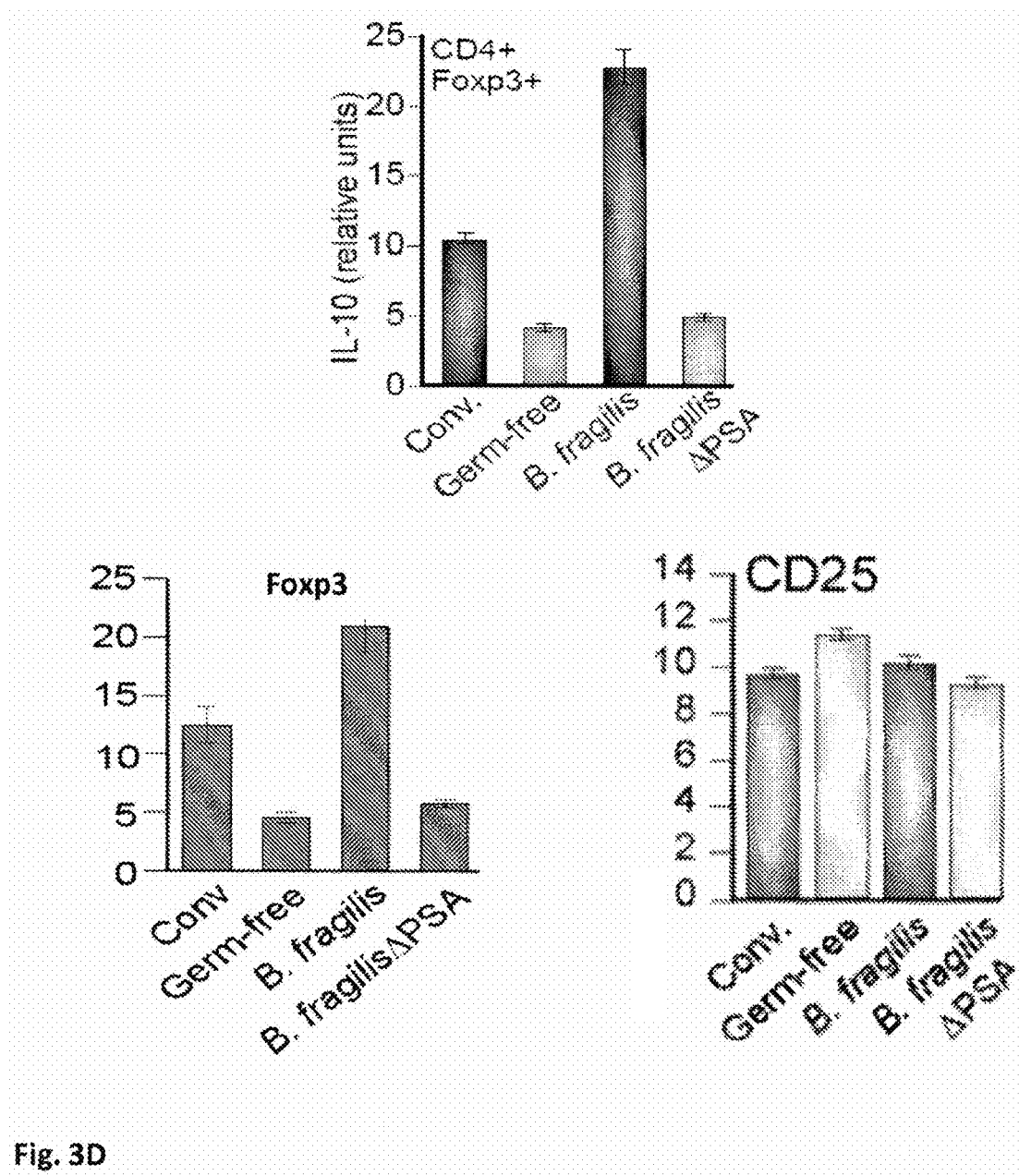
Figure 5A:
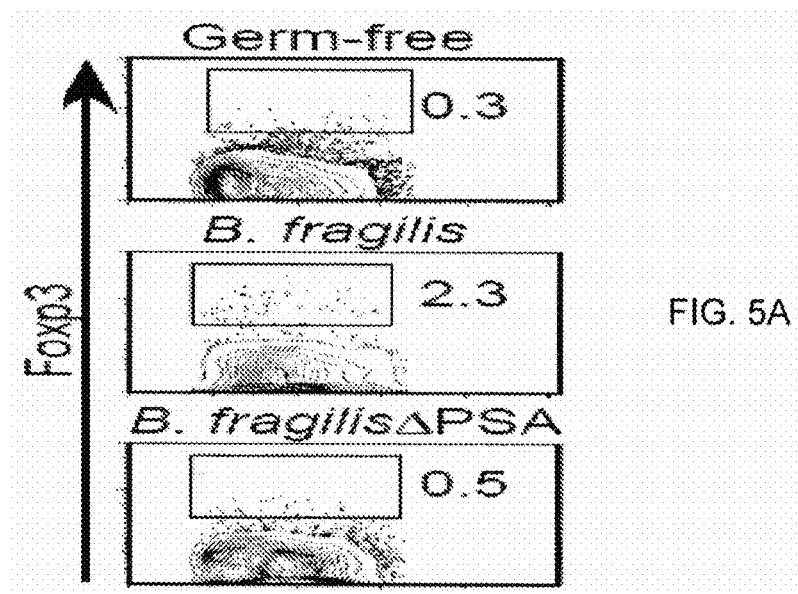
FIGS. 5A-C show that *Bacteroides fragilis* induces regulatory T cell development.
Figure 5B:
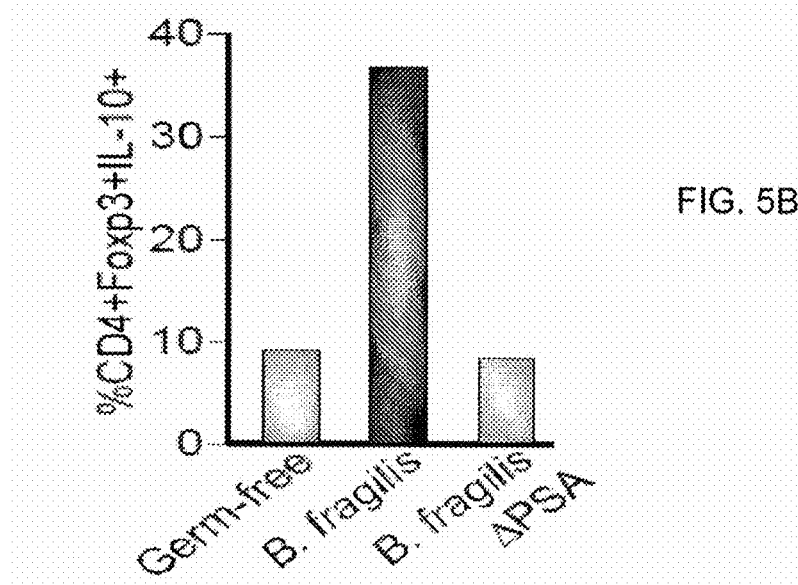
Figure 5C:
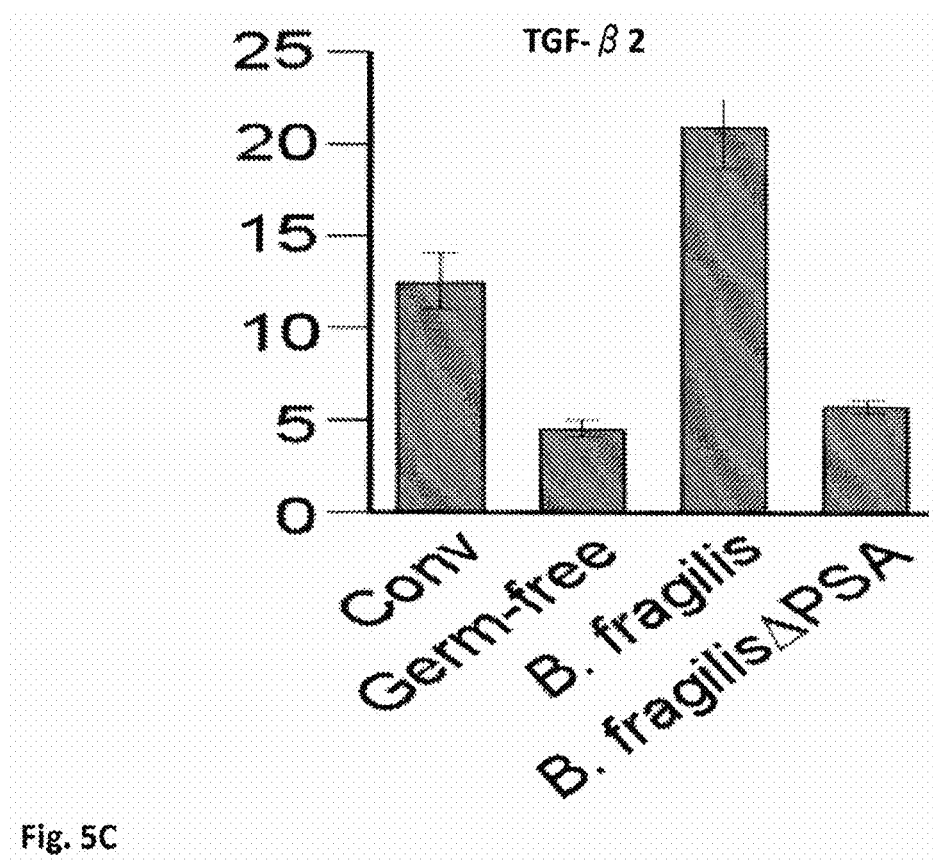
Figure 6A:
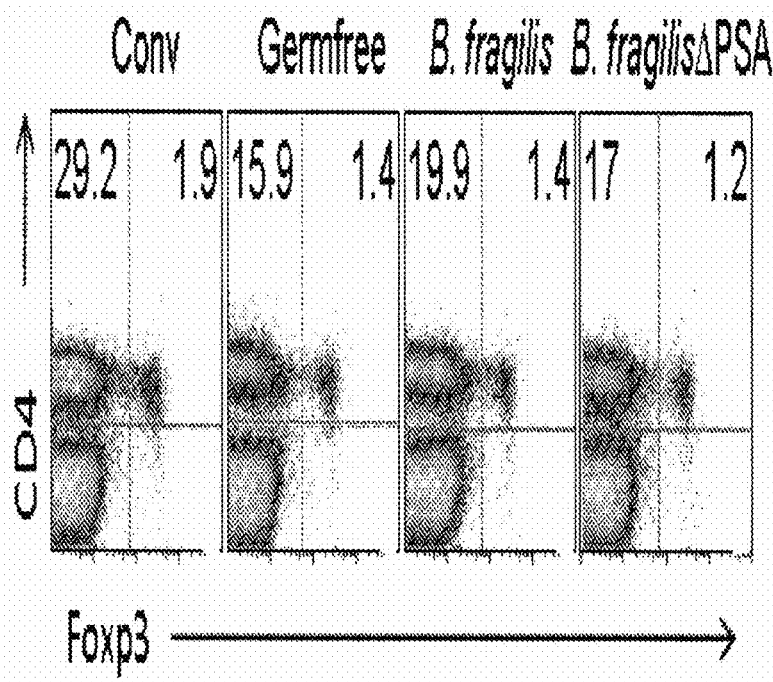
FIGS. 6A-C show that *Bacteroides fragilis* colonization does not affect the presence of naturally occurring Tregs but in the absence of PSA inflammatory responses are induced.
Figure 6B:
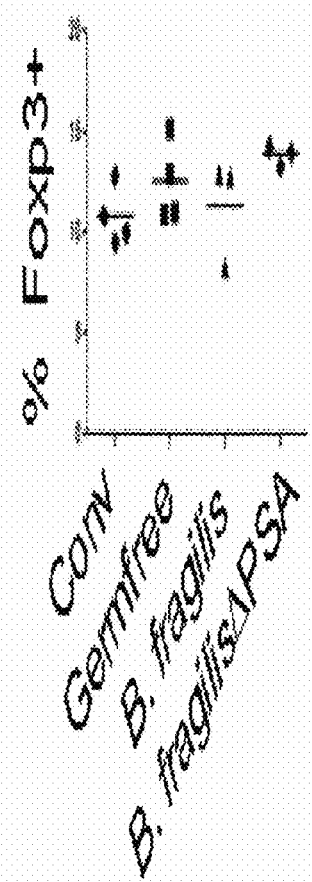
Figure 6C:
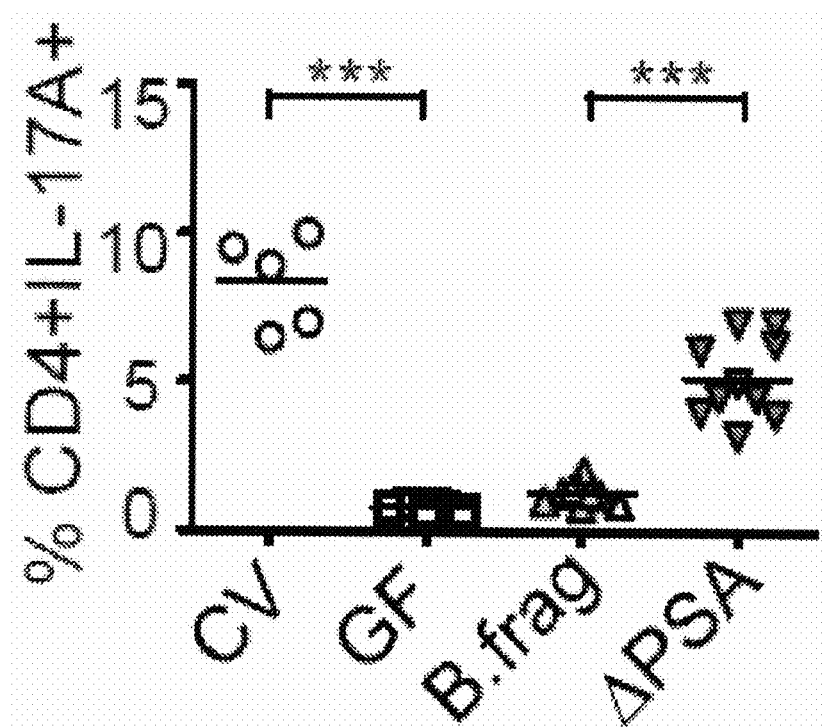

Intriguingly, production of the IL-10 transcript is deficient in the absence of the microbiota; moreover *B. fragilis* colonization restores production of IL-10 in the colon in a PSA-dependent manner (FIG. 3A). Mono-association of germ-free animals with *B. fragilis* results in a significant increase in the proportion of IL-10-producing CD4+Foxp3+ Tregs (FIGS. 3A-E). The induction of IL-10 from Foxp3+ T cells by *B. fragilis* is dependent on PSA, as Tregs from *B. fragilis*ΔPSA colonized animals have similar IL-10 levels as germ-free mice. Colonization with *B. fragilis* directs IL-10 production almost exclusively from Foxp3+(and not Foxp3−) T cells (FIG. 2A, 3D). Compared to conventionally-colonized animals, germ-free mice display lower expression levels of IL-10, Foxp3 and TGF-β2 produced by CD4+Foxp3+ Tregs (FIG. 2A and FIG. 5C). Remarkably, *B. fragilis* mono-association restores expression of these anti-inflammatory genes, a phenotype that is completely PSA dependent. Natural Treg markers such as CD25 are not altered. Thus, PSA induces the development of Foxp3+IL-10+ Tregs in the gut during normal colonization of animals.

To examine whether PSA is able to direct de novo Treg conversion, CD4+Foxp3-T cells were purified from Foxp3-GFP animals (Lin et al., 2007) and adoptively transferred into germ-free Rag−/− lymphopenic mice. Groups of animals were either left germ-free or colonized with wild-type or B. fragilisΔPSA. FIG. 5A shows that while Treg conversion does not occur in germ-free mice, colonization with wild-type B. fragilis induced significant levels of Foxp3+ Tregs. PSA is required for Treg conversion, as B. fragilisΔPSA colonized animals contained Treg cell numbers comparable to germ-free animals (FIG. 5A). Furthermore, Foxp3+ T cells in B. fragilis-colonized animals acquired IL-10 expression (FIG. 5B).

Collectively, CD4+Foxp3+IL-10+ Treg lineage differentiation in the colon requires gut bacteria, revealing PSA as the first bacterial molecule of the intestinal microbiota that regulates Foxp3+ Treg development.

Example 3. Tregs Induced by PSA Exhibit a Characteristic and PSA-Specific Antiinflammatory Gene Expression Profile Tregs potently restrain inflammatory responses through the secretion of IL-10, TGF-β and IL-35 (Collison et al., 2007; Maynard et al., 2007). Additionally, contact-dependent mechanisms include effector T cell cytolysis through the secretion of perforin and granzymes (Gondek et al., 2005), as well as expression of anti-inflammatory surface receptors such as GITR and CTLA-4 (Vignali et al., 2008).

Many subsets of Tregs exist within the Foxp3+ population; therefore to understand how PSA affects the functional capacity of Foxp3+ Tregs, the expression of Treg-associated genes in response to PSA treatment was analyzed. Foxp3-GFP mice (where green fluorescent protein marks Foxp3+ cells) were orally treated with PSA (or PBS control), and gene expression analysis was performed on both CD4+Foxp3+ or CD4+Foxp3-T cells from the MLNs. As expected, Treg-associated genes including IL-10, TGF-β2, were dramatically increased in Foxp3+ compared to Foxp3− T cells (PBS samples; FIG. 2A). Remarkably, PSA induces over 8-fold increased levels of IL-10 from CD4+Foxp3+ Tregs, but had virtually no impact on CD4+Foxp3− T cells.

Accordingly, PSA elicited significant induction of TGF-β2 in Foxp3+ Treg cells. PSA treatment also significantly increases the transcription of granzyme B, perforin and CCR6, a chemokine receptor shown to be associated with the migration of Treg cells (FIG. 2A) (Yamazaki et al., 2008). It is important to note that PSA does not globally impact all Treg derived cytokines as expression of TGF-β1 and Ebi3 is not altered, demonstrating specificity for a distinct Treg profile. Furthermore, production of the 'natural' Treg-associated surface molecules CTLA-4, GITR, CD25 and ICOS are not changed among Foxp3+ cells in response to PSA treatment (FIG. 2A). Taken together, these data suggest that PSA activates 'inducible' Foxp3+iTregs and reveals a PSA-specific gene expression program within Foxp3+ Treg cells.

In a separate experiment, Foxp3-GFP mice were gavaged with purified PSA (or PBS control), and RNA was extracted from either CD4+Foxp3-non-Treg or CD4+Foxp3+ Treg cells of the MLNs following FACS purification. As expected, gene expression in Foxp3- and Foxp3+ T cell subsets differed dramatically and included higher basal levels of IL-10, TGF-β1 CD25, GITR, ICOS, and CTLA-4 in Foxp3+ T cells (FIG. 2A). It was previously reported that IL-10 production by an unknown CD4+ T cell population is required for PSA-mediated protection from intestinal inflammation (27). Very intriguingly, PSA induces over 8-fold increased levels of IL-10 from CD4+Foxp3+ Tregs than that expressed in PBS-treated cells (FIG. 2A). While PSA marginally up-regulated TGF-β2 expression in non-Treg cells, it elicited over 7-fold induction of TGF-β2 in Treg cells. PSA treatment also significantly increases the transcription of granzyme B and perforin from Foxp3+ Tregs. It is important to note that PSA does not globally impact all Treg-derived cytokines as expression of Ebi3 and TGF-β1 is not altered, demonstrating specificity for a PSA-induced Treg profile. Furthermore, production of the 'natural' Treg-associated surface receptors CD25, GITR, ICOS, and CTLA-4 are not changed among Foxp3+ cells in response to PSA treatment (FIG. 2A).

Taken together, these data suggest that PSA activates 'inducible' Foxp3+ Tregs that suppress inflammation through cytokine and cytolytic mechanisms, revealing a PSA-specific gene expression program within Treg cells.

Example 4. T Regs Induced by PSA Actively Engender T Cell Tolerance Through IL10 Production and/or Activation of a Th1 Profile To determine whether PSA alone is sufficient to expand Tregs, conventionally-colonized mice were fed PSA and proportions of CD4+Foxp3+ Tregs within the MLNs were monitored. Mice orally treated with PSA display increased percentages of CD4+Foxp3+ T cells in the MLNs (FIG. 1A). One of the primary functions of Treg cells is to suppress the activation and proliferation of inflammatory T effector cells. Treg function was determined by the addition of various ratios of CD4+CD25+ Treg cells purified from MLNs to naive CD4+CD25− T cells. It was found that Tregs isolated from PSA-treated animals display considerably greater ability to suppress in vitro T cell responses compared to PBS-treated control animals (e.g., 28.5% proliferating cells vs. 43.0% at a 1:2 Treg:Teff ratio) (FIG. 1F,). These findings demonstrate that PSA induces functional Foxp3+ Tregs with enhanced suppressive capacity in conventionally-colonized animals.

Applicants previously reported that colonization of germ-free animals with PSA-producing bacteria increases the Th1 cytokine interferon-g (IFNγ) among splenic CD4+ T cells (Mazmanian et al., 2005). In particular, Applicants previously showed that Tregs induced by PSA have the ability to direct Th1/Th2 response (see Mazmanian, et al 2005). Th1 responses are generally believed to be controlled by the transcription factor T-bet; however, a recent report has revealed that a subset of Foxp3+ Tregs express T-bet, but lack IFNγ expression (Koch et al., 2009).

Figure 8A:
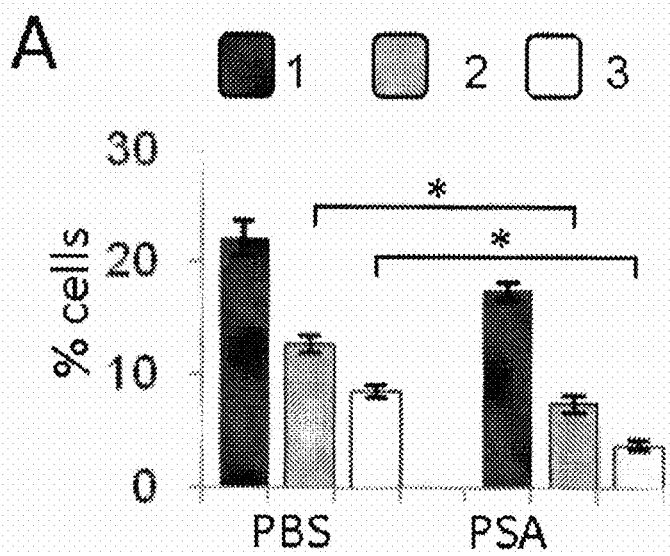
FIGS. 8A-F show purified PSA is sufficient to induce functional Foxp3+ Tregs with an inducible phenotype.
Figure 8:
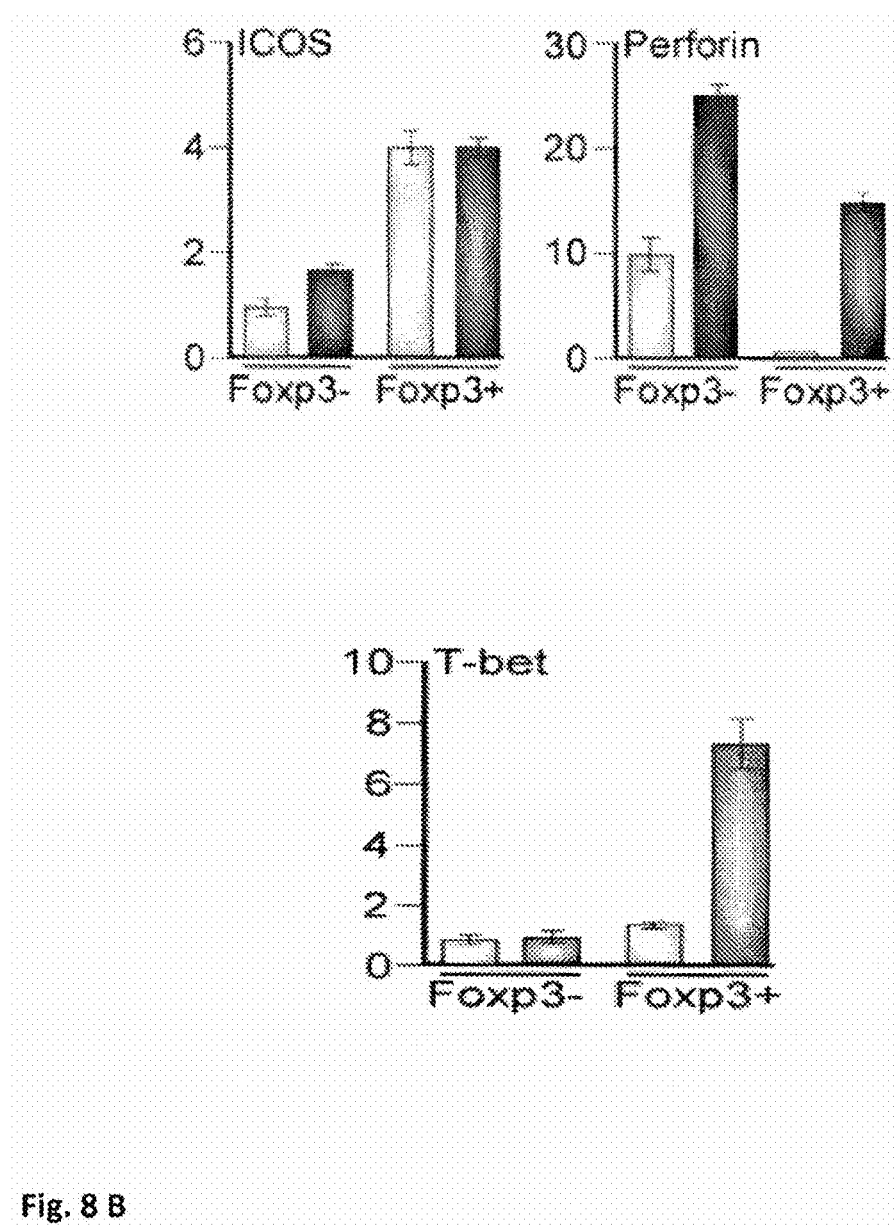

It was now found that CD4+Foxp3+ T cells within the MLNs of wild-type B. fragilis colonized animals express T-bet in a PSA-dependent manner (FIG. 8B). Intriguingly, these cells do not produce IFNγ (FIG. 8D). However, splenic CD4+ T cells from the same animals express IFNγ from non-Tregs in a PSA-dependent manner (FIGS. 8A-F). Remarkably, splenic T cells do not produce IL-10, unlike those of the MLNs.

These results reveal a compartmental difference in the ability of PSA induced Treg to elicit a protective response. In particular, while PSA induced Tregs are capable to induce a Th1 profile in the spleen, corresponding Tregs in the gut promote tolerance through production of IL-10. Additionally, the ability of PSA promoting development of Foxp3+

IL10+ Treg cells in the gut, further supports the notion that PSA actively engenders mucosal tolerance.

Example 5. B. Fragilis Mono-Association of Mice Elicits Tolerant a PSA Dependent Treg Response Specific to B. Fragilis Germ-free mice have numerous developmental and functional defects suggesting that the microbiota has profound influences on the intestinal immune response (4). Monoassociation of germ-free mice provides an ideal model system to analyze the physiological contributions of individual bacterial species, and assign molecular functions through comparative colonization with bacterial mutants. To further understand how B. fragilis colonization affects Treg cell development, germ-free C57Bl/6 mice were lethally irradiated (to deplete all hematopoietic cells) and they were reconstituted with bone marrow from Foxp3-GFP animals. Mice were subsequently left germ-free or mono-associated with wild-type B. fragilis or a strain deleted of PSA (B. fragilisΔPSA).

Figure 3E:
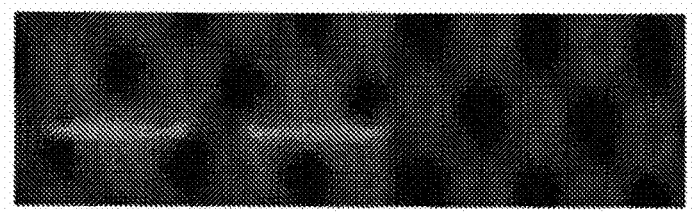

Mice were monitored weekly by PCR to ensure their microbiological status (FIG. 3E). Consistent with recent reports (21,23), the percentage of Tregs (CD4+Foxp3+) cells residing within either the MLN or colon did not differ significantly between groups (data not shown), suggesting that the microbiota is not a requirement for the presence of naturally occurring Tregs cells within the intestine. However, IL-10 production among Foxp3+ Tregs within the intestine is deficient in the absence of the microbiota; moreover B. fragilis colonization restores the production of IL-10 within the colon in a PSA dependent manner (FIG. 3A). Mono-association of germ-free animals with B. fragilis results in an over 2.5-fold increase in the percentage of IL-10-producing Tregs within the colon (FIGS. 3B and 3C). The induction of IL-10 from Foxp3+ cells by B. fragilis is almost completely reliant on PSA, as Tregs analyzed in B. fragilisΔPSA colonized animals have similar IL-10 levels as germ-free mice. Recent studies have shown that IL-10 production from Foxp3+ Tregs is critical for maintaining homeostasis at mucosal surfaces (31). Thus, commensal colonization by B. fragilis directs the development of functional IL-10-producing Tregs within the intestinal compartment To investigate the impact of microbial colonization on the gene expression profile of Tregs, CD4+Foxp3+ T cells were purified from the MLN of conventionally colonized, germfree, B. fragilis or B. fragilisΔPSA mono-associated mice. Germ-free mice display a deficiency in IL-10, Foxp3, and TGF-β2 expression within the CD4+Foxp3+ Treg population when compared to conventionally colonized mice (FIG. 3D). B. fragilis monoassociation completely restores expression of all three of these genes. Induction of IL-10, Foxp3, and TGF-β2 is completely dependent on PSA production by B. fragilis, as monoassociation of animals with B. fragilisΔPSA does not elevate the expression of these suppressive genes. The changes in gene expression are specific to inducible Treg markers as CD25 is not impacted by homeostatic microbial colonization. Thus, colonization by symbiotic bacteria has a dramatic impact on the programming of Treg-associated genes, demonstrating that B. fragilis induces a tolerogenic intestinal immune environment during host mutualism.

Example 6. PSA Activity on Treg Requires Toll-Like Receptor 2 Signaling

Figures 7A, 7B:
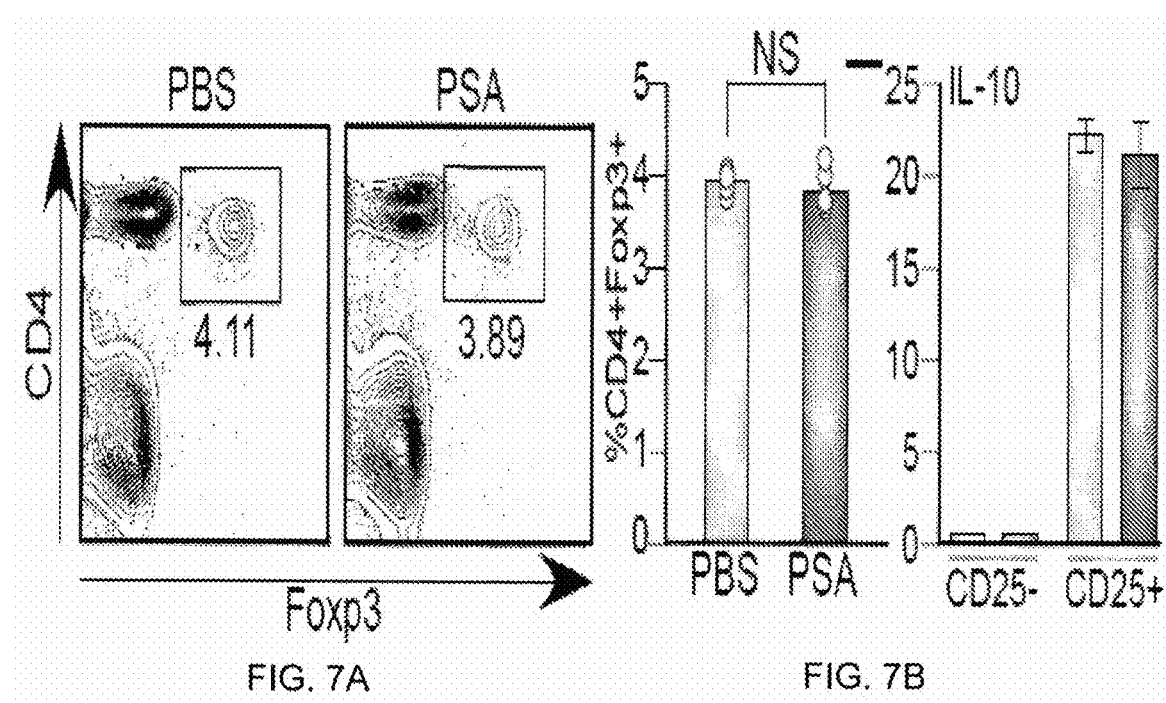
FIGS. 7A-C show that PSA promotes Tregs with suppressive activity in a TLR2 dependent manner.
Figure 7C:
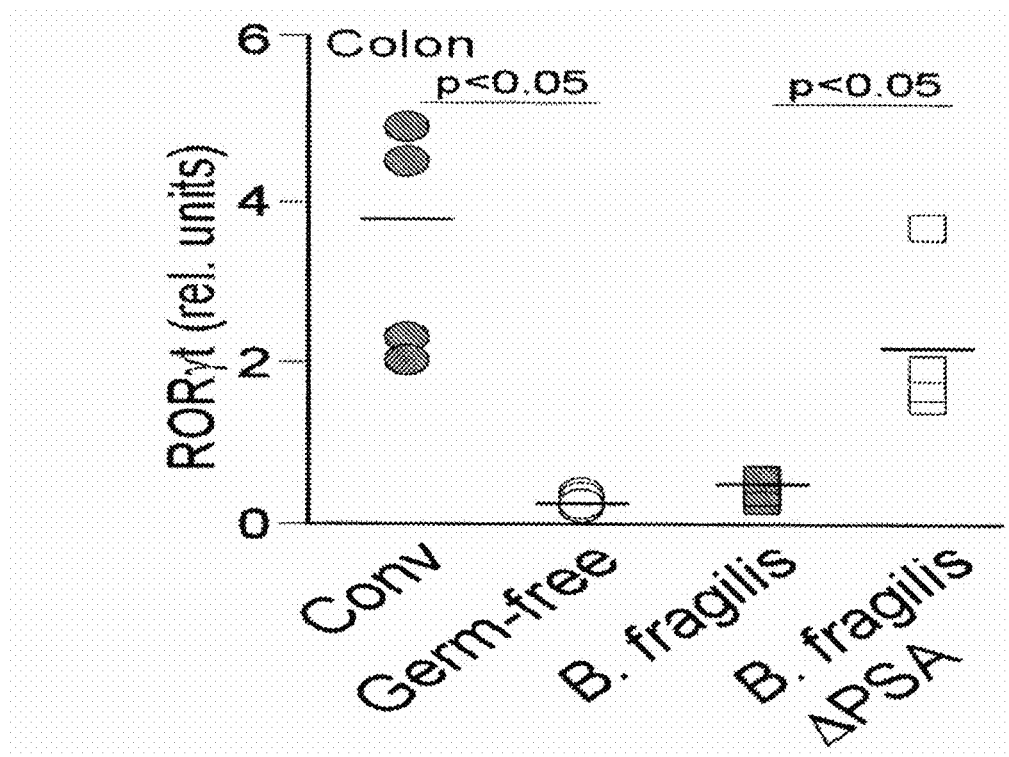

Many microbial products are sensed by pattern recognition receptors such as toll-like receptors (TLRs). Though historically believed to induce inflammation, a series of studies now show that TLR signaling can also promote anti-inflammatory responses (reviewed in (van Maren et al., 2008)). PSA has recently been shown to coordinate cytokine production from innate immune cells through TLR2 signaling (Wang et al., 2006); however a role for TLR2 in Treg development remains unknown. To understand the mechanism by which PSA coordinates Treg biology, TLR2-deficient animals were treated orally with PSA and analyzed for CD4+Foxp3+ T cell development. In contrast to the Treg expansion seen in wild-type animals (FIG. 7A), no difference in the percentage of CD4+Foxp3+1' cells in TLR2−/− mice treated with PSA was observed (FIGS. 7A-C). Additionally, induction of IL-10 by Tregs in response to PSA is lost in the absence of TLR2 expression (FIG. 7B). The findings are entirely consistent with reports that TLR2 knockout mice have defects in Foxp3+ Treg cells (Liu et al., 2006; Sutmuller et al., 2006). Though further work is needed to fully understand how innate immune signaling contributes to Treg lineage differentiation, PSA-mediated Treg development is a TLR2 dependent mechanism.

Example 7. In Absence of PSA B. Fragilis Induces an Inflammatory Immune Responses Specific for B. fragilis Almost all bacteria share microbial ligands for pattern recognition receptors (e.g., LPS (endotoxin), peptidoglycan, unmethylated CpG, etc), suggesting that molecular mechanisms must allow the mucosal immune system to distinguish between symbiotic and pathogenic bacteria. Current theories for this discrimination include spatial separation between the immune system and the microbiota (immunologic ignorance), as well as innate immune suppression (Hooper, 2009). To control microbial infections, the immune system elicits the function of pro-inflammatory Th 17 cells. Tregs control Th 17 immunity in order to prevent collateral damage to host tissues, and Treg function is required for suppression of immune reactions to both innocuous non-self and self antigens. Furthermore, symbiotic and pathogenic bacteria share many microbial ligands for pattern recognition receptors, suggesting that molecular mechanisms must allow the immune system to discriminate between beneficial and harmful bacteria.

Figures 4A, 4B, 4C, 4D, 4E:
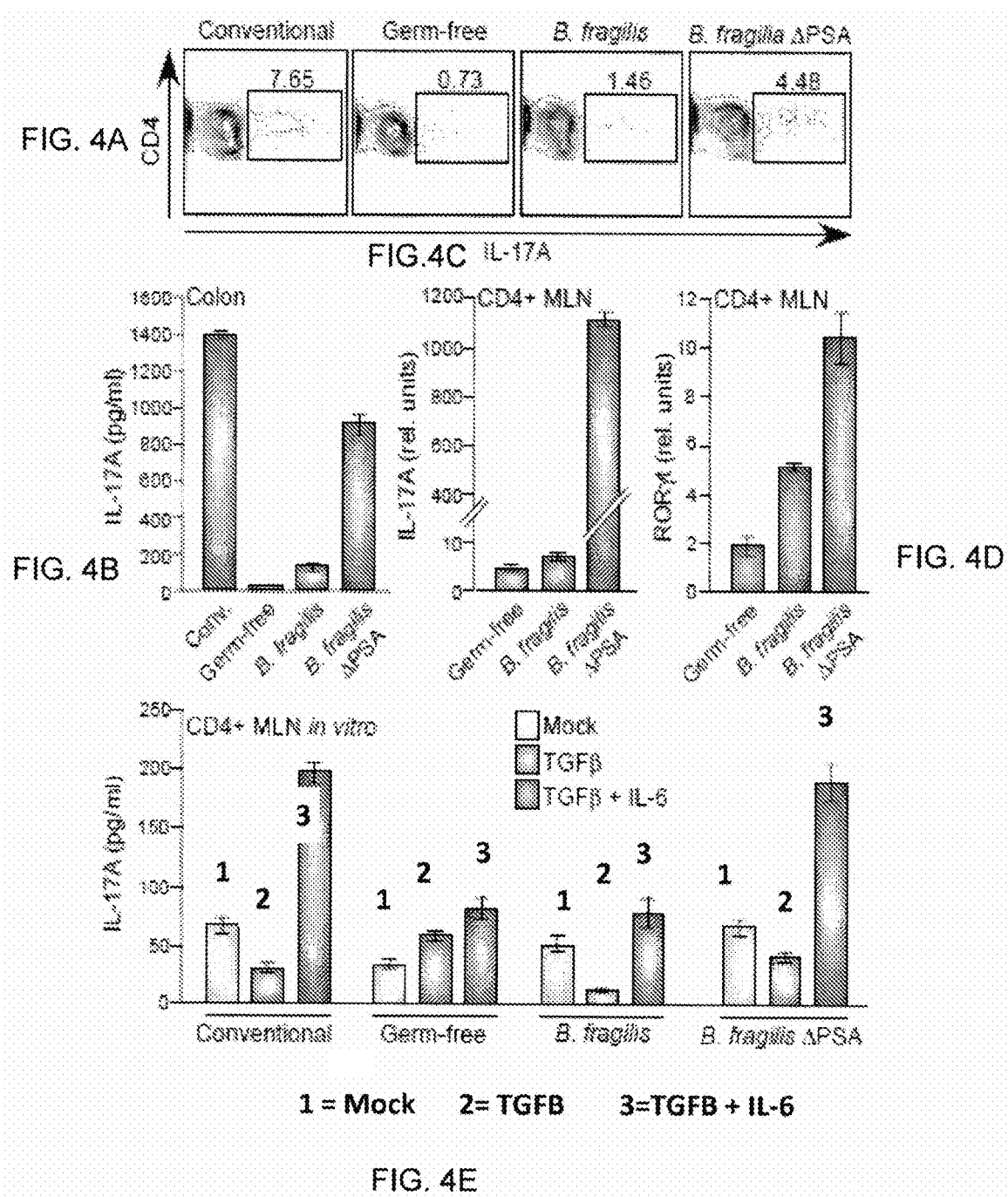
FIGS. 4A-F show that intestinal tolerance toward B. fragilis colonization is lost in the absence of PSA.
Figure 9A:
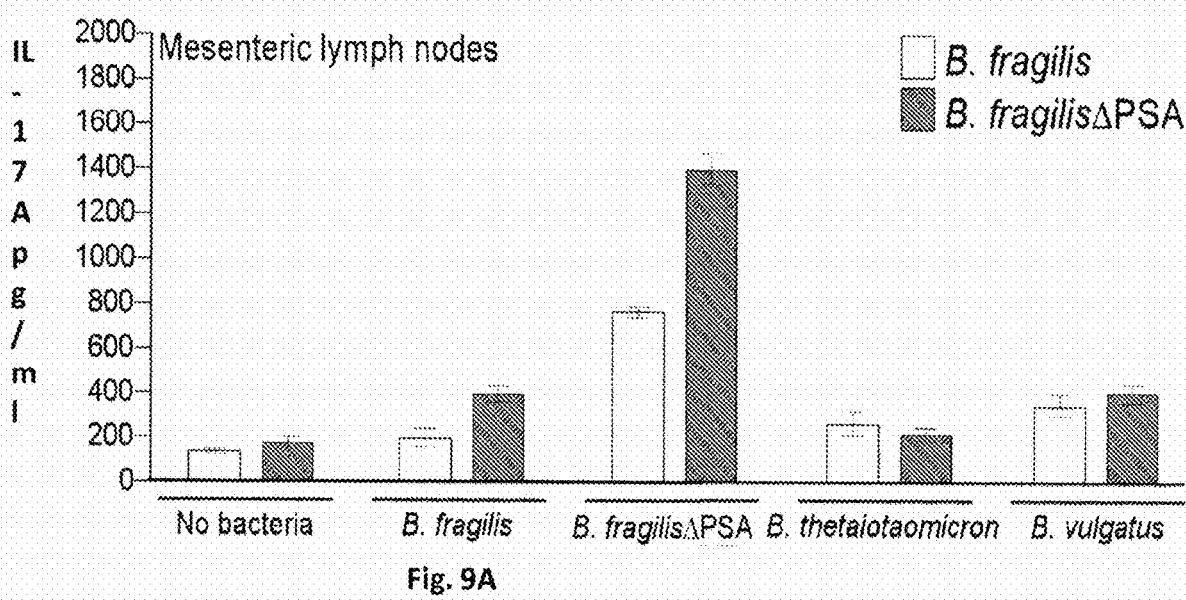
FIG. 9A shows that Th 17 cell responses are induced in the absence of PSA.
Figure 10A:
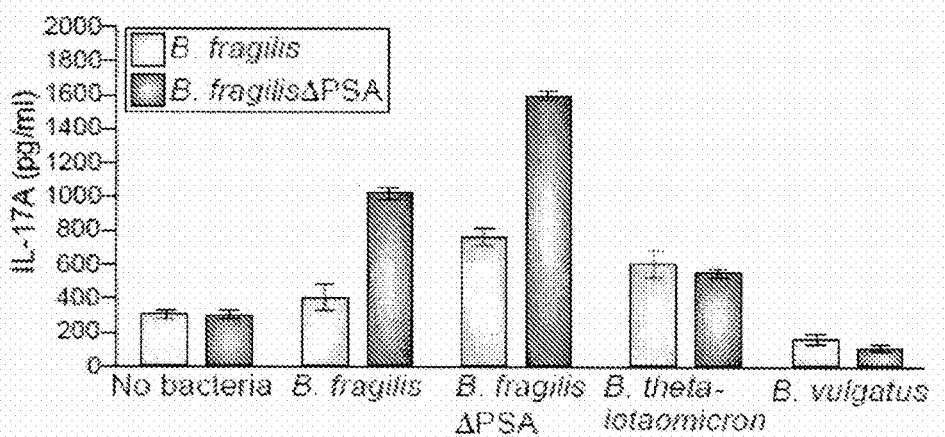
Figure 10B:
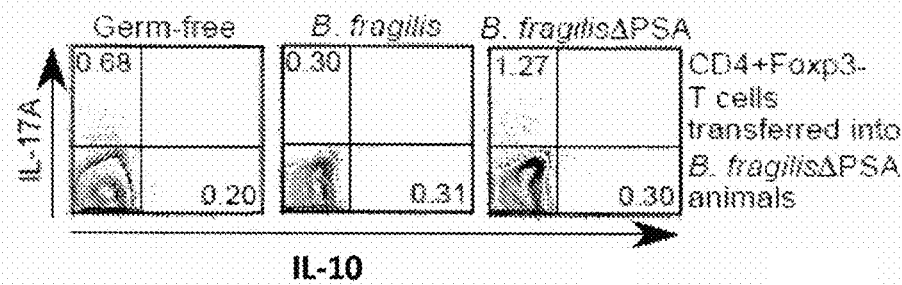

It was reasoned that during its lifelong colonization of the mammalian intestine, B. fragilis (and presumable other symbionts) must be tolerated as 'self' in order to prevent deleterious inflammation in the host. Therefore, it was hypothesized that PSA may have evolved to allow immunologic tolerance to B. fragilis antigens by suppressing Th 17 responses. Consistent with published literature (21,23), germ-free animals have virtually no Th 17 cells within the colon when compared with conventionally colonized animals (FIG. 4A and FIG. 6C) (FIG. 9A). While B. fragilis mono-associated animals do not significantly elicit Th 17 cells within the colon, the absence of PSA results in substantially increased intestinal Th 17 cell responses. Colonic lamina propria lymphocytes isolated from B. fragilisΔPSA mono-associated animals have increased secretion of IL-17A (FIG. 4A)(FIG. 9A) and elevated transcription of RORγT, the Th 17-specific lineage differentiation factor (FIG. 4D)(FIG. 7C). Additionally, CD4+Foxp3-T cells purified from the MLNs of B. fragilisΔPSA colonized animals have increased IL-17A and RORγT levels (FIG. 4C and FIG. 4D).

No signs of colitis were observed in animals with increased Th 17 cells Th 17 cell differentiation occurs in response to T cell receptor stimulation in the presence of TGF-β and IL-6. To determine the magnitude of T cell responses from differentially colonized animals, CD4+ T cells were purified from MLNs and assayed for the capacity of cells to produce IL-17A during in vitro Th 17 skewing assays. Cells from B. fragilis mono-associated animals have equivalent levels of IL-17A production as germ-free animals, even in the presence of TGF-β and IL-6. Most notably, CD4+ T cells from animals colonized with B. fragilis missing PSA (B. fragilisΔPSA) display significantly increased levels of IL-17A production compared to cells recovered from wild-type colonized animals) (FIG. 4E).

Figure 8F:
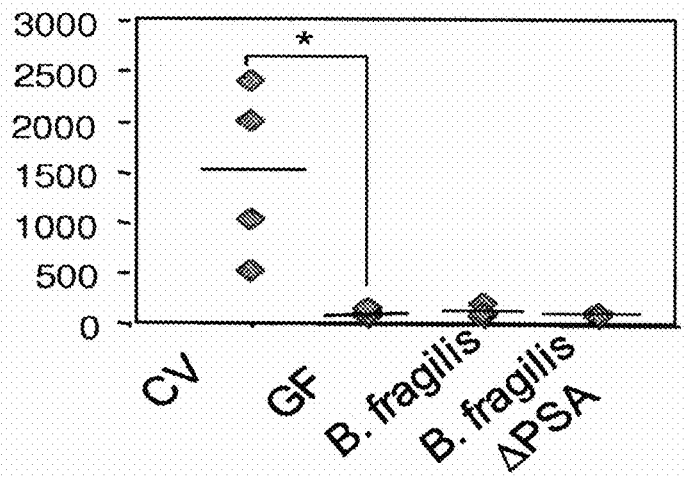

These data indicate that T cells isolated from B. fragilis mono-associated animals are intrinsically resistant to Th 17 differentiation. ATP has recently been demonstrated as a mechanism by which the intestinal microbiota can initiate development of Th 17 cells within the intestine (23). While elevated levels of luminal ATP are consistently found in conventionally colonized animals, germ-free and B. fragilis mono-associated animals have significantly lower levels of ATP that is not changed by the absence of PSA, ruling out a role for ATP dysregulation as a cause of the increased IL-17 seen in B. fragilisΔPSA animals (FIG. 8F). These data reveal that a commensal bacterium of the human microbiome can indeed induce an intestinal immune response similar to a pathogen. However, through the dedicated production of PSA, proinflammatory Th 17 development against B. fragilis is actively suppressed, supporting a model by which PSA-mediated tolerance, and not immunologic ignorance, prevents Th 17 responses to B. fragilis.

Figure 4F:
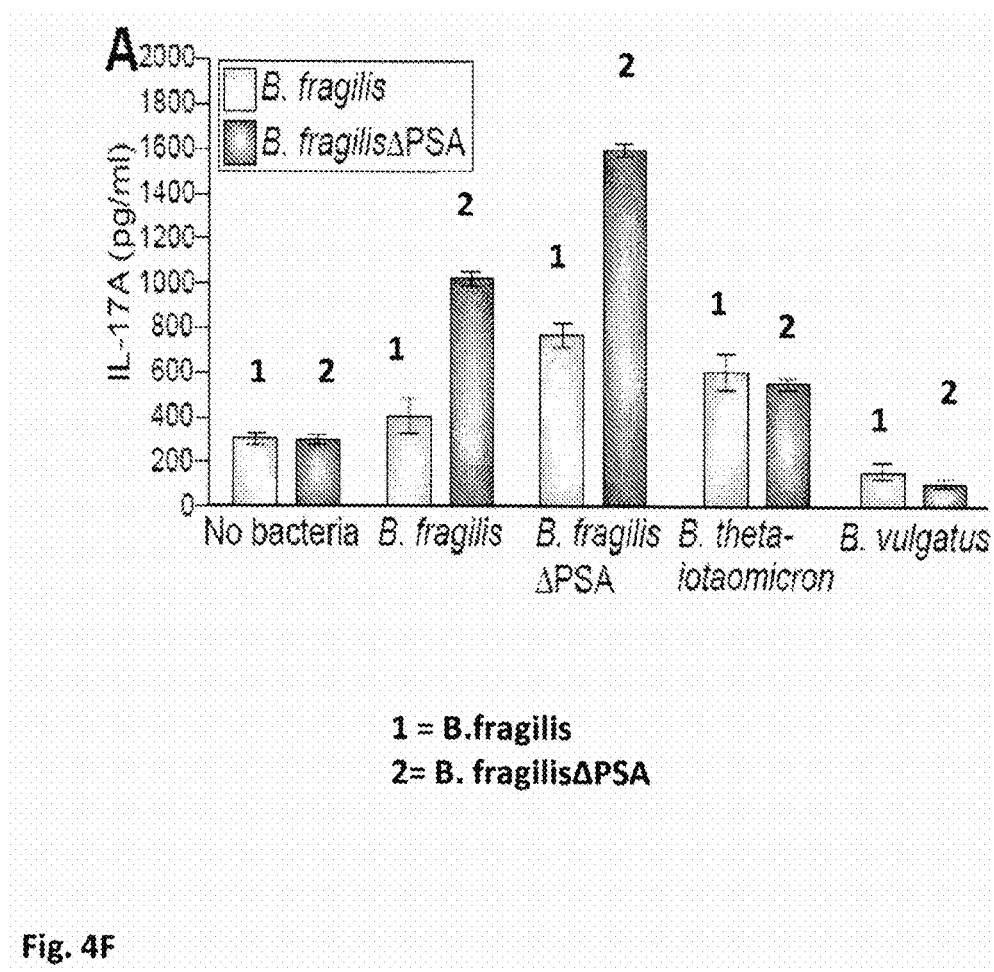

The data demonstrate that B. fragilis is not simply ignored by the host immune system, but rather actively induces a tolerogenic intestinal environment through its dedicated production of PSA. It was wondered if the host inflammatory response that ensues in the absence of PSA represents non-specific immune cell priming or is directed toward B. fragilis. To test this notion, pro-inflammatory immune responses by intestinal cells were measured from either B. fragilis or B. fragilisΔPSA mono-associated animals that were challenged with autologous or heterologous commensal bacteria. Isolated colonic lamina propria cells were activated with antigen presenting cells (APCs) pulsed with various strains of heat-killed commensal bacteria, and IL-17 production from these cultures was analyzed. Minimal IL-17 induction was detected in the absence of antigen (no bacteria) (FIG. 4F). Moreover, the addition of antigens provided by incubation of APCs with Bacteroides thetaiotaomicron or Bacteroides vulgatus elicited only basal levels of IL-17 by cells isolated from either B. fragilis or B. fragilisΔPSA mono-associated animals.

Remarkably, while lamina propria cells from colons of B. fragilis mono-associated animals induced little IL-17 in response to B. fragilis-derived antigens, cells isolated from mice colonized with B. fragilisΔPSA elicit significant amounts of IL-17 following stimulation with B. fragilis (and not other closely related Bacteroides species). Furthermore, IL-17 production by cells from B. fragilisΔPSA colonized animals was lower when APCs were pulsed with wild-type B. fragilis, indicating that PSA has anti-inflammatory properties in vitro, as previously reported (27). Enhanced IL-17 production by B. fragilisΔPSA cells is observed in MLNs as well (FIG. 4E). Therefore the findings reveal that in the absence of PSA, the host mounts an inflammatory response exclusively toward B. fragilis, suggesting that this commensal bacterium evolved PSA to suppress inflammation toward itself during host-bacterial mutualism.

Example 8. Th 17 Cell Responses to B. Fragilis are Antigen-Specific

It was wondered if the host inflammatory response that ensues in the absence of PSA represents non-specific T cell activation or is directed toward antigens of B. fragilis. To distinguish between these two possible mechanisms, IL-17 production by T cells was measured from either B. fragilis or B. fragilisΔPSA colonized animals to antigens of various commensal bacteria. Antigen presenting cells (APCs) were pulsed with bacterial extracts, and co-cultured with lamina propria lymphocytes harvested from animals colonized with B. fragilis or B. fragilisΔPSA. No additional stimulation was added, faithfully measuring antigen-specific responses. Minimal IL-17 induction was detected in the absence of bacteria (FIG. 9A).

APCs pulsed with Bacteroides thetaiotaomicron or Bacteroides vulgatus antigens elicited only basal levels of IL-17 by cells from both B. fragilis and B. fragilisΔPSA mono-associated animals. Moreover, equivalent IL-17 production between both groups shows that cells from B. fragilisΔPSA colonized mice are not more reactive to non-B. fragilis antigens. Astonishingly, while cells from wild-type B. fragilis mono-associated animals induced negligible responses, mice colonized with B. fragilisΔPSA elicited significant amounts of IL-17 following co-culture with B. fragilis-pulsed APCs (but not other closely related Bacteroides species). Consistent with previous studies, responses are lower when APCs are pulsed with wild-type B. fragilis compared to B. fragilisΔPSA, indicating that PSA has anti-inflammatory activity during in vitro cell cultures (Mazmanian et al., 2008). Equally enhanced IL-17 production from B. fragilisΔPSA animals is observed in cells from MLNs as well (FIG. 9A). These findings reveal that in the absence of PSA, the host mounts an inflammatory IL-17 response selectively toward B. fragilis antigens.

The data suggest that Th17 cell responses to B. fragilis antigens develop in the absence of PSA. To test this concept in vivo, germ-free mice were reconstituted with bone marrow from Foxp3-GFP animals and left germ-free, or mono-associated with either B. fragilis or B. fragilisΔPSA. This approach allows Th 17 cell induction in the presence or absence of PSA. CD4+Foxp3-effector T cells were purified from all 3 colonized groups and transferred into B. fragilisΔPSA mono-colonized Rag-deficient animals. Th 17 cell responses were analyzed as a measure of T cell reactivity to B. fragilis antigens. Effector T cells derived from B. fragilis mono-associated animals had minimal expression of Th 17 cells when transferred to animals that were colonized with B. fragilisΔPSA (FIG. 5A), indicating negligible reactivity toward B. fragilis antigens. However, mice receiving cells from B. fragilisΔPSA colonized donors elicited a significant increase in the percentage of Th 17 cells upon re-exposure to B. fragilis antigens. These data show that in vivo Th 17 cell development to B. fragilis antigens is prevented by PSA.

Example 9. PSA Suppresses Antigen-Specific IgA Responses Against B. fragilis

Figure 11:
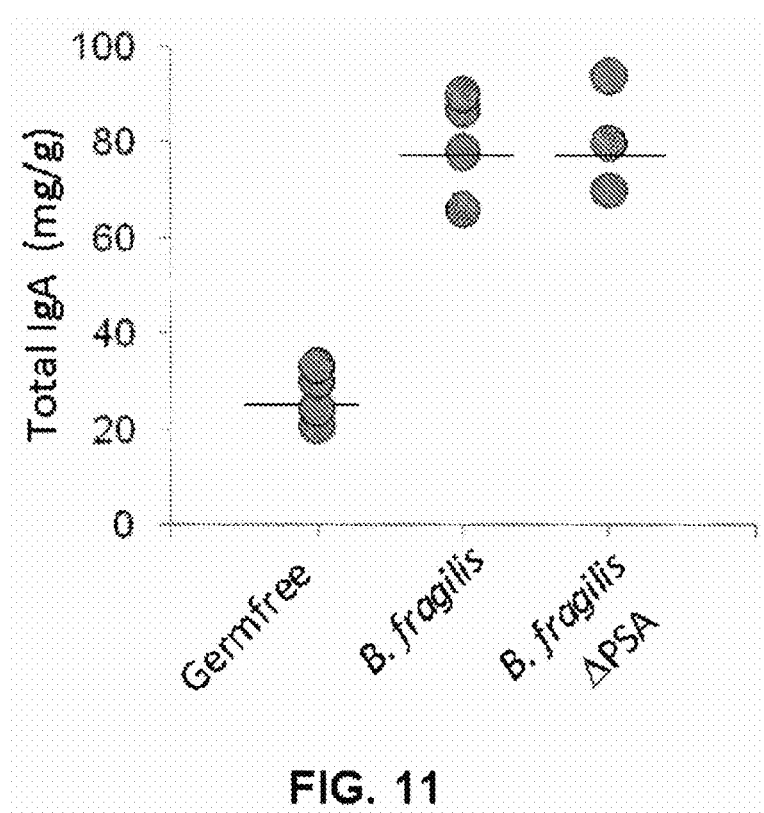
FIG. 11 provides further evidence that adaptive immune responses to *B. fragilis* are antigen specific.

Mucosal immunoglobulin A (IgA) is produced toward gut bacteria during colonization (Slack et al., 2009); therefore it was asked if PSA also prevents the development of anti-B. fragilis antibody production. Levels of B. fragilis-specific IgA were measured in animals mono-associated with *B. fragilis, B. fragilis*ΔPSA, or the closely related species *B. thetaiotaomicron* and *B. vulgatus*. Intestinal antibody responses were highly specific as colonic antibody isolated from either germ-free, *B. thetaiotaomicron* or *B. vulgatus* mono-colonized animals had no reactivity to *B. fragilis* antigens (FIG. 4F). Additionally, intestinal IgA from *B. fragilis* mono-associated animals did not react to antigens from *B. thetaiotaomicron* or *B. vulgatus* (FIG. 11D). Consistent with the findings of increased T cell responses, animals colonized with *B. fragilis*ΔPSA displayed elevated levels of *B. fragilis*-specific IgA contrary to *B. fragilis* expressing PSA (FIG. 11C).

To determine the nature of the antigens recognized by the host in the *B. fragilis*ΔPSA colonized animals, bacterial extracts were separated on a polyacrylamide gel and probed with IgA from either *B. fragilis* or *B. fragilis*ΔPSA mono-associated animals. IgA isolated from *B. fragilis* colonized animals is species specific, as no reactivity is seen to antigens from *B. thetaiotaomicron* or *Escherichia coli* (FIG. 4F). A greater number and higher intensity of antigenic species were detected when *B. fragilis* extracts were probed with IgA isolated from *B. fragilis*ΔPSA mono-associated animals compared to wild-type colonized mice (FIGS. 10A-E). Moreover, total IgA levels are not significantly different between *B. fragilis* or *B. fragilis*ΔPSA colonized animals (FIGS. 12A-E), demonstrating specific increases in reactivity to *B. fragilis* antigens only. Taken together, these data demonstrate that *B. fragilis* evolved PSA to suppress antigen-specific adaptive immunity during host-bacterial mutualism and that the Treg activation triggered by PSA is specific to *B. fragilis*.

Figure 12A:
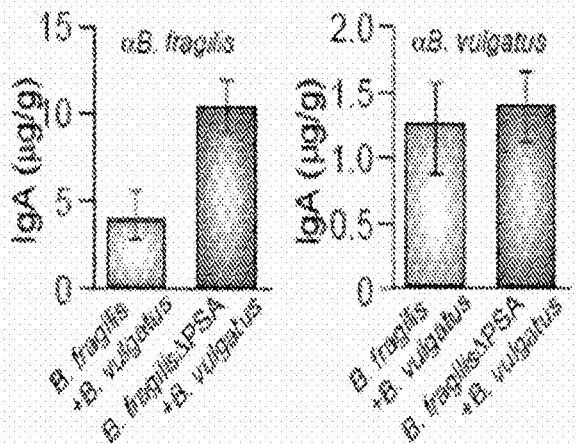
FIGS. 12A-E show PSA-mediated tolerance to *B. fragilis* but not other bacteria.
Figures 12B, 12C:
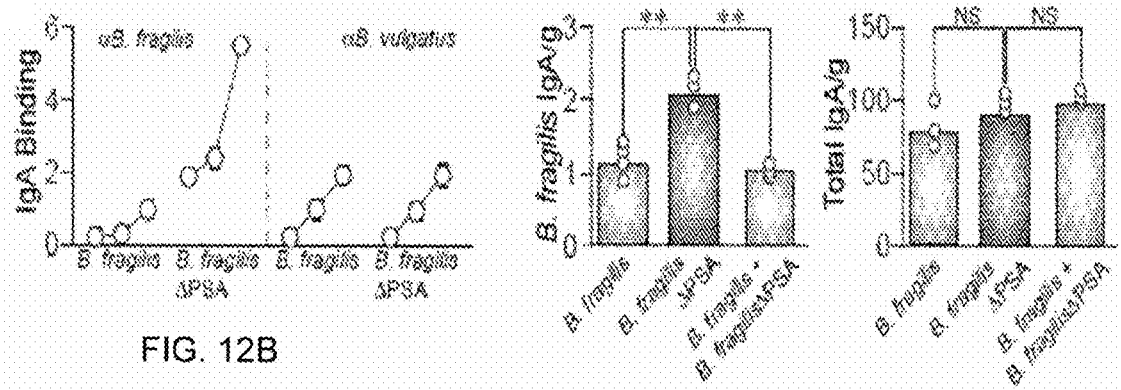
Figures 12D, 12E:
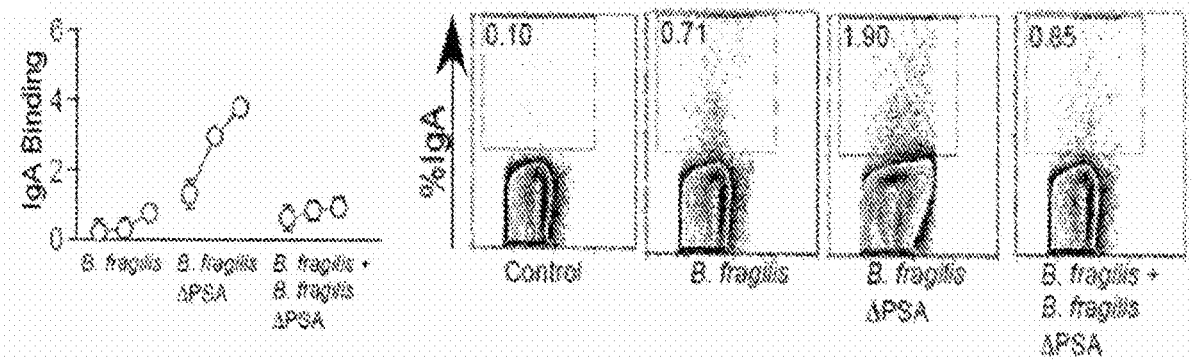
Figure 13A:
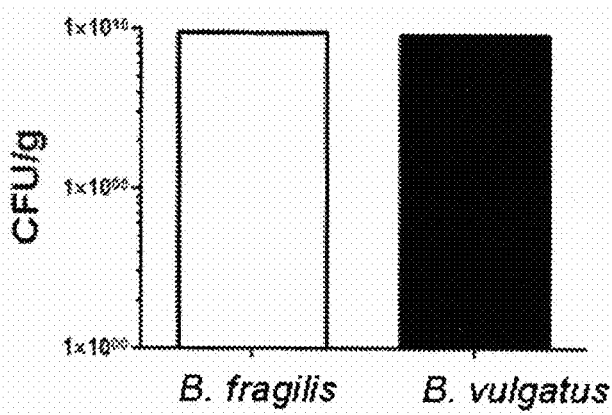
FIGS. 13A-C show the PSA-mediated antigen specific tolerance to *B. fragilis* during complex intestinal colonization.
Figure 13B:
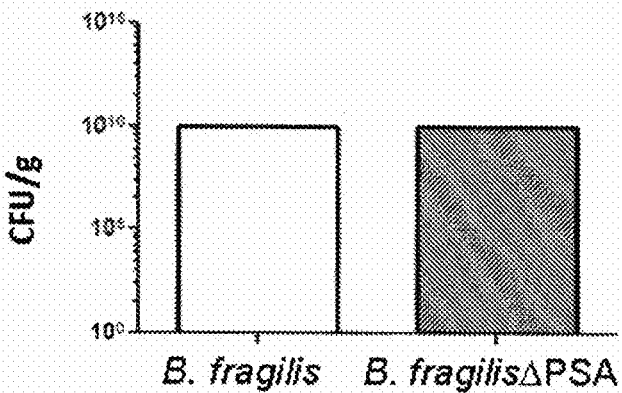
Figure 13C:
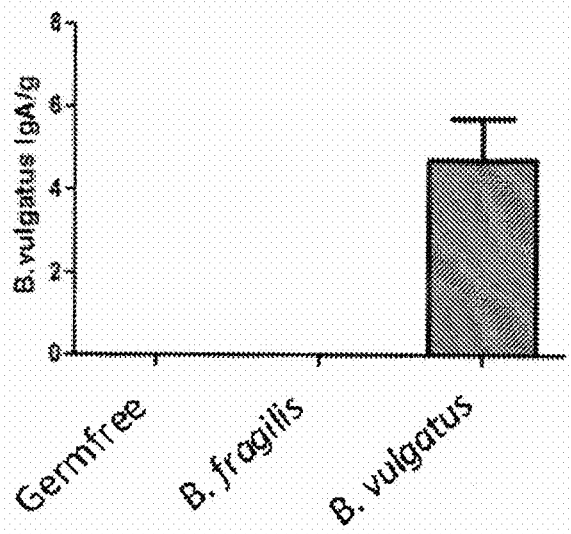

Example 10. PSA Prevents IgA Responses to *B. Fragilis* but not Other Commensal Bacteria and Actively Engenders Antigen Specific Mucosal Tolerance Mono-association studies are informative in determining antigen-specificity of immune responses. The findings show that PSA suppresses adaptive immunity to *B. fragilis*, however they can be interpreted as: 1) PSA induces tolerance specifically to *B. fragilis* antigens; 2) PSA induces a tolerant immune environment to antigens of other bacteria. To distinguish between these two possibilities, animals were co-colonized with *B. fragilis* and *B. vulgatus*, and IgA responses were measured to both organisms residing in the same microbiota. *B. fragilis* and *B. vulgatus* colonize animals to equal levels (FIGS. 12A-E). While antibody levels for *B. fragilis* antigens were again suppressed by PSA during co-colonization, the presence or absence of PSA had no effect on IgA reactivity to *B. vulgatus* (FIGS. 13A-C). Antibody responses are specific as soluble colonic contents isolated from germfree or *B. fragilis* mono-associated animals do not react to antigens derived from *B. vulgatus* (FIGS. 13A-C). Using a quantitative flow-cytometry based assay, it was determined that animals colonized with *B. fragilis*ΔPSA generate remarkably more IgA to *B. fragilis* surface antigens (FIGS. 12B and 12C). Low levels of binding are likely due to phase variation of surface antigens (Liu et al., 2008). No difference in binding to *B. vulgatus* antigens was observed during co-colonization with either wild-type or *B. fragilis*ΔPSA (FIGS. 12B, 12C and 13), demonstrating that PSA is unable to promote tolerance to antigens of other commensal bacteria residing in the same microbiota. These results establish that PSA does not induce a general, tolerogenic immune environment in the gut during homeostatic colonization.

Foxp3+ Tregs suppress through dominant tolerance. If PSA induces Tregs that mediate tolerance to *B. fragilis* antigens, then wild-type bacteria should induce Tregs that prevent reactions to antigens of *B. fragilis*ΔPSA. Remarkably, when animals harbor both wild-type and *B. fragilis*ΔPSA in equivalent numbers (FIG. 11), no increases in IgA reactivity to *B. fragilis* antigens are observed (FIGS. 12A-E), showing that PSA-producing bacteria prevent reactions to *B. fragilis* cells lacking PSA. The levels of *B. fragilis*-specific IgA during co-colonization are equivalent to that of wild-type mono-colonized animals, and are specific as total IgA levels are not altered (FIG. 1*l*). Furthermore, IgA recognition to *B. fragilis* antigens is not elevated during co-colonization using a quantitative FC assay (FIG. 12E). Based on this evidence, it is concluded that PSA expressed by *B. fragilis* mediates dominant tolerance to its antigens, but not to *B. vulgatus* antigens found in the same microbiota. Collectively, the studies confirm that PSA actively engenders antigen-specific mucosal tolerance.

Example 11. Foxp3+ Tregs are Required for Suppression of Adaptive Immunity to *B. fragilis*

To verify that Foxp3+ Tregs provide the mechanism for PSA-mediated suppression of adaptive immune responses, Th 17 and IgA responses to *B. fragilis* colonization following specificity ablation of CD4+Foxp4+ T cells was examined. Foxp3-DTR mice express the diphtheria toxin receptor (DTR) under the control of the Foxp3 promoter. Treatment of mice with diphtheria toxin (DT) results in ablation of Foxp3+ T cells and allows for functional analysis of Tregs in vivo (Kim et al., 2007). Consistent with previous findings (in Figured 14A-E), Foxp3-DTR reconstituted germ-free animals colonized with *B. fragilis*ΔPSA harbor increased Th 17 cells in both the colon (LP) and MLN when compared with animals colonized with wild-type *B. fragilis* (FIGS. 14A and 14B; left panels, -DT).

Figure 14D:
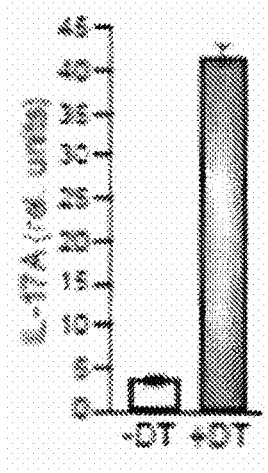
Figure 14E:
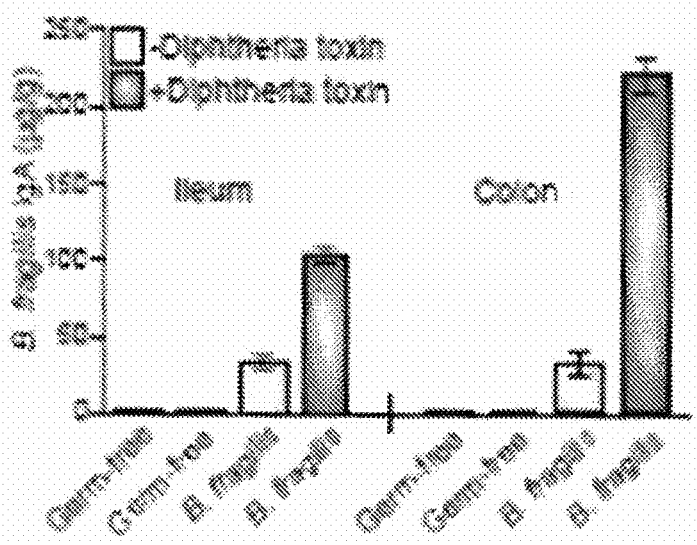

This difference is Th 17-specific, as there is no effect on IFNg producing CD4+ T cells from the same tissues (FIG. 14C). Most importantly, Treg ablation in *B. fragilis* mono-associated animals results in a dramatic increase in Th 17 cells in both the colonic lamina propria and MLN, but does not enhance Th 17 responses in *B. fragilis*ΔPSA animals (FIG. 14B; right panels, +DT). IFNg production in both groups of mice equally increases in the MLN following DT treatment (FIG. 14B), again showing specificity for Th 17 responses. Th 17 cell levels actually decreased in *B. fragilis*ΔPSA colonized mice. Although this unusual phenotype cannot be explained, the results clearly show specific increases in Th 17 for wild-type bacteria as the percentage of CD4+IL-17+ cells increases only in this group following DT administration (FIG. 14A). Treatment of mice with diphtheria toxin (+DT) confirms nearly complete ablation of Foxp3+ T cells in animals (FIG. 14A). Accordingly, expression of IL-17A transcript in the colonic LP is significantly increased in DT-treated animals (FIG. 14D). These data reveal that PSA induces functional Foxp3+ Tregs that actively suppress Th 17 responses to *B. fragilis* during commensal colonization.

Figure 15A:
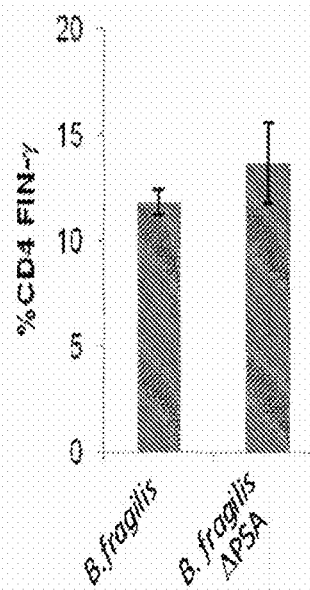
FIGS. 15A-C show further evidence that Foxp3+ Tregs are required for suppression of adaptive immunity to *B. fragilis*.
Figure 15B:
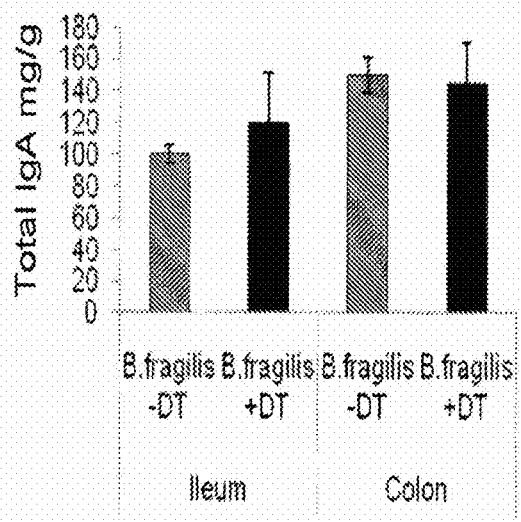
Figure 15C:
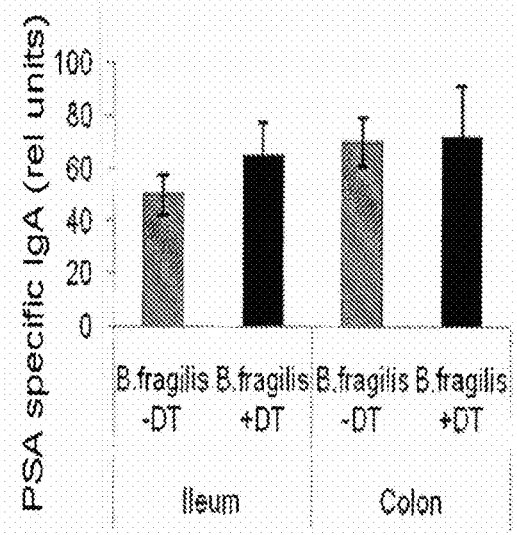

Finally, *B. fragilis*-specific antibody production in the presence or absence of Tregs was determined. *B. fragilis* mono-associated animals produce *B. fragilis*-specific antibodies in both the ileum and colon (FIGS. 15A-C). Upon Foxp3+ Treg ablation, *B. fragilis*-specific IgA increases significantly throughout the small and large intestine, with the greatest increase (over 10-fold) in the colon (FIGS. 15A-C). This reflects a quantitative increase in antigen-specific reactivity, as both PSA-specific and total IgA antibody production throughout the intestine is not affected by the absence of Tregs (FIGS. 15A-C). Collectively, it is shown that B. fragilis produces an immunomodulatory molecule that induces Treg cells in the gut, which suppress antigen-specific adaptive immune responses. These findings reveal a novel cellular and molecular mechanism for how mammals tolerate symbiotic bacterial molecules during host-bacterial commensalism.

Example 12: Immunomodulatory Capsular Polysaccharide PSA is Actively Sorted into OMVs of B. fragilis Ultrathin sections of EDL-enriched B. fragilis were prepared as described in materials and methods and imaged by transmission electron microscopy.

Figure 16:
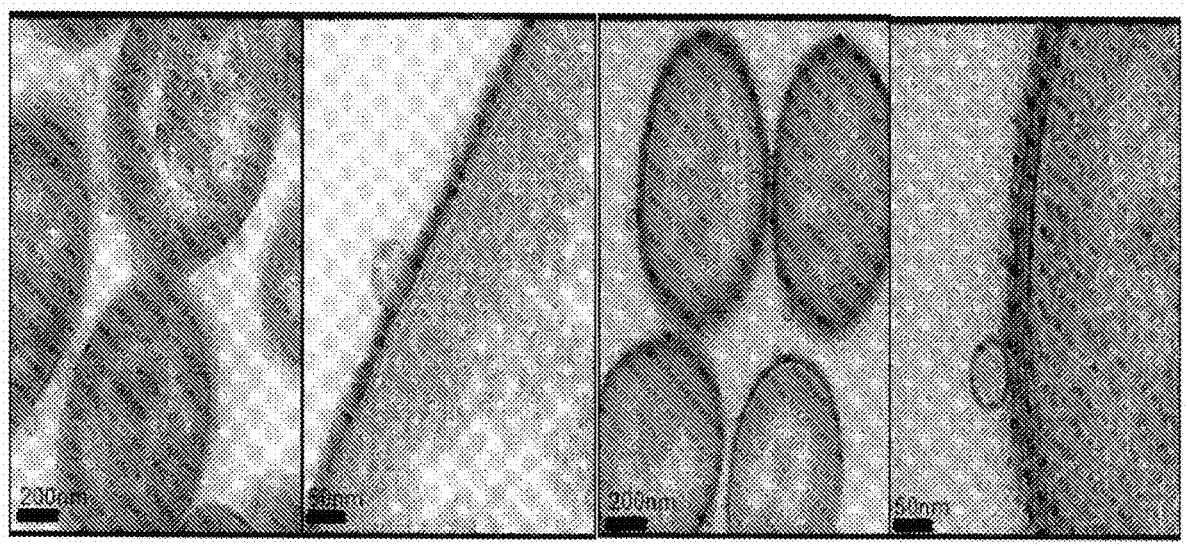
FIGS. 16A-C show that outer membrane vesicles from *Bacteroides fragilis* contain PSA.
Figure 16B:
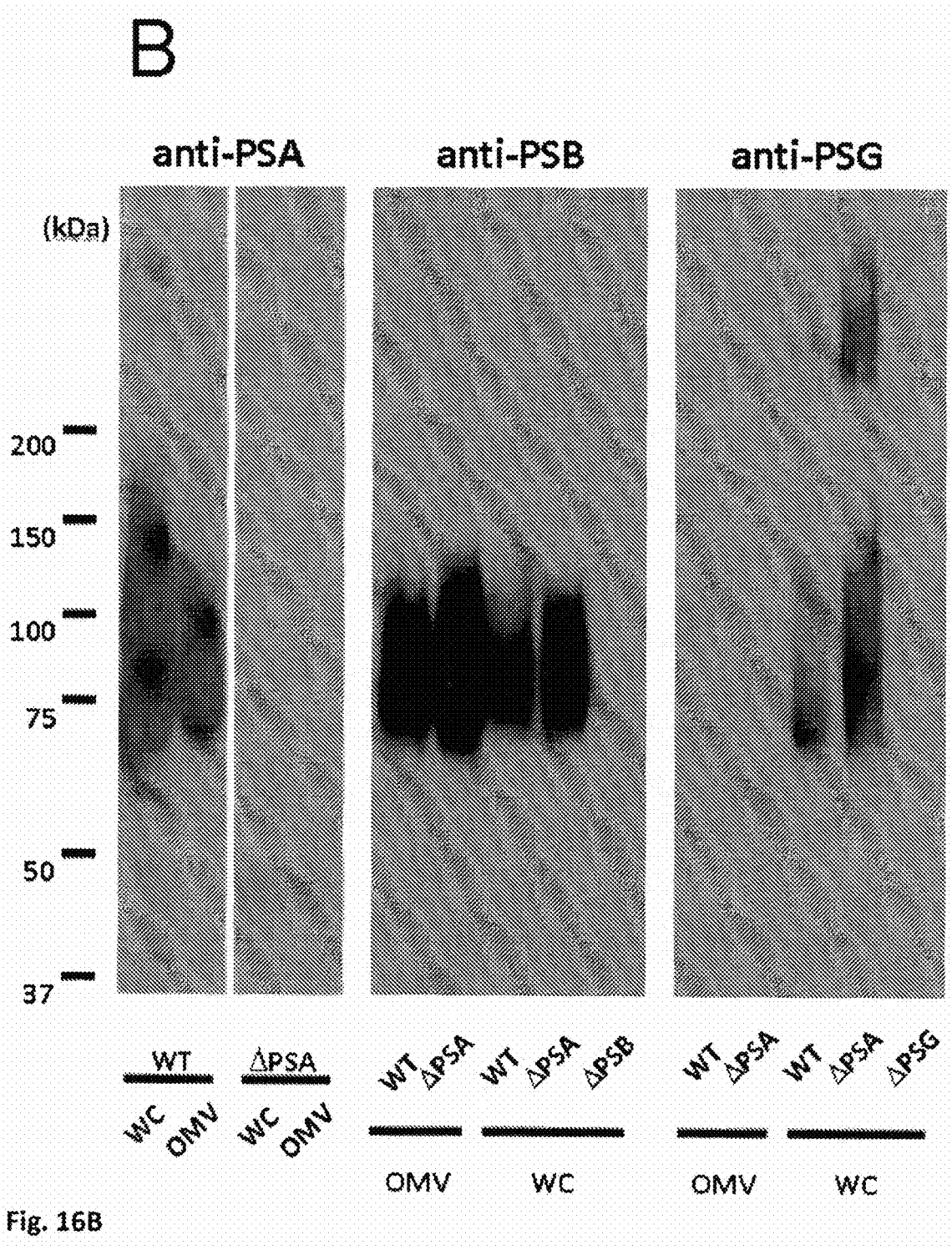
Figure 16C:
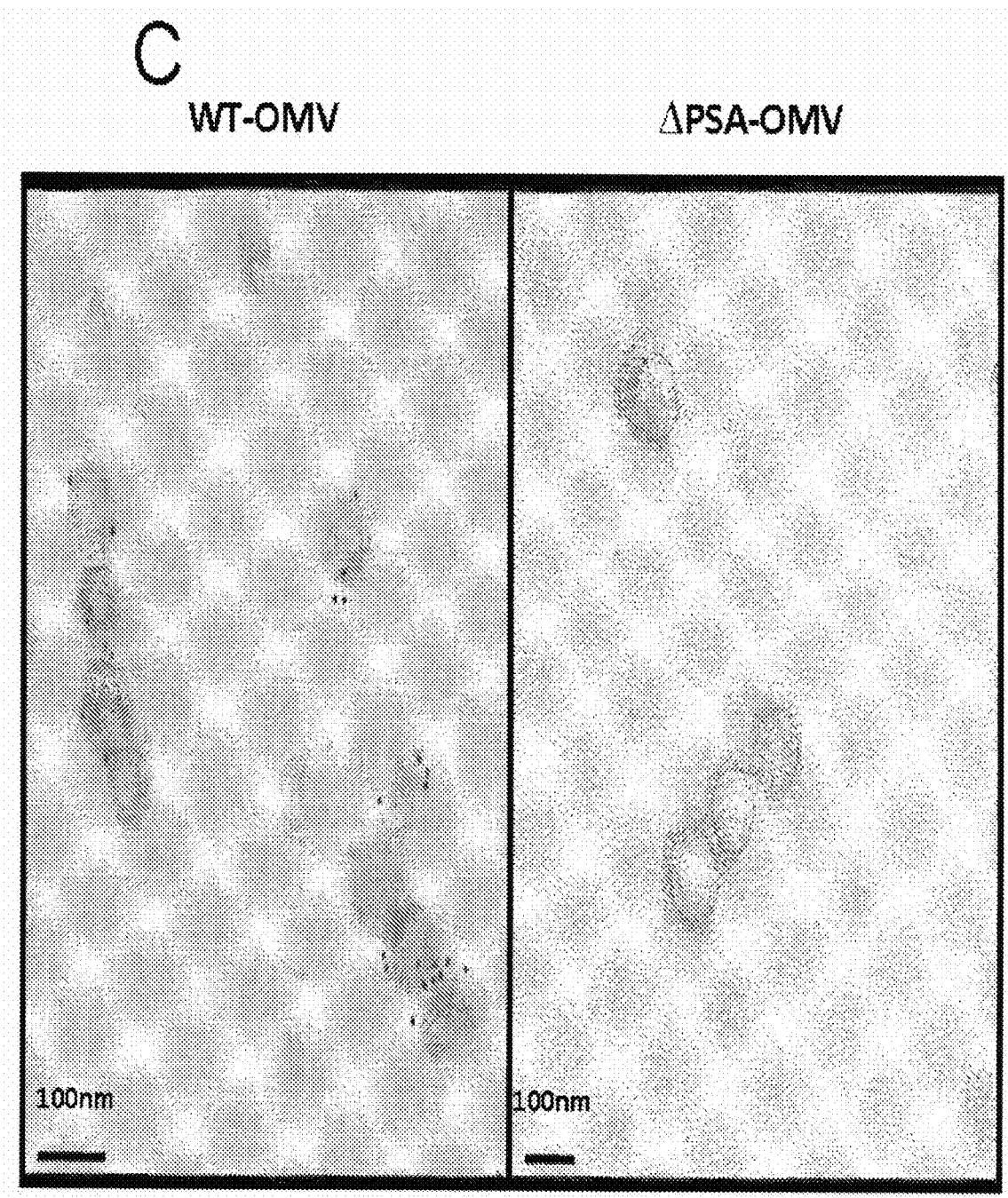

The results illustrated in FIGS. 16A-C show that OMVs were abundantly produced by bacteria, and could be observed budding from the bacterial envelope (FIG. 17A, higher magnification). Applicants' previous studies have shown that deletion of PSA abrogates the immunomodulatory capacity of B. fragilis (Mazmanian, Liu, Tzianabos, and Kasper (2005) An Immunomodulatory Molecule of Symbiotic Bacteria Directs Maturation of the Host Immune System. Cell 122:1 107-118.) (Mazmanian, Round, and Kasper (2008) A microbial symbiosis factor prevents intestinal inflammatory disease. Nature. 453 (7195) 620-625. Electron micrographs of a PSA mutant strain (B. fragilisΔPSA) illustrate no defect in OMV synthesis, and the size, shape and abundance of OMVs produced were indistinguishable from wild-type bacteria (FIG. 17A). In particular, the results illustrated in FIG. 17A reveal that vesicles are actively budding from the surface of bacteria.

To determine if PSA is associated with OMVs of B. fragilis, purified vesicles from wild-type and ΔPSA bacteria were subjected to immunoblot analysis as described in the materials and methods section.

The results illustrated in FIG. 16B show that the vesicles from wild-type displayed immunoreactivity for PSA, unlike OMV s from B. fragilisΔPSA. B. fragilis produces at least 8 distinct capsular polysaccharides which coat the surface of bacterial cells, named PSA-PSH. While PSB was also detected in vesicle preparations, PSG was absent, demonstrating selectivity for certain polysaccharides to be packaged with OMVs (FIG. 16B). Accordingly, the results of FIG. 16B show that PSA and PSB are associated with vesicles, while PSG is only found on the bacterial surface. Deletion mutants for capsular polysaccharides confirm specificity of each antiserum.

The results from immunoblot analysis were confirmed by experiments of immunogold labeling performed as described in the materials and methods section. The results of immunogold labeling of purified vesicles illustrated in FIG. 16C and confirm that PSA is physically associated with OMVs, and that the vast majority of OMVs from wild-type B. fragilis stain positively for PSA (data not shown). To verify that the absence of PSA did not alter the molecular composition of OMVs, a proteomic analysis was performed by mass spectrometry which revealed no major qualitative or quantitative differences in the protein composition between vesicles from wild-type or PSA-mutant bacteria (data not shown).

PSA is a heterogeneous polymer of repeating subunits. Size separation of PSA recovered from whole cell extracts by chromatography was performed as well as an immunoblot analysis with anti-PSA of capsular polysaccharide preparations from whole cells and purified OMVs as indicated in material and methods.

The relevant results illustrated in FIGS. 16A-C surprisingly show that only the low molecular weight species is associated with OMVs, illustrating specificity of PSA packaging into vesicles. In particular, the results of FIGS. 16A-C show that only low molecular weight PSA (LPSA) is packaged into vesicles unlike the high molecular weight (H-PSA) species that remains associated with the bacterial cell envelope.

Together, the above results reveal that the immunomodulatory capsular polysaccharide PSA is actively sorted into OMVs of B. fragilis.

Example 13: PSA Elicits IL-10 Production Through TLR2 Signaling Directly on a T Cell PSA was contacted with splenic cells or Bone marrow derived dendritic cells (BMDCs) co-cultured with CD4+ T cells purified from the spleen, in a series of experiments illustrated in FIGS. 17A to 17D. The results support the conclusion that PSA can elicit IL-10 production through TLR2 signaling on a T cell.

Example 14: PSA can Directly Signal Through TLR2 on a T Cell in the Absence of APC and this does not Require TLR 1 or TLR6

PSA was contacted with T cells isolated from wild-type (WT) TLR1-/-, TLR2-/-, TLR6-/-, or CD14-/- animals in a set of experiments illustrated in FIG. 18A-18B. The results indicate that PSA can directly stimulate the T cell (in the absence of an APC) to induce IL-10. Induction of IL-10 by PSA requires TLR2 but does not require TLR1 or TLR6. Since TLR2 does not act as a homodimer and is known to heterodimerize with TLR1 and TLR6 this indicates that PSA is acting uniquely through TLR2 to induce IL-10.

PSA was also contacted with BMDCs from WT, TLR1-/-, TLR2-/-, TLR6-/- and CD14-/- animals and with purified CD4+ T cells from WT mice in a set of experiments illustrated in FIGS. 18A-C. The results indicate that under the experimental conditions the ability of purified PSA to elicit IL-10 production does not depend on signaling through TLR1, TLR2, or TLR6 on the dendritic cell. However, according to these results IFN-γ production does require both TLR1 and TLR2 signaling on the dendritic cell.

Example 15: PSA is a Unique TLR2 Ligand

Figure 19:
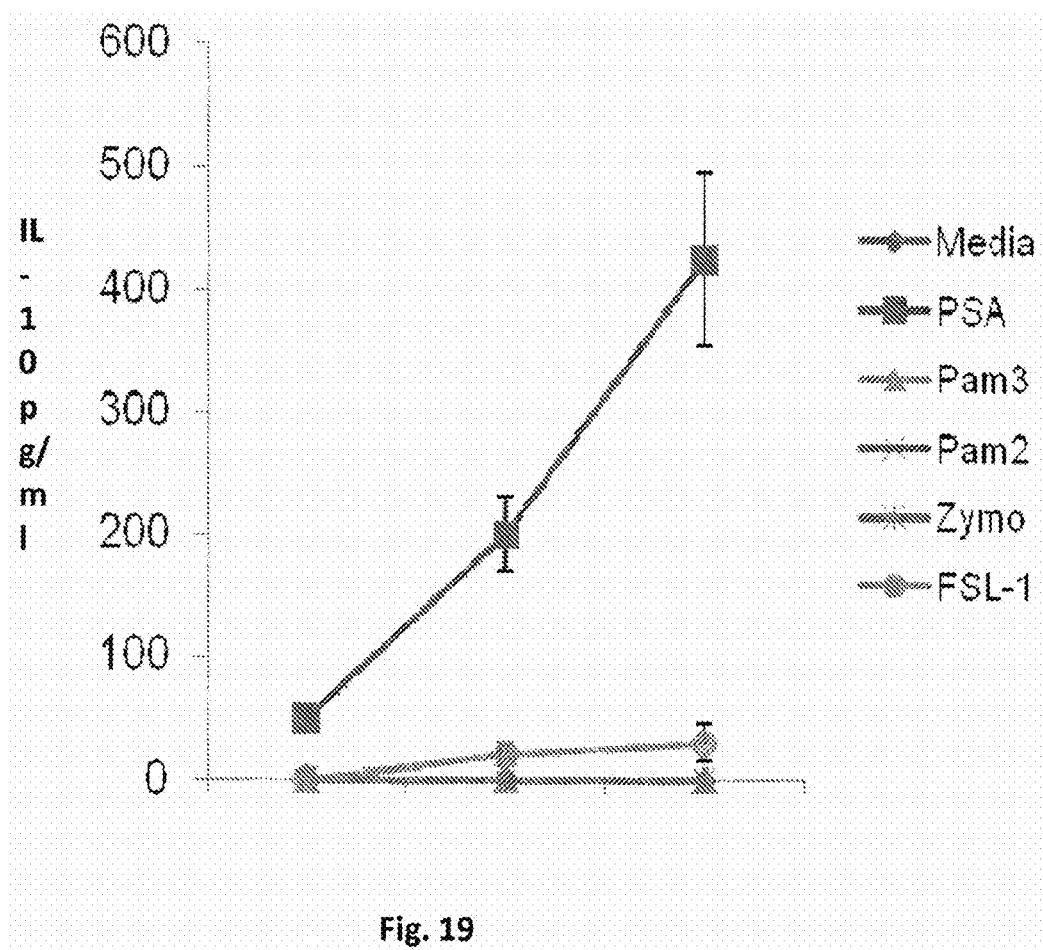
FIG. 19: PSA is a unique TLR2 ligand.

PSA. TLR1/TLR2 ligand PAM3CysK and TLR2/6 ligand FSL1 were contacted with CD4+ Foxp3- T cells in a set of experiments illustrated in FIG. 19. The results indicate that PSA can directly stimulate a non-Treg cell to produce IL-10. It does so uniquely as other TLR2 ligands like PAM3CysK do not induce IL-10 production from this same population of non-Treg cells. Additionally, other TLR2 ligands actually suppress IFN-γ production by the T cell again indicating the unique ability of PSA to activate a T cell.

Figure 20:
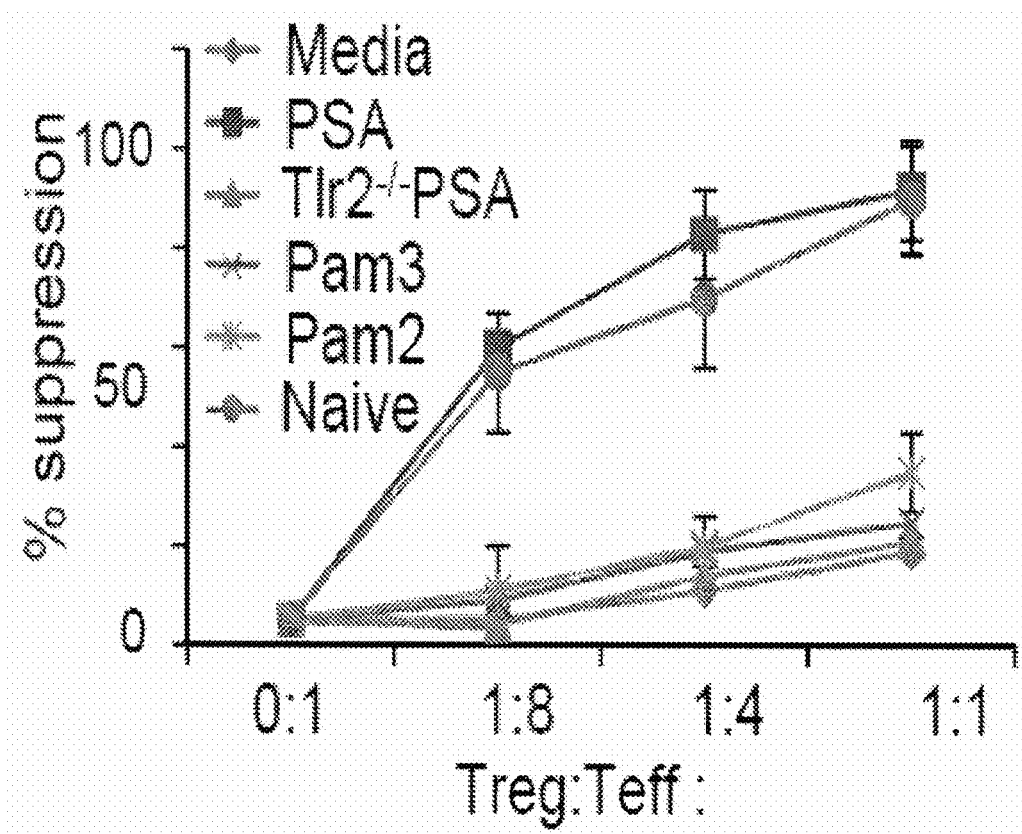
FIG. 20: PSA can enhance Treg function in vitro.

TLR 2 ligands, PSA, PAM3CysK, or FSL1 were contacted with CD4+ T cells in a set of experiments illustrated in FIG. 20. The results indicate that PSA elicits more IL-10 production from T cells in the absence of an APC than other known TLR2 ligands.

PSA was contacted with CD4+CD25-T cells from either WT or TLR2-/- animals in a set of experiments illustrated in FIG. 20. The results indicate that the induction of IL-10 by non-Treg cells by PSA is dependent on TLR2 signaling on the T cell.

Example 16: PSA can Directly Trigger a Treg to Produce IL-10 and Enhances the Survival of Tregs in an In Vitro Culture CD4+Foxp3+ T cells were stimulated with anti-CD3 in the presence of TGF-β and incubated with and without PSA in a set of experiments illustrated in FIG. 21. The results indicate that PSA can directly cause a Treg to induce gene expression of IL-10.

Figure 21:
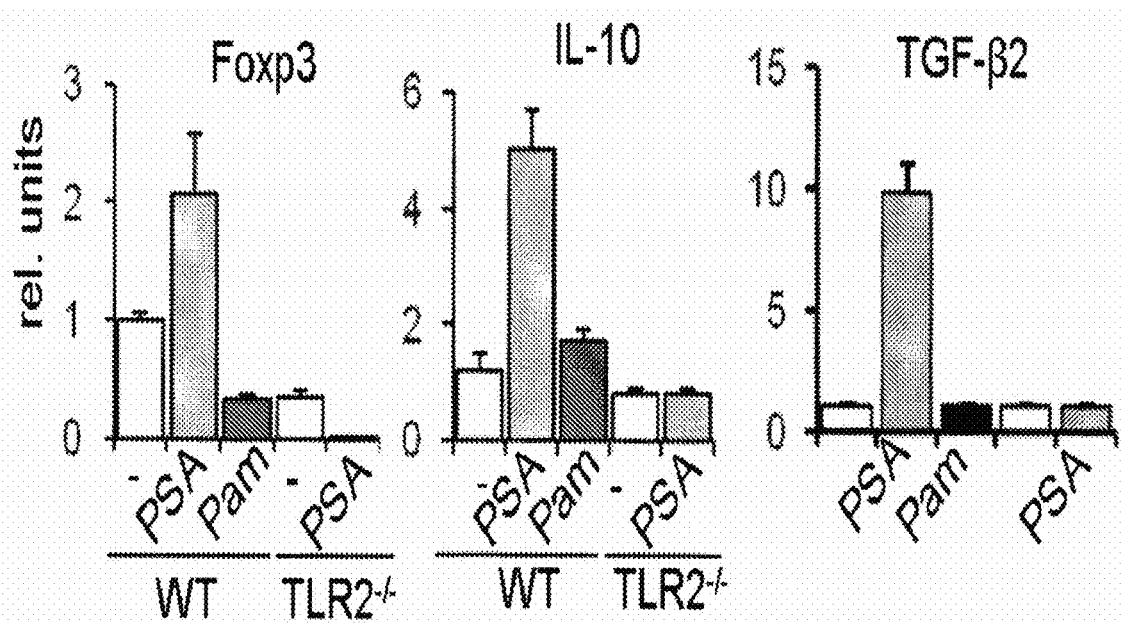
FIG. 21: PSA can directly trigger a Treg to produce IL-10 and TGF-β.

CD4+Foxp3+ T cells were incubated with BMDCs and the culture was stimulated with anti-CD3 and TGF-β in a set of experiments illustrated in FIG. 21. The results indicate that PSA can enhance the survival or proliferation of a Foxp3 expressing T regulatory cell in vitro The results illustrated in Examples 13 to 16 support the conclusions that 1) That PSA acts on TLR2 in the T cell to induce IL-10 but not IFNγ, 2) PSA does NOT require TLR 1 or TLR 6 on the T cell for IL-10 production; 3) PSA can directly act on a T cell to induce il-10 (no APCs needed), Also PSA seems to act differently than other TLR2 ligands (2 and 3 are important for highlighting the unique nature of PSA as a toll ligand; 4) PSAs ability to induce IL-10 directly on t cell is TLR2 dependent; 5) one exp shows PSA can convert to a higher degree in vitro (both % and absolute #); 6) PSA can induce IL-10 from purified Tregs as well and also seems to maintain/expand a cd4foxp3high population

*Bacteroides fragilis*, produces a bacterial molecule that can regulate host immunity to suppress inflammatory responses toward its own antigens, thereby resulting in host tolerance. Polysaccharide A (PSA) of *B. fragilis* induces a specific gene expression profile in functionally suppressive Foxp3+ regulatory T cells, and coordinates the establishment of a tolerogenic immune environment. Most notably, host cells recovered from animals colonized with *B. fragilis*ΔPSA are more reactive to *B. fragilis*, but not to other (closely related) commensal bacteria. These data demonstrate that the host immune system is not ignorant to the presence of *B. fragilis*, but rather that PSA is actively suppressing these inflammatory responses. It appears that commensal bacteria are not immunologically ignored, and induction of inflammation is a default response to foreign microorganisms (both commensal and pathogenic). Much like virulence factors employed by pathogens, it appears commensal bacteria have evolved symbiosis factors to control host immunity by programming the immune system to prevent antigen-specific responses during gut colonization. Conversely to pathogens, colonization by *B. fragilis* actually has beneficial consequences to the health of the host, as PSA protects animals from experimental colitis (26). Thus, *B. fragilis* is not only actively inducing its own tolerance, but also preserving the integrity of the niche it colonizes for life.

The examples set forth above are provided to give those of ordinary skill in the art a complete disclosure and description of how to make and use the embodiments of the Tregs, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Summary, Detailed Description, and Examples is hereby incorporated herein by reference. Further, the hard copy of the sequence listing submitted herewith and the corresponding computer readable form are both incorporated herein by reference in their entireties.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Although any methods and materials similar or equivalent to those described herein can be used in the practice for testing of the specific examples of appropriate materials and methods are described herein.

A number of embodiments of the disclosure have been described. Nevertheless, it will be understood that various modifications can be made without departing from the spirit and scope of the present disclosure. Accordingly, other embodiments are within the scope of the following claims.

REFERENCES

1. Atarashi, K., Nishimura, J., Shima, T., Umesaki, Y., Yamamoto, M., Onoue, M., Yagita, H., Ishii. N., Evans, R., Honda, K., et al. (2008). ATP drives lamina propria T(H) 17 cell differentiation. Nature 455, 808-812.
2. Barnes. M. J., and Powrie, F. (2009). Regulatory T cells reinforce intestinal homeostasis. Immunity 31, 401-411.
3. Bettelli, E., Carrier, Y., Gao, W., Korn, T., Strom, T. B., Oukka, M., Weiner, H. L., and Kuchroo, V. K. (2006). Reciprocal developmental pathways for the generation of pathogenic effector TH17 and regulatory T cells. Nature 441, 235-238.
4. Bouskra, D., Brezillon, C., Berard, M., Werts, C., Varona, R., Boneca, L G., and Eberl, G. (2008). Lymphoid tissue genesis induced by commensals through NOD 1 regulates intestinal homeostasis. Nature 456, 507-510.
5. Brunkow, M. E., et al., Nat Genet 27, 68 (2001).
6. Cash, H. L., Whitham, C. V., Behrendt, C. L., and Hooper, L. V. (2006). Symbiotic bacteria direct expression of an intestinal bactericidal lectin. Science 313, 1126-1130.
7. Chow, J., and Mazmanian, S. K. (2009). Getting the bugs out of the immune system: do bacterial microbiota "fix" intestinal T cell responses? Cell Host Microbe 5, 8-12.
8. Collison, L. W., Workman, C. J., Kuo, T. T., Boyd, K., Wang, Y., Vignali, K. M., Cross, R., Sehy, D., Blumberg, R. S., and Vignali, D. A. (2007). The inhibitory cytokine IL-35 contributes to regulatory T-cell function. Nature 450, 566-569.
9. Coombes, J. L., Siddiqui, K. R., Arancibia-Carcamo. C. V., Hall. J., Sun, C. M., Belkaid. Y., and Powrie, F. (2007).

A functionally specialized population of mucosal CD103+ DCs induces Foxp3+ regulatory T cells via a TGF-beta and retinoic acid-dependent mechanism. J Exp Med 204, 1757-1764.
10. Dong, C. (2006). Diversification of T-helper-cell lineages: finding the family root of IL17-producing cells. Nat Rev Immunol 6, 329-333.
11. Duerr, R. H. et al., Science 314, 1461 (2006).
12. Falk, P. G., Hooper, L. V., Midtvedt, T., and Gordon, J. I. (1998). Creating and maintaining the gastrointestinal ecosystem: what we know and need to know from gnotobiology. Microbial Mol Biol Rev 62, 1157-1170.
13. Fontenot, J. D., Gavin, M. A., and Rudensky, A. Y. (2003). Foxp3 programs the development and function of CD4+CD25+ regulatory T cells. Nat Immunol 4, 330-336.
14. Fontenot, J. D., Rasmussen, J. P., Williams, L. M., Dooley, J. L., Farr, A. G., and Rudensky, A. Y. (2005). Regulatory T cell lineage specification by the forkhead transcription factor foxp3. Immunity 22, 329-341.
15. Gaboriau-Routhiau, V., Rakotobe, S., Lecuyer, E., Mulder, I., Lan, A., Bridonneau, C., Rochet, V., Pisi, A., De Paepe, M., Brandi, G., et al. (2009). The key role of segmented filamentous bacteria in the coordinated maturation of gut helper T cell responses. Immunity 31, 677-689.
16. Gondek, D. C., Lu, L. F., Quezada, S. A., Sakaguchi, S., and Noelle, R. J. (2005). Cutting edge: contact-mediated suppression by CD4+CD25+ regulatory cells involves a granzyme B-dependent, perforin-independent mechanism. J Immunol 174, 1783-1786.
17. Hall, J. A., Bouladoux, N., Sun, C. M., Wohlfert, E. A., Blank, R. B., Zhu, Q., Grigg, M. E., Berzofsky, J. A., and Belkaid, Y. (2008). Commensal DNA limits regulatory T cell conversion and is a natural adjuvant of intestinal immune responses. Immunity 29, 637649.
18. Hampe, J., Cuthbert, A., Croucher, P. J., Mirza, M. M., Mascheretti, S., Fisher, S., Frenzel, H., King, K., Hasselmeyer, A., MacPherson, A J., et al. (2001). Association between insertion mutation in NOD2 gene and Crohn's disease in German and British populations. Lancet 357, 1925-1928.
19. Hampe, J., Franke, A., Rosenstiel, P., Till, A., Teuber, M., Huse. K., Albrecht, M., Mayr, G., De La Vega. F. M., Briggs, J., et al. (2007). A genome-wide association scan of nonsynonymous SNPs identifies a susceptibility variant for Crohn disease in ATG16LI. Nat Genet 39, 207-211.
20. He. B., Xu, W., Santini, P. A., Polydorides. A. D., Chiu. A., Estrella, J., Shan. M., Chadburn, A., Villanacci, V., Plebani, A., et al. (2007). Intestinal bacteria trigger TI cell-independent immunoglobulin A(2) class switching by inducing epithelial-cell secretion of the cytokine APRIL. Immunity 26, 812-826.
21. Hooper, L. V. (2009). Do symbiotic bacteria subvert host immunity? Nat Rev Microbial 7, 367-374.
22. Hooper, L. V., and Gordon, J. I. (2001). Commensal host-bacterial relationships in the gut. Science 292, 1115-1118.
23. Hori, S., Nomura, T., and Sakaguchi, S. (2003). Control of regulatory T cell development by the transcription factor Foxp3. Science 299, 1057-1061.
24. Ishikawa, H. et al., Clin Exp Immunol 153, 127 (2008).
25. Ivanov, I I et al., Cell 126, 1121 (2006).
26. Ivanov, I I, Atarashi, K., Manel, N., Brodie, E. L., Shima, T., Karaoz, U., Wei, D., Goldfarb, K. C., Santee, C. A., Lynch, S. V., et al. (2009). Induction of intestinal Th17 cells by segmented filamentous bacteria. Cell 139, 485-498.
27. Ivanov, I I, Frutos Rde, L., Manel, N., Yoshinaga, K., Rifkin. D. B., Sartor, R. B., Finlay, B. B., and Littman, D. R. (2008). Specific microbiota direct the differentiation of IL-17 producing T-helper cells in the mucosa of the small intestine. Cell Host Microbe 4, 337349.
28. Izcue, A., Coombes, J. L., and Powrie, F. (2009). Regulatory lymphocytes and intestinal inflammation. Annu Rev Immunol 27, 313-338.
29. Kim, J. M., Rasmussen, J. P., and Rudensky, A. Y. (2007). Regulatory T cells prevent catastrophic autoimmunity throughout the lifespan of mice. Nat Immunol 8, 191-197.
30. Koch, M. A., Tucker-Heard, G., Perdue, N. R., Killebrew, J. R., Urdahl, K. B., and Campbell, D. J. (2009). The transcription factor T-bet controls regulatory T cell homeostasis and function during type 1 inflammation. Nat Immunol 10, 595-602.
31. Ley, R. E., Peterson, D. A., and Gordon, J. I. (2006). Ecological and evolutionary forces shaping microbial diversity in the human intestine. Cell 124, 837-848.
32. Ley, R. E., et al., Science (2008).
33. Lin, W., Haribhai, D., Relland, L. M., Truong, N., Carlson, M. R., Williams, C. B., and Chatila, T. A. (2007). Regulatory T cell development in the absence of functional Foxp3. Nat Immunol 8, 359-368.
34. Liu, C. H., Lee. S. M., Vanlare, J. M., Kasper, D. L., and Mazmanian, S. K. (2008). Regulation of surface architecture by symbiotic bacteria mediates host colonization. Proc Natl Acad Sci USA 105, 3951-3956.
35. Liu, H., Komai-Koma, M., Xu, D., and Liew, F. Y. (2006). Toll-like receptor 2 signaling modulates the functions of CD4+ CD25+ regulatory T cells. Proc Natl Acad Sci USA 103, 7048-7053.
36. Macpherson, A. J., and Harris, N. L. (2004). Interactions between commensal intestinal bacteria and the immune system. Nat Rev Immunol 4, 478-485.
37. Macpherson, A J., and Uhr, T. (2004). Induction of protective IgA by intestinal dendritic cells carrying commensal bacteria. Science 303, 1662-1665.
38. Maier, B. R., and Hentges, D. J. (1972). Experimental *Shigella* infections in laboratory animals. I. Antagonism by human normal flora components in gnotobiotic mice. Infect Immun 6, 168-173.
39. Maynard, C. L., Harrington, L. E., Janowski, K. M., Oliver, J. R., Zindl, C. L., Rudensky, A. Y., and Weaver, C. T. (2007). Regulatory T cells expressing interleukin 10 develop from Foxp3+ and Foxp3-precursor cells in the absence of interleukin 10. Nat Immunol 8, 931941.
40. Mazmanian, S. K., Liu, C. H., Tzianabos, A. O., and Kasper, D. L. (2005). An immunomodulatory molecule of symbiotic bacteria directs maturation of the hostimmune system. Cell 122, 107-118.
41. Mazmanian, S. K., Round, J. L., and Kasper, D. L. (2008). A microbial symbiosis factor prevents intestinal inflammatory disease. Nature 453, 620-625.
42. Min, B., Thornton, A., Caucheteux, S. M., Younes, S. A., Oh, K., Hu-Li, J., and Paul, W. E. (2007). Gut flora antigens are not important in the maintenance of regulatory T cell heterogeneity and homeostasis. Eur J Immunol 37, 1916-1923.
43. Rakoff-Nahoum, S., Paglino, J., Eslami-Varzaneh, F., Edberg, S., and Medzhitov, R. (2004). Recognition of commensal microflora by toll-like receptors is required for intestinal homeostasis. Cell 118, 229-241.

44. Rescigno, M. et al., Nat Immunol 2, 361 (2001).
45. Round, J. L., Mazmanian, S. K., Nat Rev Immunol (2009).
46. Rubtsov, Y. P., Rasmussen, J. P., Chi, E. Y., Fontenot, J., Castelli, L., Ye, X., Treuting, P., Siewe, L., Roers, A., Henderson, W. R., Jr., et al. (2008). Regulatory T cell-derived interleukin-10 limits inflammation at environmental interfaces. Immunity 28, 546-558.
47. Sakaguchi, S., Ono, M., Setoguchi, R., Yagi, H., Hori, S., Fehervari, Z., Shimizu, J., Takahashi, T., and Nomura, T. (2006). Foxp3+ CD25+ CD4+ natural regulatory T cells in dominant self-tolerance and autoimmune disease. Immunol Rev 212, 8-27.
48. Slack, E., Hapfelmeier, S., Stecher, B., Velykoredko, Y., Stoel, M., Lawson, M. A., Geuking, M. B., Beutler, B., Tedder, T. F., Hardt, W. D., et al. (2009). Innate and adaptive immunity cooperate flexibly to maintain host-microbiota mutualism. Science 325, 617620.
49. Smith, K., McCoy, K. D., and Macpherson, A. J. (2007). Use of axenic animals in studying the adaptation of mammals to their commensal intestinal microbiota. Semin Immunol 19, 59-69.
50. Sprinz, H., Kundel, D. W., Dammin, G. J., Horowitz, R. E., Schneider, H., and Formal, S. B. (1961). The response of the germfree guinea pig to oral bacterial challenge with *Escherichia coli* and *Shigella flexneri*. Am J Pathol 39, 681-695.
51. Strauch, U. G., Obermeier, F., Grunwald, N., Gurster, S., Dunger, N., Schultz, M., Griese, D. P., Mahler, M., Scholmerich, J., and Rath, H. C. (2005). Influence of intestinal bacteria on induction of regulatory T cells: lessons from a transfer model of colitis. Gut 54, 15461552.
52. Sutmuller, R. P., den Brok, M. H., Kramer, M., Bennink, E. J., Toonen, L. W., Kullberg, B. J., Joosten, L. A., Akira, S., Netea, M. G., and Adema, G. J. (2006). Toll-like receptor 2 controls expansion and function of regulatory T cells. J Clin Invest 116, 485-494.
53. van Maren, W. W., Jacobs, J. P., de Vries, I. J., Nierkens, S., and Adema, G. J. (2008). Toll-like receptor signalling on Tregs: to suppress or not to suppress? Immunology 124, 445452.
54. Veldhoen, M., Hocking, R. J., Atkins, C. J., Locksley, R. M., and Stockinger, B. (2006). TGFbeta in the context of an inflammatory cytokine milieu supports de novo differentiation of IL-17-producing T cells. Immunity 24, 179-189.
55. Vignali, D. A., Collison, L. W., and Workman, C. J. (2008). How regulatory T cells work. Nat Rev Immunol 8, 523-532.
56. Wang, Q., McLaughlin, R. M., Cobb, B. A., Charrel-Dennis, M., Zaleski, K. J., Golenbock, D., Tzianabos, A. O., and Kasper, D. L. (2006). A bacterial carbohydrate links innate and adaptive responses through Toll-like receptor 2. J Exp Med 203, 2853-2863.
57. Wen, L., Ley, R. E., Volchkov, P. Y., Stranges. P. B., Avanesyan, L., Stonebraker, A. C., Hu, C., Wong, F. S., Szot, G. L., Bluestone, J. A., et al. (2008). Innate immunity and intestinal microbiota in the development of Type 1 diabetes. Nature 455, 1109-1113.
58. Yamazaki, T., Yang, X. O., Chung. Y., Fukunaga, A., Nurieva, R., Pappu, B., Martin-Orozco, N., Kang. H. S., Ma, L., Panopoulos, A. D., et al. (2008). CCR6 regulates the migration of inflammatory and regulatory T cells. J Immunol 181, 8391-8401.
59. Zaph, C., Du, Y., Saenz, S. A., Nair, M. G., Perrigoue, J. G., Taylor, B. C., Troy, A. E., Kobuley, D. E., Kastelein. R. A., Cua, D. J., et al. (2008). Commensal-dependent expression of IL-25 regulates the IL-23-IL-17 axis in the intestine. J Exp Med 205, 2191-2198.
60. Zhou, L., Lopes, J. E., Chong, M. M., Ivanov. II, Min. R., Victora, G. D., Shen, Y., Du, J., Rubtsov, Y. P., Rudensky. A. Y., et al. (2008). TOP-beta-induced Foxp3 inhibits T(H)17 cell differentiation by antagonizing ROR-gammat function. Nature 453, 236-240.

What is claimed is:

1. A method to generate an antigen specific anti-inflammatory regulatory T cell, the method comprising:
   contacting an antigen presenting cell (APC) with a zwitterionic polysaccharide conjugated to the antigen in vitro in absence of a regulatory T cell to generate an APC presenting the antigen, and thereafter
   contacting the APC presenting the antigen with the regulatory T cell in vivo to generate an antigen specific regulatory T cell capable of inhibiting a pro-inflammatory response against the antigen,
   wherein the zwitterionic polysaccharide is selected from polysaccharide A (PSA) and polysaccharide B (PSB) from B. fragilis and the APC is a dendritic cell.

2. The method of claim 1, wherein the polysaccharide is polysaccharide A (PSA) from B. fragilis.

3. The method of claim 1, wherein the zwitterionic polysaccharide is conjugated to the antigen by inclusion of the zwitterionic polysaccharide and the antigen on or within a same vesicle.

4. The method of claim 3, wherein the vesicle is an outer membrane vesicle (OMV).

5. The method of claim 1, wherein the zwitterionic polysaccharide is conjugated to the antigen by physical connection.

6. The method of claim 1, wherein the zwitterionic polysaccharide is conjugated to the antigen by direct or indirect covalent linkage.

7. The method of claim 1, wherein the pro-inflammatory response is a cell mediated inflammatory response.

8. The method claim 7, wherein the cell mediated inflammatory response is a Th17 mediated response.

9. The method of claim 1, wherein the pro-inflammatory response is a humoral inflammatory response.

10. The method of claim 1, wherein the antigen is associated with a condition selected from the group consisting of rheumatoid arthritis, myocarditis, scleroderma, type 1 diabetes, multiple sclerosis, Crohn's disease, ulcerative colitis, Sjorgens syndrome, Hashimoto's thyroiditis, Graves Disease, autoimmune hepatitis, and myasthenia gravis.

11. The method of claim 1, wherein the polysaccharide is polysaccharide A (PSA) from *B. fragilis*.

12. A method to generate an antigen specific anti-inflammatory regulatory T cell, the method comprising:
   contacting an antigen presenting cell (APC) with a zwitterionic polysaccharide conjugated to the antigen in vitro in absence of a regulatory T cell to generate an APC presenting the antigen, and thereafter
   contacting the APC presenting the antigen with the regulatory T cell to generate an antigen specific regulatory T cell capable of inhibiting a pro-inflammatory response against the antigen,
   wherein the zwitterionic polysaccharide is selected from polysaccharide A (PSA) and polysaccharide B (PSB) from *B. fragilis* and the APC is a dendritic cell and
   wherein the zwitterionic polysaccharide is conjugated to the antigen by direct or indirect covalent linkage.

13. The method of claim 12, wherein the pro-inflammatory response is a cell mediated inflammatory response.

14. The method of claim 12, wherein the pro-inflammatory response is a humoral inflammatory response.

15. The method of claim 12, wherein the antigen is associated with a condition selected from the group consisting of rheumatoid arthritis, myocarditis, scleroderma, type I diabetes, multiple sclerosis, Crohn's disease, ulcerative colitis, Sjorgens syndrome, Hashimoto's thyroiditis, Graves Disease, autoimmune hepatitis, and myasthenia gravis.

16. A method to generate an antigen specific anti-inflammatory regulatory T cell, the method comprising:
   contacting an antigen presenting cell (APC) with a zwitterionic polysaccharide conjugated to the antigen in vitro in absence of a regulatory T cell to generate an APC presenting the antigen, and thereafter
   contacting the APC presenting the antigen with the regulatory T cell to generate an antigen specific regulatory T cell capable of inhibiting a pro-inflammatory response against the antigen,
   wherein the zwitterionic polysaccharide is selected from polysaccharide A (PSA) and polysaccharide B (PSB) from *B. fragilis* and the APC is a dendritic cell,
   wherein the antigen is associated with a condition selected from the group consisting of rheumatoid arthritis, myocarditis, scleroderma, type I diabetes, multiple sclerosis, Crohn's disease, ulcerative colitis, Sjorgens syndrome, Hashimoto's thyroiditis, Graves Disease, autoimmune hepatitis, and myasthenia gravis, and
   wherein the antigen is a self-antigen.

17. The method of claim 16, wherein the zwitterionic polysaccharide is conjugated to the antigen by inclusion of the zwitterionic polysaccharide and the antigen on or within a same vesicle.

18. The method of claim 16, wherein the pro-inflammatory response is a cell mediated inflammatory response.

19. The method of claim 16, wherein the pro-inflammatory response is a humoral inflammatory response.

\* \* \* \* \*

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
tacttctgca gcctgtccat        20

<210> SEQ ID NO 2
<211> LENGTH: 20
<212> TYPE: DNA
<213> ORGANISM: Artificial
<220> FEATURE:
<223> OTHER INFORMATION: Primer

<400> SEQUENCE: 2
cagcagagct gggattcata        20

<210> SEQ ID NO 3
<211> LENGTH: 24
<212> TYPE: DNA
<213> ORGANISM: Artificial

```
<220> FEATURE:
<223> OTHER INFORMATION: primer

<400> SEQUENCE: 3
gcaatagttc cttcccagag ttct                                          24

<210> SEQ ID NO 4
<211> LENGTH: 19
<212> TYPE: DNA
<213> ORGANISM: Artificial
<220> FEATURE:
<223> OTHER INFORMATION: Primer

<400> SEQUENCE: 4
ggatggccca tcggataag                                                19

<210> SEQ ID NO 5
<211> LENGTH: 22
<212> TYPE: DNA
<213> ORGANISM: Artificial
<220> FEATURE:
<223> OTHER INFORMATION: Primer

<400> SEQUENCE: 5
ctggacaaca tactgctaac cg                                            22

<210> SEQ ID NO 6
<211> LENGTH: 22
<212> TYPE: DNA
<213> ORGANISM: Artificial
<220> FEATURE:
<223> OTHER INFORMATION: Primer

<400> SEQUENCE: 6
gggcatcact tctaccaggt aa                                            22

<210> SEQ ID NO 7
<211> LENGTH: 19
<212> TYPE: DNA
<213> ORGANISM: Artificial
<220> FEATURE:
<223> OTHER INFORMATION: Primer

<400> SEQUENCE: 7
agcagcagcc tcctagcct                                                19

<210> SEQ ID NO 8
<211> LENGTH: 17
<212> TYPE: DNA
<213> ORGANISM: Artificial
<220> FEATURE:
<223> OTHER INFORMATION: Primer

<400> SEQUENCE: 8
acgccttccg gagggtc                                                  17

<210> SEQ ID NO 9
<211> LENGTH: 20
<212> TYPE: DNA
<213> ORGANISM: Artificial
<220> FEATURE:
<223> OTHER INFORMATION: Primer

<400> SEQUENCE: 9
tgcccagcta taccctggt                                                20
```

```
<210> SEQ ID NO 10
<211> LENGTH: 21
<212> TYPE: DNA
<213> ORGANISM: Artificial
<220> FEATURE:
<223> OTHER INFORMATION: Primer

<400> SEQUENCE: 10
ccgctctcat acacccactt c                                        21

<210> SEQ ID NO 11
<211> LENGTH: 22
<212> TYPE: DNA
<213> ORGANISM: Artificial
<220> FEATURE:
<223> OTHER INFORMATION: Primer

<400> SEQUENCE: 11
aaccatagta cccagttgtc gg                                       22

<210> SEQ ID NO 12
<211> LENGTH: 23
<212> TYPE: DNA
<213> ORGANISM: Artificial
<220> FEATURE:
<223> OTHER INFORMATION: Primer

<400> SEQUENCE: 12
tcctaagcaa cgcatataga cca                                      23

<210> SEQ ID NO 13
<211> LENGTH: 19
<212> TYPE: DNA
<213> ORGANISM: Artificial
<220> FEATURE:
<223> OTHER INFORMATION: Primer

<400> SEQUENCE: 13
aagcgaaact ggcggaaac                                           19

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14
taaccgatgt tgggcatcag                                          20
```